US007087403B2

(12) United States Patent
Brzostowicz et al.

(10) Patent No.: US 7,087,403 B2
(45) Date of Patent: Aug. 8, 2006

(54) BIOLOGICAL PRODUCTION OF TETRADEHYDROLYCOPENE

(75) Inventors: Patricia C. Brzostowicz, West Chester, PA (US); Pierre E. Rouviere, Wilmington, DE (US); Dana M. Walters Pollak, Media, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/987,524

(22) Filed: Nov. 12, 2004

(65) Prior Publication Data

US 2005/0221467 A1    Oct. 6, 2005

Related U.S. Application Data

(60) Provisional application No. 60/519,413, filed on Nov. 12, 2003.

(51) Int. Cl.
*C12P 23/00* (2006.01)
*C12N 9/02* (2006.01)
*C12N 1/20* (2006.01)
*C12N 15/00* (2006.01)
*C07H 21/04* (2006.01)

(52) U.S. Cl. .................. 435/67; 435/183; 435/189; 435/252.3; 435/320.1; 536/23.1; 536/23.2

(58) Field of Classification Search ................ 435/183, 435/189, 252.3, 320.1, 67; 536/23.1, 23.2
See application file for complete search history.

(56) References Cited

U.S. PATENT DOCUMENTS

2002/0051998 A1    5/2002    Schmidt-Dannert et al.

FOREIGN PATENT DOCUMENTS

WO    WO 02/079395 A2    10/2002
WO    WO 03/016503 A2    2/2003

OTHER PUBLICATIONS deSouza et al. Accession AY116713. Dec. 18, 2002.*
H. J. Nelis et al., Principal Carotenoids permitted as additives in foods and feeds, The Journal of Applied Bacteriology, vol. 70:181-191, 1991.
Nicholas J. Miller et al., Antioxidant activities of carotenes and xanthophylls, FEBS Letters, vol. 384:240-242, 1996.
Manuela Albrecht et al., Novel hydroxycarotenoids with improved antioxidative properties produced by gene combination in *Escherichia coli*, Nature Biotechnology, vol. 18:843-846, 2000.
Guido Broszeit et al., Vinylogous beta-Carotenes: Generation, Storage, and Delocalization of Charge in Carotenoids, Liebigs Ann./Recueil, pp. 2205-2213, 1997.
Jurgen Heinze et al., The oligomeric approach—the electrochemistry of conducting polymers in the light of recent research, J. Solid State Electrochem., vol. 2:102-109, 1998.

Harmut Linden et al., Functional Complementation in *Escherichia coli* of Different Phytoene Desaturase Genes and Analysis of Accumulated Carotenes, Zeitschrift fur Naturforsch, vol. 46C:1045-1091, 1991.
Glenn E. Bartley et al., Carotenoid Desaturases from *Rhodobacter capsulatus* and *Neurospora crassa* Are Structurally and Functionally Conserved and Contain Domains Homologous to Flavoprotein Disulfide Oxidoreductases*, The J. of Biol. Chem., vol. 265(26):16020-16024, 1990.
Pablo A. Scolnik et al., Nucleotide Sequence of a Putative Geranylgeranyl Pyrophosphate Synthase (GenBank L40577) from Arabidopsis, Plant Phys., vol. 108:1341-1343, 1995.
Glenn E. Bartley et al., Two *Arabidopsis thaliana* carotene desaturases, phytoene desaturase and S-carotene desaturase, expressed in *Escherichia coli*, catalyze a poly-cis pathway to yield pro-lycopene, Eur. J. Biochem., vol. 259:396-403, 1999.
Alexander Hausmann et al., A Single Five-Step Desaturase Is Involved in the Carotenoid Biosynthesis Pathway to beta-Carotene and Torulene in Neurospora crassa, Fungal Genetics and Biology, vol. 30:147-153, 2000.
Sissel Hertzberg et al., The Structure of Oscillaxanthin*, Phytochemistry, vol. 8:1281-1292, 1969.
Claudia Schmidt-Dannert et al., Molecular breeding of carotenoid biosynthetic pathways, Nature Biotechnology, vol. 18:750-753, 2000.
Paul D. Fraser et al., Expression in *Escherichia coli*, Purification, and Reactivation of the Recombinant *Erwinia uredovora* Phytoene Desaturase*, The J. of Biol. Chem., vol. 267(28):19891-19895, 1992.
Urs Hengartner et al., Synthesis, Isolation, and NMR-Spectroscopic Characterization of Fourteen (Z)-Isomers of Lycopene and of Some Acetylenic Didehydro- and Tetrahydrolycopenes, Helvetica Chimica Acta, vol. 75:1848-1865, 1992.
W. Vetter et al., Carotenoids (ed. O. Isler), Birkhauser, Basel 1971 (book not supplied).
M.L. DeSouza et. al., National Center for Biotechnology Information, Carotenoid Biosynthesis, Accession No. AY166713, 2002.
Michael Mingfu Ling et. al., Approaches to DNA Mutagenesis: An Overview, Analytical Biochemistry, 1997, pp. 157-178, vol. 254.
Claudia Schmidt Dannert et. al., Molecular Breeding of Carotenoid Biosynthetic Pathways, Nature Biotechnology, 2000, pp. 750-753, vol. 18.

* cited by examiner

*Primary Examiner*—Tekchand Saidha
*Assistant Examiner*—Christian L. Fronda

(57) ABSTRACT

Mutant phytoene desaturase genes are provided encoding polypeptides having the ability to convert a phytoene desaturase substrate to tetradehydrolycopene. Both in vivo and in vitro methods are provided using the present phytoene desaturases for tetradehydrolycopene production.

10 Claims, 8 Drawing Sheets

SEQUENCE LISTING

<160> NUMBER OF SEQ ID NOS: 52

<210> SEQ ID NO 1
<211> LENGTH: 912
<212> TYPE: DNA
<213> ORGANISM: Pantoea stewartii

<400> SEQUENCE: 1

```
ttgacggtct gcgcaaaaaa acacgttcac cttactggca tttcggctga gcagttgctg      60
gctgatatcg atagccgcct tgatcagtta ctgccggttc agggtgagcg ggattgtgtg     120
ggtgccgcga tgcgtgaagg cacgctggca ccgggcaaac gtattcgtcc gatgctgctg     180
ttattaacag cgcgcgatct tggctgtgcg atcagtcacg ggggattact ggatttagcc     240
tgcgcggttg aaatggtgca tgctgcctcg ctgattctgg atgatatgcc ctgcatggac     300
gatgcgcaga tgcgtcgggg gcgtcccacc attcacacgc agtacggtga acatgtggcg     360
attctggcgg cggtcgcttt actcagcaaa gcgtttgggg tgattgccga ggctgaaggt     420
ctgacgccga tagccaaaac tcgcgcggtg tcggagctgt ccactgcgat tggcatgcag     480
ggtctggttc agggccagtt taaggacctc tcggaaggcg ataaacccg cagcgccgat     540 gccatactgc taaccaatca gtttaaaacc agcacgctgt tttgcgcgtc aacgcaaatg     600
gcgtccattg cggccaacgc gtcctgcgaa gcgcgtgaga acctgcatcg tttctcgctc     660
gatctcggcc aggcctttca gttgcttgac gatcttaccg atggcatgac cgataccggc     720
aaagacatca atcaggatgc aggtaaatca acgctggtca atttattagg ctcaggcgcg     780
gtcgaagaac gcctgcgaca gcatttgcgc ctggccagtg aacacctttc cgcggcatgc     840
caaaacggcc attccaccac ccaactttt attcaggcct ggtttgacaa aaaactcgct     900
gccgtcagtt aa                                                        912
```

<210> SEQ ID NO 2
<211> LENGTH: 303
<212> TYPE: PRT
<213> ORGANISM: Pantoea stewartii

<400> SEQUENCE: 2

```
Met Thr Val Cys Ala Lys Lys His Val His Leu Thr Gly Ile Ser Ala
1               5                   10                  15

Glu Gln Leu Leu Ala Asp Ile Asp Ser Arg Leu Asp Gln Leu Leu Pro
            20                  25                  30

Val Gln Gly Glu Arg Asp Cys Val Gly Ala Ala Met Arg Glu Gly Thr
        35                  40                  45

Leu Ala Pro Gly Lys Arg Ile Arg Pro Met Leu Leu Leu Thr Ala
    50                  55                  60

Arg Asp Leu Gly Cys Ala Ile Ser His Gly Gly Leu Leu Asp Leu Ala
65                  70                  75                  80

Cys Ala Val Glu Met Val His Ala Ala Ser Leu Ile Leu Asp Asp Met
                85                  90                  95

Pro Cys Met Asp Asp Ala Gln Met Arg Arg Gly Arg Pro Thr Ile His
            100                 105                 110

Thr Gln Tyr Gly Glu His Val Ala Ile Leu Ala Ala Val Ala Leu Leu
        115                 120                 125

Ser Lys Ala Phe Gly Val Ile Ala Glu Ala Glu Gly Leu Thr Pro Ile
    130                 135                 140

Ala Lys Thr Arg Ala Val Ser Glu Leu Ser Thr Ala Ile Gly Met Gln
145                 150                 155                 160

Gly Leu Val Gln Gly Gln Phe Lys Asp Leu Ser Glu Gly Asp Lys Pro
                165                 170                 175

Arg Ser Ala Asp Ala Ile Leu Leu Thr Asn Gln Phe Lys Thr Ser Thr
            180                 185                 190

Leu Phe Cys Ala Ser Thr Gln Met Ala Ser Ile Ala Ala Asn Ala Ser
        195                 200                 205

Cys Glu Ala Arg Glu Asn Leu His Arg Phe Ser Leu Asp Leu Gly Gln
    210                 215                 220

Ala Phe Gln Leu Leu Asp Asp Leu Thr Asp Gly Met Thr Asp Thr Gly
225                 230                 235                 240

Lys Asp Ile Asn Gln Asp Ala Gly Lys Ser Thr Leu Val Asn Leu Leu
                245                 250                 255

Gly Ser Gly Ala Val Glu Glu Arg Leu Arg Gln His Leu Arg Leu Ala
            260                 265                 270

Ser Glu His Leu Ser Ala Ala Cys Gln Asn Gly His Ser Thr Thr Gln
        275                 280                 285

Leu Phe Ile Gln Ala Trp Phe Asp Lys Lys Leu Ala Ala Val Ser
    290                 295                 300
```

<210> SEQ ID NO 3
<211> LENGTH: 1296
<212> TYPE: DNA
<213> ORGANISM: Pantoea stewartii
<220> FEATURE:
<221> NAME/KEY: CDS
<222> LOCATION: (1)..(1296)

<400> SEQUENCE: 3

```
atg agc cat ttt gcg gtg atc gca ccg ccc ttt ttc agc cat gtt cgc      48
Met Ser His Phe Ala Val Ile Ala Pro Pro Phe Phe Ser His Val Arg
1               5                   10                  15 gct ctg caa aac ctt gct cag gaa tta gtg gcc cgc ggt cat cgt gtt      96
Ala Leu Gln Asn Leu Ala Gln Glu Leu Val Ala Arg Gly His Arg Val
            20                  25                  30 acg ttt ttt cag caa cat gac tgc aaa gcg ctg gta acg ggc agc gat     144
Thr Phe Phe Gln Gln His Asp Cys Lys Ala Leu Val Thr Gly Ser Asp
```

```
Thr Phe Phe Gln Gln His Asp Cys Lys Ala Leu Val Thr Gly Ser Asp
         35                  40                  45 atc gga ttc cag acc gtc gga ctg caa acg cat cct ccc ggt tcc tta       192
Ile Gly Phe Gln Thr Val Gly Leu Gln Thr His Pro Pro Gly Ser Leu
 50                  55                  60 tcg cac ctg ctg cac ctg gcc gcg cac cca ctc gga ccc tcg atg tta       240
Ser His Leu Leu His Leu Ala Ala His Pro Leu Gly Pro Ser Met Leu
65                  70                  75                  80 cga ctg atc aat gaa atg gca cgt acc agc gat atg ctt tgc cgg gaa       288
Arg Leu Ile Asn Glu Met Ala Arg Thr Ser Asp Met Leu Cys Arg Glu
                 85                  90                  95 ctg ccc gcc gct ttt cat gcg ttg cag ata gag ggc gtg atc gtt gat       336
Leu Pro Ala Ala Phe His Ala Leu Gln Ile Glu Gly Val Ile Val Asp
            100                 105                 110 caa atg gag ccg gca ggt gca gta gtc gca gaa gcg tca ggt ctg ccg       384
Gln Met Glu Pro Ala Gly Ala Val Val Ala Glu Ala Ser Gly Leu Pro
        115                 120                 125 ttt gtt tcg gtg gcc tgc gcg ctg ccg ctc aac cgc gaa ccg ggt ttg       432
Phe Val Ser Val Ala Cys Ala Leu Pro Leu Asn Arg Glu Pro Gly Leu
    130                 135                 140 cct ctg gcg gtg atg cct ttc gag tac ggc acc agc gat gcg gct cgg       480
Pro Leu Ala Val Met Pro Phe Glu Tyr Gly Thr Ser Asp Ala Ala Arg
145                 150                 155                 160 gaa cgc tat acc acc agc gaa aaa att tat gac tgg ctg atg cga cgt       528
Glu Arg Tyr Thr Thr Ser Glu Lys Ile Tyr Asp Trp Leu Met Arg Arg
                165                 170                 175 cac gat cgt gtg atc gcg cat cat gca tgc aga atg ggt tta gcc ccg       576
His Asp Arg Val Ile Ala His His Ala Cys Arg Met Gly Leu Ala Pro
            180                 185                 190 cgt gaa aaa ctg cat cat tgt ttt tct cca ctg gca caa atc agc cag       624
Arg Glu Lys Leu His His Cys Phe Ser Pro Leu Ala Gln Ile Ser Gln
        195                 200                 205 ttg atc ccc gaa ctg gat ttt ccc cgc aaa gcg ctg cca gac tgc ttt       672
Leu Ile Pro Glu Leu Asp Phe Pro Arg Lys Ala Leu Pro Asp Cys Phe
    210                 215                 220 cat gcg gtt gga ccg tta cgg caa ccc cag ggg acg ccg ggg tca tca       720
His Ala Val Gly Pro Leu Arg Gln Pro Gln Gly Thr Pro Gly Ser Ser
225                 230                 235                 240 act tct tat ttt ccg tcc ccg gac aaa ccc cgt att ttt gcc tcg ctg       768
Thr Ser Tyr Phe Pro Ser Pro Asp Lys Pro Arg Ile Phe Ala Ser Leu
                245                 250                 255 ggc acc ctg cag gga cat cgt tat ggc ctg ttc agg acc atc gcc aaa       816
Gly Thr Leu Gln Gly His Arg Tyr Gly Leu Phe Arg Thr Ile Ala Lys
            260                 265                 270 gcc tgc gaa gag gtg gat gcg cag tta ctg ttg gca cac tgt ggc ggc       864
Ala Cys Glu Glu Val Asp Ala Gln Leu Leu Leu Ala His Cys Gly Gly
        275                 280                 285 ctc tca gcc acg cag gca ggt gaa ctg gcc cgg ggc ggg gac att cag       912
Leu Ser Ala Thr Gln Ala Gly Glu Leu Ala Arg Gly Gly Asp Ile Gln
    290                 295                 300 gtt gtg gat ttt gcc gat caa tcc gca gca ctt tca cag gca cag ttg       960
Val Val Asp Phe Ala Asp Gln Ser Ala Ala Leu Ser Gln Ala Gln Leu
305                 310                 315                 320 aca atc aca cat ggt ggg atg aat acg gta ctg gac gct att gct tcc      1008
Thr Ile Thr His Gly Gly Met Asn Thr Val Leu Asp Ala Ile Ala Ser
                325                 330                 335 cgc aca ccg cta ctg gcg ctg ccg ctg gca ttt gat caa cct ggc gtg      1056
Arg Thr Pro Leu Leu Ala Leu Pro Leu Ala Phe Asp Gln Pro Gly Val
            340                 345                 350
```

```
gca tca cga att gtt tat cat ggc atc ggc aag cgt gcg tct cgg ttt      1104
Ala Ser Arg Ile Val Tyr His Gly Ile Gly Lys Arg Ala Ser Arg Phe
    355                 360                 365 act acc agc cat gcg ctg gcg cgg cag att cga tcg ctg ctg act aac      1152
Thr Thr Ser His Ala Leu Ala Arg Gln Ile Arg Ser Leu Leu Thr Asn
370                 375                 380 acc gat tac ccg cag cgt atg aca aaa att cag gcc gca ttg cgt ctg      1200
Thr Asp Tyr Pro Gln Arg Met Thr Lys Ile Gln Ala Ala Leu Arg Leu
385                 390                 395                 400 gca ggc ggc aca cca gcc gcc gcc gat att gtt gaa cag gcg atg cgg      1248
Ala Gly Gly Thr Pro Ala Ala Ala Asp Ile Val Glu Gln Ala Met Arg
                405                 410                 415 acc tgt cag cca gta ctc agt ggg cag gat tat gca acc gca cta tga      1296
Thr Cys Gln Pro Val Leu Ser Gly Gln Asp Tyr Ala Thr Ala Leu
            420                 425                 430
```

<210> SEQ ID NO 4
<211> LENGTH: 431
<212> TYPE: PRT
<213> ORGANISM: Pantoea stewartii

<400> SEQUENCE: 4

```
Met Ser His Phe Ala Val Ile Ala Pro Pro Phe Ser His Val Arg
1               5                   10                  15

Ala Leu Gln Asn Leu Ala Gln Glu Leu Val Ala Arg Gly His Arg Val
                20                  25                  30

Thr Phe Phe Gln Gln His Asp Cys Lys Ala Leu Val Thr Gly Ser Asp
            35                  40                  45

Ile Gly Phe Gln Thr Val Gly Leu Gln Thr His Pro Pro Gly Ser Leu
        50                  55                  60

Ser His Leu Leu His Leu Ala Ala His Pro Leu Gly Pro Ser Met Leu
65                  70                  75                  80

Arg Leu Ile Asn Glu Met Ala Arg Thr Ser Asp Met Leu Cys Arg Glu
                85                  90                  95

Leu Pro Ala Ala Phe His Ala Leu Gln Ile Glu Gly Val Ile Val Asp
            100                 105                 110

Gln Met Glu Pro Ala Gly Ala Val Val Ala Glu Ala Ser Gly Leu Pro
        115                 120                 125

Phe Val Ser Val Ala Cys Ala Leu Pro Leu Asn Arg Glu Pro Gly Leu
    130                 135                 140

Pro Leu Ala Val Met Pro Phe Glu Tyr Gly Thr Ser Asp Ala Ala Arg
145                 150                 155                 160

Glu Arg Tyr Thr Thr Ser Glu Lys Ile Tyr Asp Trp Leu Met Arg Arg
                165                 170                 175

His Asp Arg Val Ile Ala His Ala Cys Arg Met Gly Leu Ala Pro
            180                 185                 190

Arg Glu Lys Leu His His Cys Phe Ser Pro Leu Ala Gln Ile Ser Gln
        195                 200                 205

Leu Ile Pro Glu Leu Asp Phe Pro Arg Lys Ala Leu Pro Asp Cys Phe
    210                 215                 220

His Ala Val Gly Pro Leu Arg Gln Pro Gln Gly Thr Pro Gly Ser Ser
225                 230                 235                 240

Thr Ser Tyr Phe Pro Ser Pro Asp Lys Pro Arg Ile Phe Ala Ser Leu
                245                 250                 255

Gly Thr Leu Gln Gly His Arg Tyr Gly Leu Phe Arg Thr Ile Ala Lys
            260                 265                 270
```

```
Ala Cys Glu Glu Val Asp Ala Gln Leu Leu Ala His Cys Gly Gly
        275                 280                 285

Leu Ser Ala Thr Gln Ala Gly Glu Leu Ala Arg Gly Gly Asp Ile Gln
        290                 295                 300

Val Val Asp Phe Ala Asp Gln Ser Ala Ala Leu Ser Gln Ala Gln Leu
305                 310                 315                 320

Thr Ile Thr His Gly Gly Met Asn Thr Val Leu Asp Ala Ile Ala Ser
                        325                 330                 335

Arg Thr Pro Leu Leu Ala Leu Pro Leu Ala Phe Asp Gln Pro Gly Val
                340                 345                 350

Ala Ser Arg Ile Val Tyr His Gly Ile Gly Lys Arg Ala Ser Arg Phe
            355                 360                 365

Thr Thr Ser His Ala Leu Ala Arg Gln Ile Arg Ser Leu Leu Thr Asn
        370                 375                 380

Thr Asp Tyr Pro Gln Arg Met Thr Lys Ile Gln Ala Ala Leu Arg Leu
385                 390                 395                 400

Ala Gly Gly Thr Pro Ala Ala Ala Asp Ile Val Glu Gln Ala Met Arg
                    405                 410                 415

Thr Cys Gln Pro Val Leu Ser Gly Gln Asp Tyr Ala Thr Ala Leu
            420                 425                 430

<210> SEQ ID NO 5
<211> LENGTH: 1149
<212> TYPE: DNA
<213> ORGANISM: Pantoea stewartii
<220> FEATURE:
<221> NAME/KEY: CDS
<222> LOCATION: (1)..(1149)

<400> SEQUENCE: 5 atg caa ccg cac tat gat ctc att ctg gtc ggt gcc ggt ctg gct aat      48
Met Gln Pro His Tyr Asp Leu Ile Leu Val Gly Ala Gly Leu Ala Asn
1               5                  10                  15 ggc ctt atc gcg ctc cgg ctt cag caa cag cat ccg gat atg cgg atc      96
Gly Leu Ile Ala Leu Arg Leu Gln Gln Gln His Pro Asp Met Arg Ile
            20                  25                  30 ttg ctt att gag gcg ggt cct gag gcg gga ggg aac cat acc tgg tcc     144
Leu Leu Ile Glu Ala Gly Pro Glu Ala Gly Gly Asn His Thr Trp Ser
        35                  40                  45 ttt cac gaa gag gat tta acg ctg aat cag cat cgc tgg ata gcg ccg     192
Phe His Glu Glu Asp Leu Thr Leu Asn Gln His Arg Trp Ile Ala Pro
    50                  55                  60 ctt gtg gtc cat cac tgg ccc gac tac cag gtt cgt ttc ccc caa cgc     240
Leu Val Val His His Trp Pro Asp Tyr Gln Val Arg Phe Pro Gln Arg
65                  70                  75                  80 cgt cgc cat gtg aac agt ggc tac tac tgc gtg acc tcc cgg cat ttc     288
Arg Arg His Val Asn Ser Gly Tyr Tyr Cys Val Thr Ser Arg His Phe
                85                  90                  95 gcc ggg ata ctc cgg caa cag ttt gga caa cat tta tgg ctg cat acc     336
Ala Gly Ile Leu Arg Gln Gln Phe Gly Gln His Leu Trp Leu His Thr
            100                 105                 110 gcg gtt tca gcc gtt cat gct gaa tcg gtc cag tta gcg gat ggc cgg     384
Ala Val Ser Ala Val His Ala Glu Ser Val Gln Leu Ala Asp Gly Arg
        115                 120                 125 att att cat gcc agt aca gtg atc gac gga cgg ggt tac acg cct gat     432
Ile Ile His Ala Ser Thr Val Ile Asp Gly Arg Gly Tyr Thr Pro Asp
    130                 135                 140 tct gca cta cgc gta gga ttc cag gca ttt atc ggt cag gag tgg caa     480
Ser Ala Leu Arg Val Gly Phe Gln Ala Phe Ile Gly Gln Glu Trp Gln
```

```
                                                                     145                 150                 155                 160
ctg agc gcg ccg cat ggt tta tcg tca ccg att atc atg gat gcg acg       528
Leu Ser Ala Pro His Gly Leu Ser Ser Pro Ile Ile Met Asp Ala Thr
                165                 170                 175 gtc gat cag caa aat ggc tac cgc ttt gtt tat acc ctg ccg ctt tcc       576
Val Asp Gln Gln Asn Gly Tyr Arg Phe Val Tyr Thr Leu Pro Leu Ser
            180                 185                 190 gca acc gca ctg ctg atc gaa gac aca cac tac att gac aag gct aat       624
Ala Thr Ala Leu Leu Ile Glu Asp Thr His Tyr Ile Asp Lys Ala Asn
        195                 200                 205 ctt cag gcc gaa cgg gcg cgt cag aac att cgc gat tat gct gcg cga       672
Leu Gln Ala Glu Arg Ala Arg Gln Asn Ile Arg Asp Tyr Ala Ala Arg
    210                 215                 220 cag ggt tgg ccg tta cag acg ttg ctg cgg gaa gaa cag ggt gca ttg       720
Gln Gly Trp Pro Leu Gln Thr Leu Leu Arg Glu Glu Gln Gly Ala Leu
225                 230                 235                 240 ccc att acg tta acg ggc gat aat cgt cag ttt tgg caa cag caa ccg       768
Pro Ile Thr Leu Thr Gly Asp Asn Arg Gln Phe Trp Gln Gln Gln Pro
                245                 250                 255 caa gcc tgt agc gga tta cgc gcc ggg ctg ttt cat ccg aca acc ggc       816
Gln Ala Cys Ser Gly Leu Arg Ala Gly Leu Phe His Pro Thr Thr Gly
            260                 265                 270 tac tcc cta ccg ctc gcg gtg gcg ctg gcc gat cgt ctc agc gcg ctg       864
Tyr Ser Leu Pro Leu Ala Val Ala Leu Ala Asp Arg Leu Ser Ala Leu
        275                 280                 285 gat gtg ttt acc tct tcc tct gtt cac cag acg att gct cac ttt gcc       912
Asp Val Phe Thr Ser Ser Ser Val His Gln Thr Ile Ala His Phe Ala
    290                 295                 300 cag caa cgt tgg cag caa cag ggg ttt ttc cgc atg ctg aat cgc atg       960
Gln Gln Arg Trp Gln Gln Gln Gly Phe Phe Arg Met Leu Asn Arg Met
305                 310                 315                 320 ttg ttt tta gcc gga ccg gcc gag tca cgc tgg cgt gtg atg cag cgt      1008
Leu Phe Leu Ala Gly Pro Ala Glu Ser Arg Trp Arg Val Met Gln Arg
                325                 330                 335 ttc tat ggc tta ccc gag gat ttg att gcc cgc ttt tat gcg gga aaa      1056
Phe Tyr Gly Leu Pro Glu Asp Leu Ile Ala Arg Phe Tyr Ala Gly Lys
            340                 345                 350 ctc acc gtg acc gat cgg cta cgc att ctg agc ggc aag ccg ccc gtt      1104
Leu Thr Val Thr Asp Arg Leu Arg Ile Leu Ser Gly Lys Pro Pro Val
        355                 360                 365 ccc gtt ttc gcg gca ttg cag gca att atg acg act cat cgt tga          1149
Pro Val Phe Ala Ala Leu Gln Ala Ile Met Thr Thr His Arg
    370                 375                 380

<210> SEQ ID NO 6
<211> LENGTH: 382
<212> TYPE: PRT
<213> ORGANISM: Pantoea stewartii

<400> SEQUENCE: 6

Met Gln Pro His Tyr Asp Leu Ile Leu Val Gly Ala Gly Leu Ala Asn
1               5                   10                  15

Gly Leu Ile Ala Leu Arg Leu Gln Gln His Pro Asp Met Arg Ile
            20                  25                  30

Leu Leu Ile Glu Ala Gly Pro Glu Ala Gly Gly Asn His Thr Trp Ser
        35                  40                  45

Phe His Glu Glu Asp Leu Thr Leu Asn Gln His Arg Trp Ile Ala Pro
    50                  55                  60

Leu Val Val His His Trp Pro Asp Tyr Gln Val Arg Phe Pro Gln Arg
```

```
                65                  70                  75                  80
Arg Arg His Val Asn Ser Gly Tyr Tyr Cys Val Thr Ser Arg His Phe
                    85                  90                  95

Ala Gly Ile Leu Arg Gln Gln Phe Gly Gln His Leu Trp Leu His Thr
            100                 105                 110

Ala Val Ser Ala Val His Ala Glu Ser Val Gln Leu Ala Asp Gly Arg
            115                 120                 125

Ile Ile His Ala Ser Thr Val Ile Asp Gly Arg Gly Tyr Thr Pro Asp
    130                 135                 140

Ser Ala Leu Arg Val Gly Phe Gln Ala Phe Ile Gly Gln Glu Trp Gln
145                 150                 155                 160

Leu Ser Ala Pro His Gly Leu Ser Ser Pro Ile Ile Met Asp Ala Thr
                165                 170                 175

Val Asp Gln Gln Asn Gly Tyr Arg Phe Val Tyr Thr Leu Pro Leu Ser
            180                 185                 190

Ala Thr Ala Leu Leu Ile Glu Asp Thr His Tyr Ile Asp Lys Ala Asn
            195                 200                 205

Leu Gln Ala Glu Arg Ala Arg Gln Asn Ile Arg Asp Tyr Ala Ala Arg
    210                 215                 220

Gln Gly Trp Pro Leu Gln Thr Leu Leu Arg Glu Gln Gly Ala Leu
225                 230                 235                 240

Pro Ile Thr Leu Thr Gly Asp Asn Arg Gln Phe Trp Gln Gln Pro
                245                 250                 255

Gln Ala Cys Ser Gly Leu Arg Ala Gly Leu Phe His Pro Thr Thr Gly
            260                 265                 270

Tyr Ser Leu Pro Leu Ala Val Ala Leu Ala Asp Arg Leu Ser Ala Leu
            275                 280                 285

Asp Val Phe Thr Ser Ser Val His Gln Thr Ile Ala His Phe Ala
    290                 295                 300

Gln Gln Arg Trp Gln Gln Gly Phe Phe Arg Met Leu Asn Arg Met
305                 310                 315                 320

Leu Phe Leu Ala Gly Pro Ala Glu Ser Arg Trp Arg Val Met Gln Arg
                325                 330                 335

Phe Tyr Gly Leu Pro Glu Asp Leu Ile Ala Arg Phe Tyr Ala Gly Lys
            340                 345                 350

Leu Thr Val Thr Asp Arg Leu Arg Ile Leu Ser Gly Lys Pro Pro Val
            355                 360                 365

Pro Val Phe Ala Ala Leu Gln Ala Ile Met Thr Thr His Arg
    370                 375                 380

<210> SEQ ID NO 7
<211> LENGTH: 1479
<212> TYPE: DNA
<213> ORGANISM: Pantoea stewartii
<220> FEATURE:
<221> NAME/KEY: CDS
<222> LOCATION: (1)..(1479)

<400> SEQUENCE: 7 atg aaa cca act acg gta att ggt gcg ggc ttt ggt ggc ctg gca ctg      48
Met Lys Pro Thr Thr Val Ile Gly Ala Gly Phe Gly Gly Leu Ala Leu
1               5                   10                  15 gca att cgt tta cag gcc gca ggt att cct gtt ttg ctg ctt gag cag      96
Ala Ile Arg Leu Gln Ala Ala Gly Ile Pro Val Leu Leu Leu Glu Gln
            20                  25                  30 cgc gac aag ccg ggt ggc cgg gct tat gtt tat cag gag cag ggc ttt     144
```

```
                                                            -continued

Arg Asp Lys Pro Gly Gly Arg Ala Tyr Val Tyr Gln Glu Gln Gly Phe
               35                  40                  45 act ttt gat gca ggc cct acc gtt atc acc gat ccc agc gcg att gaa           192
Thr Phe Asp Ala Gly Pro Thr Val Ile Thr Asp Pro Ser Ala Ile Glu
 50                  55                  60 gaa ctg ttt gct ctg gcc ggt aaa cag ctt aag gat tac gtc gag ctg           240
Glu Leu Phe Ala Leu Ala Gly Lys Gln Leu Lys Asp Tyr Val Glu Leu
 65                  70                  75                  80 ttg ccg gtc acg ccg ttt tat cgc ctg tgc tgg gag tcc ggc aag gtc           288
Leu Pro Val Thr Pro Phe Tyr Arg Leu Cys Trp Glu Ser Gly Lys Val
                 85                  90                  95 ttc aat tac gat aac gac cag gcc cag tta gaa gcg cag ata cag cag           336
Phe Asn Tyr Asp Asn Asp Gln Ala Gln Leu Glu Ala Gln Ile Gln Gln
            100                 105                 110 ttt aat ccg cgc gat gtt gcg ggt tat cga gcg ttc ctt gac tat tcg           384
Phe Asn Pro Arg Asp Val Ala Gly Tyr Arg Ala Phe Leu Asp Tyr Ser
        115                 120                 125 cgt gcc gta ttc aat gag ggc tat ctg aag ctc ggc act gtg cct ttt           432
Arg Ala Val Phe Asn Glu Gly Tyr Leu Lys Leu Gly Thr Val Pro Phe
    130                 135                 140 tta tcg ttc aaa gac atg ctt cgg gcc gcg ccc cag ttg gca aag ctg           480
Leu Ser Phe Lys Asp Met Leu Arg Ala Ala Pro Gln Leu Ala Lys Leu
145                 150                 155                 160 cag gca tgg cgc agc gtt tac agt aaa gtt gcc ggc tac att gag gat           528
Gln Ala Trp Arg Ser Val Tyr Ser Lys Val Ala Gly Tyr Ile Glu Asp
                165                 170                 175 gag cat ctt cgg cag gcg ttt tct ttt cac tcg ctc tta gtg ggg ggg           576
Glu His Leu Arg Gln Ala Phe Ser Phe His Ser Leu Leu Val Gly Gly
            180                 185                 190 aat ccg ttt gca acc tcg tcc att tat acg ctg att cac gcg tta gaa           624
Asn Pro Phe Ala Thr Ser Ser Ile Tyr Thr Leu Ile His Ala Leu Glu
        195                 200                 205 cgg gaa tgg ggc gtc tgg ttt cca cgc ggt gga acc ggt gcg ctg gtc           672
Arg Glu Trp Gly Val Trp Phe Pro Arg Gly Gly Thr Gly Ala Leu Val
    210                 215                 220 aat ggc atg atc aag ctg ttt cag gat ctg ggc ggc gaa gtc gtg ctt           720
Asn Gly Met Ile Lys Leu Phe Gln Asp Leu Gly Gly Glu Val Val Leu
225                 230                 235                 240 aac gcc cgg gtc agt cat atg gaa acc gtt ggg gac aag att cag gcc           768
Asn Ala Arg Val Ser His Met Glu Thr Val Gly Asp Lys Ile Gln Ala
                245                 250                 255 gtg cag ttg gaa gac ggc aga cgg ttt gaa acc tgc gcg gtg gcg tcg           816
Val Gln Leu Glu Asp Gly Arg Arg Phe Glu Thr Cys Ala Val Ala Ser
            260                 265                 270 aac gct gat gtt gta cat acc tat cgc gat ctg ctg tct cag cat ccc           864
Asn Ala Asp Val Val His Thr Tyr Arg Asp Leu Leu Ser Gln His Pro
        275                 280                 285 gca gcc gct aag cag gcg aaa aaa ctg caa tcc aag cgt atg agt aac           912
Ala Ala Ala Lys Gln Ala Lys Lys Leu Gln Ser Lys Arg Met Ser Asn
    290                 295                 300 tca ctg ttt gta ctc tat ttt ggt ctc aac cat cac gat caa ctc              960
Ser Leu Phe Val Leu Tyr Phe Gly Leu Asn His His Asp Gln Leu
305                 310                 315                 320 gcc cat cat acc gtc tgt ttt ggg cca cgc tac cgt gaa ctg att cac          1008
Ala His His Thr Val Cys Phe Gly Pro Arg Tyr Arg Glu Leu Ile His
                325                 330                 335 gaa att ttt aac cat gat ggt ctg gct gag gat ttt tcg ctt tat tta         1056
Glu Ile Phe Asn His Asp Gly Leu Ala Glu Asp Phe Ser Leu Tyr Leu
            340                 345                 350
```

-continued

```
cac gca cct tgt gtc acg gat ccg tca ctg gca ccg gaa ggg tgc ggc      1104
His Ala Pro Cys Val Thr Asp Pro Ser Leu Ala Pro Glu Gly Cys Gly
        355                 360                 365 agc tat tat gtg ctg gcg cct gtt cca cac tta ggc acg gcg aac ctc      1152
Ser Tyr Tyr Val Leu Ala Pro Val Pro His Leu Gly Thr Ala Asn Leu
370                 375                 380 gac tgg gcg gta gaa gga ccc cga ctg cgt gat cgt att ttt gac tac      1200
Asp Trp Ala Val Glu Gly Pro Arg Leu Arg Asp Arg Ile Phe Asp Tyr
385                 390                 395                 400 ctt gag caa cat tac atg cct ggc ttg cga agc cag ttg gtg acg cac      1248
Leu Glu Gln His Tyr Met Pro Gly Leu Arg Ser Gln Leu Val Thr His
                405                 410                 415 cgt atg ttt acg ccg ttc gat ttc cgc gac gag ctc aat gcc tgg caa      1296
Arg Met Phe Thr Pro Phe Asp Phe Arg Asp Glu Leu Asn Ala Trp Gln
            420                 425                 430 ggt tcg gcc ttc tcg gtt gaa cct att ctg acc cag agc gcc tgg ttc      1344
Gly Ser Ala Phe Ser Val Glu Pro Ile Leu Thr Gln Ser Ala Trp Phe
        435                 440                 445 cga cca cat aac cgc gat aag cac att gat aat ctt tat ctg gtt ggc      1392
Arg Pro His Asn Arg Asp Lys His Ile Asp Asn Leu Tyr Leu Val Gly
450                 455                 460 gca ggc acc cat cct ggc gcg ggc att ccc ggc gta atc ggc tcg gcg      1440
Ala Gly Thr His Pro Gly Ala Gly Ile Pro Gly Val Ile Gly Ser Ala
465                 470                 475                 480 aag gcg acg gca ggc tta atg ctg gag gac ctg att tga                  1479
Lys Ala Thr Ala Gly Leu Met Leu Glu Asp Leu Ile
                485                 490
```

<210> SEQ ID NO 8
<211> LENGTH: 492
<212> TYPE: PRT
<213> ORGANISM: Pantoea stewartii

<400> SEQUENCE: 8

```
Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Glu Gln
            20                  25                  30

Arg Asp Lys Pro Gly Gly Arg Ala Tyr Val Tyr Gln Glu Gln Gly Phe
        35                  40                  45

Thr Phe Asp Ala Gly Pro Thr Val Ile Thr Asp Pro Ser Ala Ile Glu
    50                  55                  60

Glu Leu Phe Ala Leu Ala Gly Lys Gln Leu Lys Asp Tyr Val Glu Leu
65                  70                  75                  80

Leu Pro Val Thr Pro Phe Tyr Arg Leu Cys Trp Glu Ser Gly Lys Val
                85                  90                  95

Phe Asn Tyr Asp Asn Asp Gln Ala Gln Leu Glu Ala Gln Ile Gln Gln
            100                 105                 110

Phe Asn Pro Arg Asp Val Ala Gly Tyr Arg Ala Phe Leu Asp Tyr Ser
        115                 120                 125

Arg Ala Val Phe Asn Glu Gly Tyr Leu Lys Leu Gly Thr Val Pro Phe
    130                 135                 140

Leu Ser Phe Lys Asp Met Leu Arg Ala Ala Pro Gln Leu Ala Lys Leu
145                 150                 155                 160

Gln Ala Trp Arg Ser Val Tyr Ser Lys Val Ala Gly Tyr Ile Glu Asp
                165                 170                 175

Glu His Leu Arg Gln Ala Phe Ser Phe His Ser Leu Leu Val Gly Gly
            180                 185                 190
```

-continued

```
Asn Pro Phe Ala Thr Ser Ser Ile Tyr Thr Leu Ile His Ala Leu Glu
            195                 200                 205
Arg Glu Trp Gly Val Trp Phe Pro Arg Gly Gly Thr Gly Ala Leu Val
        210                 215                 220
Asn Gly Met Ile Lys Leu Phe Gln Asp Leu Gly Gly Glu Val Val Leu
225                 230                 235                 240
Asn Ala Arg Val Ser His Met Glu Thr Val Gly Asp Lys Ile Gln Ala
                245                 250                 255
Val Gln Leu Glu Asp Gly Arg Arg Phe Glu Thr Cys Ala Val Ala Ser
            260                 265                 270
Asn Ala Asp Val Val His Thr Tyr Arg Asp Leu Leu Ser Gln His Pro
        275                 280                 285
Ala Ala Ala Lys Gln Ala Lys Lys Leu Gln Ser Lys Arg Met Ser Asn
    290                 295                 300
Ser Leu Phe Val Leu Tyr Phe Gly Leu Asn His His Asp Gln Leu
305                 310                 315                 320
Ala His His Thr Val Cys Phe Gly Pro Arg Tyr Arg Glu Leu Ile His
                325                 330                 335
Glu Ile Phe Asn His Asp Gly Leu Ala Glu Asp Phe Ser Leu Tyr Leu
            340                 345                 350
His Ala Pro Cys Val Thr Asp Pro Ser Leu Ala Pro Glu Gly Cys Gly
        355                 360                 365
Ser Tyr Tyr Val Leu Ala Pro Val Pro His Leu Gly Thr Ala Asn Leu
    370                 375                 380
Asp Trp Ala Val Glu Gly Pro Arg Leu Arg Asp Arg Ile Phe Asp Tyr
385                 390                 395                 400
Leu Glu Gln His Tyr Met Pro Gly Leu Arg Ser Gln Leu Val Thr His
                405                 410                 415
Arg Met Phe Thr Pro Phe Asp Phe Arg Asp Glu Leu Asn Ala Trp Gln
            420                 425                 430
Gly Ser Ala Phe Ser Val Glu Pro Ile Leu Thr Gln Ser Ala Trp Phe
        435                 440                 445
Arg Pro His Asn Arg Asp Lys His Ile Asp Asn Leu Tyr Leu Val Gly
    450                 455                 460
Ala Gly Thr His Pro Gly Ala Gly Ile Pro Gly Val Ile Gly Ser Ala
465                 470                 475                 480
Lys Ala Thr Ala Gly Leu Met Leu Glu Asp Leu Ile
                485                 490
```

<210> SEQ ID NO 9
<211> LENGTH: 891
<212> TYPE: DNA
<213> ORGANISM: Pantoea stewartii
<220> FEATURE:
<221> NAME/KEY: CDS
<222> LOCATION: (1)..(891)

<400> SEQUENCE: 9

```
atg gcg gtt ggc tcg aaa agc ttt gcg act gca tcg acg ctt ttc gac       48
Met Ala Val Gly Ser Lys Ser Phe Ala Thr Ala Ser Thr Leu Phe Asp
1               5                   10                  15 gcc aaa acc cgt cgc agc gtg ctg atg ctt tac gca tgg tgc cgc cac       96
Ala Lys Thr Arg Arg Ser Val Leu Met Leu Tyr Ala Trp Cys Arg His
                20                  25                  30 tgc gac gac gtc att gac gat caa aca ctg ggc ttt cat gcc gac cag      144
Cys Asp Asp Val Ile Asp Asp Gln Thr Leu Gly Phe His Ala Asp Gln
```

```
                  35                 40                   45
ccc tct tcg cag atg cct gag cag cgc ctg cag cag ctt gaa atg aaa     192
Pro Ser Ser Gln Met Pro Glu Gln Arg Leu Gln Gln Leu Glu Met Lys
    50                  55                  60 acg cgt cag gcc tac gcc ggt tcg caa atg cac gag ccc gct ttt gcc     240
Thr Arg Gln Ala Tyr Ala Gly Ser Gln Met His Glu Pro Ala Phe Ala
65                  70                  75                  80 gcg ttt cag gag gtc gcg atg gcg cat gat atc gct ccc gcc tac gcg     288
Ala Phe Gln Glu Val Ala Met Ala His Asp Ile Ala Pro Ala Tyr Ala
                85                  90                  95 ttc gac cat ctg gaa ggt ttt gcc atg gat gtg cgc gaa acg cgc tac     336
Phe Asp His Leu Glu Gly Phe Ala Met Asp Val Arg Glu Thr Arg Tyr
            100                 105                 110 ctg aca ctg gac gat acg ctg cgt tat tgc tat cac gtc gcc ggt gtt     384
Leu Thr Leu Asp Asp Thr Leu Arg Tyr Cys Tyr His Val Ala Gly Val
        115                 120                 125 gtg ggc ctg atg atg gcg caa att atg ggc gtt cgc gat aac gcc acg     432
Val Gly Leu Met Met Ala Gln Ile Met Gly Val Arg Asp Asn Ala Thr
    130                 135                 140 ctc gat cgc gcc tgc gat ctc ggg ctg gct ttc cag ttg acc aac att     480
Leu Asp Arg Ala Cys Asp Leu Gly Leu Ala Phe Gln Leu Thr Asn Ile
145                 150                 155                 160 gcg cgt gat att gtc gac gat gct cag gtg ggc cgc tgt tat ctg cct     528
Ala Arg Asp Ile Val Asp Asp Ala Gln Val Gly Arg Cys Tyr Leu Pro
                165                 170                 175 gaa agc tgg ctg gaa gag gaa gga ctg acg aaa gcg aat tat gct gcg     576
Glu Ser Trp Leu Glu Glu Glu Gly Leu Thr Lys Ala Asn Tyr Ala Ala
            180                 185                 190 cca gaa aac cgg cag gcc tta agc cgt atc gcc ggg cga ctg gta cgg     624
Pro Glu Asn Arg Gln Ala Leu Ser Arg Ile Ala Gly Arg Leu Val Arg
        195                 200                 205 gaa gcg gaa ccc tat tac gta tca tca atg gcc ggt ctg gca caa tta     672
Glu Ala Glu Pro Tyr Tyr Val Ser Ser Met Ala Gly Leu Ala Gln Leu
    210                 215                 220 ccc tta cgc tcg gcc tgg gcc atc gcg aca gcg aag cag gtg tac cgt     720
Pro Leu Arg Ser Ala Trp Ala Ile Ala Thr Ala Lys Gln Val Tyr Arg
225                 230                 235                 240 aaa att ggc gtg aaa gtt gaa cag gcc ggt aag cag gcc tgg gat cat     768
Lys Ile Gly Val Lys Val Glu Gln Ala Gly Lys Gln Ala Trp Asp His
                245                 250                 255 cgc cag tcc acg tcc acc gcc gaa aaa tta acg ctt ttg ctg acg gca     816
Arg Gln Ser Thr Ser Thr Ala Glu Lys Leu Thr Leu Leu Leu Thr Ala
            260                 265                 270 tcc ggt cag gca gtt act tcc cgg atg aag acg tat cca ccc cgt cct     864
Ser Gly Gln Ala Val Thr Ser Arg Met Lys Thr Tyr Pro Pro Arg Pro
        275                 280                 285 gct cat ctc tgg cag cgc ccg atc tag                                 891
Ala His Leu Trp Gln Arg Pro Ile
    290                 295

<210> SEQ ID NO 10
<211> LENGTH: 296
<212> TYPE: PRT
<213> ORGANISM: Pantoea stewartii

<400> SEQUENCE: 10

Met Ala Val Gly Ser Lys Ser Phe Ala Thr Ala Ser Thr Leu Phe Asp
1               5                   10                  15

Ala Lys Thr Arg Arg Ser Val Leu Met Leu Tyr Ala Trp Cys Arg His
            20                  25                  30
```

```
Cys Asp Asp Val Ile Asp Gln Thr Leu Gly Phe His Ala Asp Gln
         35                  40                  45

Pro Ser Ser Gln Met Pro Glu Gln Arg Leu Gln Gln Leu Glu Met Lys
 50                  55                  60

Thr Arg Gln Ala Tyr Ala Gly Ser Gln Met His Glu Pro Ala Phe Ala
 65                  70                  75                  80

Ala Phe Gln Glu Val Ala Met Ala His Asp Ile Ala Pro Ala Tyr Ala
                 85                  90                  95

Phe Asp His Leu Glu Gly Phe Ala Met Asp Val Arg Glu Thr Arg Tyr
                100                 105                 110

Leu Thr Leu Asp Asp Thr Leu Arg Tyr Cys Tyr His Val Ala Gly Val
            115                 120                 125

Val Gly Leu Met Met Ala Gln Ile Met Gly Val Arg Asp Asn Ala Thr
        130                 135                 140

Leu Asp Arg Ala Cys Asp Leu Gly Leu Ala Phe Gln Leu Thr Asn Ile
145                 150                 155                 160

Ala Arg Asp Ile Val Asp Asp Ala Gln Val Gly Arg Cys Tyr Leu Pro
                165                 170                 175

Glu Ser Trp Leu Glu Glu Gly Leu Thr Lys Ala Asn Tyr Ala Ala
                180                 185                 190

Pro Glu Asn Arg Gln Ala Leu Ser Arg Ile Ala Gly Arg Leu Val Arg
            195                 200                 205

Glu Ala Glu Pro Tyr Tyr Val Ser Ser Met Ala Gly Leu Ala Gln Leu
        210                 215                 220

Pro Leu Arg Ser Ala Trp Ala Ile Ala Thr Ala Lys Gln Val Tyr Arg
225                 230                 235                 240

Lys Ile Gly Val Lys Val Glu Gln Ala Gly Lys Gln Ala Trp Asp His
                245                 250                 255

Arg Gln Ser Thr Ser Thr Ala Glu Lys Leu Thr Leu Leu Thr Ala
            260                 265                 270

Ser Gly Gln Ala Val Thr Ser Arg Met Lys Thr Tyr Pro Pro Arg Pro
        275                 280                 285

Ala His Leu Trp Gln Arg Pro Ile
        290                 295

<210> SEQ ID NO 11
<211> LENGTH: 528
<212> TYPE: DNA
<213> ORGANISM: Pantoea stewartii
<220> FEATURE:
<221> NAME/KEY: CDS
<222> LOCATION: (1)..(528)

<400> SEQUENCE: 11 atg ttg tgg att tgg aat gcc ctg atc gtg ttt gtc acc gtg gtc ggc     48
Met Leu Trp Ile Trp Asn Ala Leu Ile Val Phe Val Thr Val Val Gly
 1               5                  10                  15 atg gaa gtg gtt gct gca ctg gca cat aaa tac atc atg cac ggc tgg    96
Met Glu Val Val Ala Ala Leu Ala His Lys Tyr Ile Met His Gly Trp
                 20                  25                  30 ggt tgg ggc tgg cat ctt tca cat cat gaa ccg cgt aaa ggc gca ttt   144
Gly Trp Gly Trp His Leu Ser His His Glu Pro Arg Lys Gly Ala Phe
             35                  40                  45 gaa gtt aac gat ctc tat gcc gtg gta ttc gcc att gtg tcg att gcc   192
Glu Val Asn Asp Leu Tyr Ala Val Val Phe Ala Ile Val Ser Ile Ala
 50                  55                  60
```

```
ctg att tac ttc ggc agt aca gga atc tgg ccg ctc cag tgg att ggt       240
Leu Ile Tyr Phe Gly Ser Thr Gly Ile Trp Pro Leu Gln Trp Ile Gly
 65                  70                  75                  80 gca ggc atg acc gct tat ggt tta ctg tat ttt atg gtc cac gac gga       288
Ala Gly Met Thr Ala Tyr Gly Leu Leu Tyr Phe Met Val His Asp Gly
                 85                  90                  95 ctg gta cac cag cgc tgg ccg ttc cgc tac ata ccg cgc aaa ggc tac       336
Leu Val His Gln Arg Trp Pro Phe Arg Tyr Ile Pro Arg Lys Gly Tyr
             100                 105                 110 ctg aaa cgg tta tac atg gcc cac cgt atg cat cat gct gta agg gga       384
Leu Lys Arg Leu Tyr Met Ala His Arg Met His His Ala Val Arg Gly
         115                 120                 125 aaa gag ggc tgc gtg tcc ttt ggt ttt ctg tac gcg cca ccg tta tct       432
Lys Glu Gly Cys Val Ser Phe Gly Phe Leu Tyr Ala Pro Pro Leu Ser
     130                 135                 140 aaa ctt cag gcg acg ctg aga gaa agg cat gcg gct aga tcg ggc gct       480
Lys Leu Gln Ala Thr Leu Arg Glu Arg His Ala Ala Arg Ser Gly Ala
145                 150                 155                 160 gcc aga gat gag cag gac ggg gtg gat acg tct tca tcc ggg aag taa       528
Ala Arg Asp Glu Gln Asp Gly Val Asp Thr Ser Ser Ser Gly Lys
                 165                 170                 175

<210> SEQ ID NO 12
<211> LENGTH: 175
<212> TYPE: PRT
<213> ORGANISM: Pantoea stewartii

<400> SEQUENCE: 12

Met Leu Trp Ile Trp Asn Ala Leu Ile Val Phe Val Thr Val Val Gly
  1               5                  10                  15

Met Glu Val Val Ala Ala Leu Ala His Lys Tyr Ile Met His Gly Trp
                 20                  25                  30

Gly Trp Gly Trp His Leu Ser His His Glu Pro Arg Lys Gly Ala Phe
             35                  40                  45

Glu Val Asn Asp Leu Tyr Ala Val Phe Ala Ile Val Ser Ile Ala
         50                  55                  60

Leu Ile Tyr Phe Gly Ser Thr Gly Ile Trp Pro Leu Gln Trp Ile Gly
 65                  70                  75                  80

Ala Gly Met Thr Ala Tyr Gly Leu Leu Tyr Phe Met Val His Asp Gly
                 85                  90                  95

Leu Val His Gln Arg Trp Pro Phe Arg Tyr Ile Pro Arg Lys Gly Tyr
            100                 105                 110

Leu Lys Arg Leu Tyr Met Ala His Arg Met His His Ala Val Arg Gly
        115                 120                 125

Lys Glu Gly Cys Val Ser Phe Gly Phe Leu Tyr Ala Pro Pro Leu Ser
    130                 135                 140

Lys Leu Gln Ala Thr Leu Arg Glu Arg His Ala Ala Arg Ser Gly Ala
145                 150                 155                 160

Ala Arg Asp Glu Gln Asp Gly Val Asp Thr Ser Ser Ser Gly Lys
                165                 170                 175

<210> SEQ ID NO 13
<211> LENGTH: 25
<212> TYPE: DNA
<213> ORGANISM: artificial sequence
<220> FEATURE:
<223> OTHER INFORMATION: Primer

<400> SEQUENCE: 13
```

```
atgacggtct gcgcaaaaaa acacg                                              25
```

<210> SEQ ID NO 14
<211> LENGTH: 28
<212> TYPE: DNA
<213> ORGANISM: artificial sequence
<220> FEATURE:
<223> OTHER INFORMATION: Primer

<400> SEQUENCE: 14

```
gagaaattat gttgtggatt tggaatgc                                           28
```

<210> SEQ ID NO 15
<211> LENGTH: 19
<212> TYPE: DNA
<213> ORGANISM: artificial sequence
<220> FEATURE:
<223> OTHER INFORMATION: Primer

<400> SEQUENCE: 15

```
atgaaaccaa ctacggtaa                                                     19
```

<210> SEQ ID NO 16
<211> LENGTH: 19
<212> TYPE: DNA
<213> ORGANISM: artificial sequence
<220> FEATURE:
<223> OTHER INFORMATION: Primer

<400> SEQUENCE: 16

```
tcaaatcaga tcctccagc                                                     19
```

<210> SEQ ID NO 17
<211> LENGTH: 1479
<212> TYPE: DNA
<213> ORGANISM: artificial sequence
<220> FEATURE:
<223> OTHER INFORMATION: Mutant Variant crtI 514
<220> FEATURE:
<221> NAME/KEY: CDS
<222> LOCATION: (1)..(1479)

<400> SEQUENCE: 17

```
atg aaa cca act acg gta att ggt gcg ggc ttt ggt ggc ctg gca ctg         48
Met Lys Pro Thr Thr Val Ile Gly Ala Gly Phe Gly Gly Leu Ala Leu
1               5                   10                  15 gca att cgt tta cag gcc gca gga att cct gtt tcg ctg ctt gag cag         96
Ala Ile Arg Leu Gln Ala Ala Gly Ile Pro Val Ser Leu Leu Glu Gln
                20                  25                  30 cgc gac aag ccg ggt ggc cgg gct tat gtt tat cag gag cag ggc ttt        144
Arg Asp Lys Pro Gly Gly Arg Ala Tyr Val Tyr Gln Glu Gln Gly Phe
            35                  40                  45 act ttt gat gca ggc cct acc gtt atc acc gat ccc agc gcg att gaa        192
Thr Phe Asp Ala Gly Pro Thr Val Ile Thr Asp Pro Ser Ala Ile Glu
        50                  55                  60 gaa ctg ttt gct ctg gcc ggt aaa cag ctt aag gat tac gtc gag ctg        240
Glu Leu Phe Ala Leu Ala Gly Lys Gln Leu Lys Asp Tyr Val Glu Leu
65                  70                  75                  80 ttg ccg gtc tcg ccg ttt tat cgc ctg tgc tgg gag tcc ggc aag gtc        288
Leu Pro Val Ser Pro Phe Tyr Arg Leu Cys Trp Glu Ser Gly Lys Val
                85                  90                  95 ttc aat tac gat aac gac cag gcc cag tta gaa gcg cag ata cag cag        336
Phe Asn Tyr Asp Asn Asp Gln Ala Gln Leu Glu Ala Gln Ile Gln Gln
                100                 105                 110
```

-continued

| | | |
|---|---|---|
| ttt aat ccg cgc gat gtt gcg ggt tat cga gcg ttc ctt gac tat tcg<br>Phe Asn Pro Arg Asp Val Ala Gly Tyr Arg Ala Phe Leu Asp Tyr Ser<br>            115                    120                    125 | 384 |
| cgt gcc gta ttc aat gag ggc tat ctg gag ctc ggc act gtg cct ttt<br>Arg Ala Val Phe Asn Glu Gly Tyr Leu Glu Leu Gly Thr Val Pro Phe<br>130                    135                    140 | 432 |
| tta tcg ttc aaa gac atg ctt cgg gcc gcg ccc cag ttg gca aag ctg<br>Leu Ser Phe Lys Asp Met Leu Arg Ala Ala Pro Gln Leu Ala Lys Leu<br>145                    150                    155                    160 | 480 |
| cag gca tgg cgc agc gtt tac agt aaa gtt gcc ggc tac att gag gat<br>Gln Ala Trp Arg Ser Val Tyr Ser Lys Val Ala Gly Tyr Ile Glu Asp<br>            165                    170                    175 | 528 |
| gag cat ctt cgg cag gcg ttt tct ttt cac tcg ctc tta gtg ggg ggg<br>Glu His Leu Arg Gln Ala Phe Ser Phe His Ser Leu Leu Val Gly Gly<br>                  180                    185                    190 | 576 |
| aat ccg ttt gca acc tcg tcc att tat acg ctg att cac gcg tta gaa<br>Asn Pro Phe Ala Thr Ser Ser Ile Tyr Thr Leu Ile His Ala Leu Glu<br>            195                    200                    205 | 624 |
| cgg gaa tgg ggc gtc tgg ttt cca cgc ggt gga acc ggt gcg ctg gtc<br>Arg Glu Trp Gly Val Trp Phe Pro Arg Gly Gly Thr Gly Ala Leu Val<br>            210                    215                    220 | 672 |
| aat ggc atg atc aag ctg ttt cag gat ctg ggc ggc gaa gtc gtg ctt<br>Asn Gly Met Ile Lys Leu Phe Gln Asp Leu Gly Gly Glu Val Val Leu<br>225                    230                    235                    240 | 720 |
| aac gcc cgg gtc agt cat atg gaa acc gtt ggg gac aag att cag gcc<br>Asn Ala Arg Val Ser His Met Glu Thr Val Gly Asp Lys Ile Gln Ala<br>            245                    250                    255 | 768 |
| gtg cag ttg gaa gac ggc aga cgg ttt gaa acc tgc gcg gtg gcg tcg<br>Val Gln Leu Glu Asp Gly Arg Arg Phe Glu Thr Cys Ala Val Ala Ser<br>                  260                    265                    270 | 816 |
| aac gct gat gtt gta cat acc tat cgc gat ctg ctg tct cag cat ccc<br>Asn Ala Asp Val Val His Thr Tyr Arg Asp Leu Leu Ser Gln His Pro<br>            275                    280                    285 | 864 |
| gca gcc gct aag cag gcg aaa aaa ctg caa tcc aag cgt atg agt aac<br>Ala Ala Ala Lys Gln Ala Lys Lys Leu Gln Ser Lys Arg Met Ser Asn<br>290                    295                    300 | 912 |
| tca ctg ttt gta ctc tat ttt ggt ctc aac cat cat cac gat caa ctc<br>Ser Leu Phe Val Leu Tyr Phe Gly Leu Asn His His His Asp Gln Leu<br>305                    310                    315                    320 | 960 |
| gcc cat cat acc gtc tgt ttt ggg cca cgc tac cgt gaa ctg att cac<br>Ala His His Thr Val Cys Phe Gly Pro Arg Tyr Arg Glu Leu Ile His<br>            325                    330                    335 | 1008 |
| gaa att ttt aac cat gat ggt ctg gct gag gat ttt tcg ctt tat tta<br>Glu Ile Phe Asn His Asp Gly Leu Ala Glu Asp Phe Ser Leu Tyr Leu<br>                  340                    345                    350 | 1056 |
| cac gca cct tgt gtc acg gat ccg tca ctg gca ccg gaa ggg tgc ggc<br>His Ala Pro Cys Val Thr Asp Pro Ser Leu Ala Pro Glu Gly Cys Gly<br>            355                    360                    365 | 1104 |
| agc tat tat gtg ctg gcg cct gtt cca cac tta ggc acg gcg aac ctc<br>Ser Tyr Tyr Val Leu Ala Pro Val Pro His Leu Gly Thr Ala Asn Leu<br>            370                    375                    380 | 1152 |
| gac tgg gcg gta gaa gga ccc cga ctg cgc gat cgt att ttt gac tac<br>Asp Trp Ala Val Glu Gly Pro Arg Leu Arg Asp Arg Ile Phe Asp Tyr<br>385                    390                    395                    400 | 1200 |
| ctt gag caa cat tac atg cct ggc ttg cga agc cag ttg gtg acg cac<br>Leu Glu Gln His Tyr Met Pro Gly Leu Arg Ser Gln Leu Val Thr His<br>                  405                    410                    415 | 1248 |
| cgt atg ttt acg ccg ttc gat ttc cgc gac gag ctc aat gcc tgg caa<br>Arg Met Phe Thr Pro Phe Asp Phe Arg Asp Glu Leu Asn Ala Trp Gln<br>            420                    425                    430 | 1296 |

```
ggt tcg gcc ttc tcg gtt gaa cct att ctg acc cag agc gcc tgg ttc      1344
Gly Ser Ala Phe Ser Val Glu Pro Ile Leu Thr Gln Ser Ala Trp Phe
        435                 440                 445 cga cca cat aac cgc gat aag cac att gat aat ctc tat ctg gtt ggc      1392
Arg Pro His Asn Arg Asp Lys His Ile Asp Asn Leu Tyr Leu Val Gly
450                 455                 460 gca ggc acc cat cct ggc gcg ggc att ccc ggc gta atc ggc tcg gcg      1440
Ala Gly Thr His Pro Gly Ala Gly Ile Pro Gly Val Ile Gly Ser Ala
465                 470                 475                 480 aag gcg acg gca ggc tta atg ctg gag gat ctg att tga                  1479
Lys Ala Thr Ala Gly Leu Met Leu Glu Asp Leu Ile
                485                 490
```

<210> SEQ ID NO 18
<211> LENGTH: 492
<212> TYPE: PRT
<213> ORGANISM: artificial sequence
<220> FEATURE:
<223> OTHER INFORMATION: Synthetic Construct

<400> SEQUENCE: 18

```
Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Ser Leu Leu Glu Gln
            20                  25                  30

Arg Asp Lys Pro Gly Gly Arg Ala Tyr Val Tyr Gln Glu Gln Gly Phe
        35                  40                  45

Thr Phe Asp Ala Gly Pro Thr Val Ile Thr Asp Pro Ser Ala Ile Glu
    50                  55                  60

Glu Leu Phe Ala Leu Ala Gly Lys Gln Leu Lys Asp Tyr Val Glu Leu
65                  70                  75                  80

Leu Pro Val Ser Pro Phe Tyr Arg Leu Cys Trp Glu Ser Gly Lys Val
                85                  90                  95

Phe Asn Tyr Asp Asn Asp Gln Ala Gln Leu Glu Ala Gln Ile Gln Gln
            100                 105                 110

Phe Asn Pro Arg Asp Val Ala Gly Tyr Arg Ala Phe Leu Asp Tyr Ser
        115                 120                 125

Arg Ala Val Phe Asn Glu Gly Tyr Leu Glu Leu Gly Thr Val Pro Phe
    130                 135                 140

Leu Ser Phe Lys Asp Met Leu Arg Ala Ala Pro Gln Leu Ala Lys Leu
145                 150                 155                 160

Gln Ala Trp Arg Ser Val Tyr Ser Lys Val Ala Gly Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220

Asn Gly Met Ile Lys Leu Phe Gln Asp Leu Gly Gly Glu Val Val Leu
225                 230                 235                 240

Asn Ala Arg Val Ser His Met Glu Thr Val Gly Asp Lys Ile Gln Ala
                245                 250                 255

Val Gln Leu Glu Asp Gly Arg Arg Phe Glu Thr Cys Ala Val Ala Ser
            260                 265                 270

Asn Ala Asp Val Val His Thr Tyr Arg Asp Leu Leu Ser Gln His Pro
```

-continued

```
                275                 280                 285
Ala Ala Ala Lys Gln Ala Lys Lys Leu Gln Ser Lys Arg Met Ser Asn
            290                 295                 300

Ser Leu Phe Val Leu Tyr Phe Gly Leu Asn His His His Asp Gln Leu
305                 310                 315                 320

Ala His His Thr Val Cys Phe Gly Pro Arg Tyr Arg Glu Leu Ile His
                325                 330                 335

Glu Ile Phe Asn His Asp Gly Leu Ala Glu Asp Phe Ser Leu Tyr Leu
                340                 345                 350

His Ala Pro Cys Val Thr Asp Pro Ser Leu Ala Pro Glu Gly Cys Gly
            355                 360                 365

Ser Tyr Tyr Val Leu Ala Pro Val Pro His Leu Gly Thr Ala Asn Leu
370                 375                 380

Asp Trp Ala Val Glu Gly Pro Arg Leu Arg Asp Arg Ile Phe Asp Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Glu Leu Asn Ala Trp Gln
            420                 425                 430

Gly Ser Ala Phe Ser Val Glu Pro Ile Leu Thr Gln Ser Ala Trp Phe
        435                 440                 445

Arg Pro His Asn Arg Asp Lys His Ile Asp Asn Leu Tyr Leu Val Gly
    450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490

<210> SEQ ID NO 19
<211> LENGTH: 1479
<212> TYPE: DNA
<213> ORGANISM: Artificial sequence
<220> FEATURE:
<223> OTHER INFORMATION: Mutant variant crtI 515
<220> FEATURE:
<221> NAME/KEY: CDS
<222> LOCATION: (1)..(1479)

<400> SEQUENCE: 19 atg aaa cca act acg gta att ggt gcg ggc ttt ggt ggc ctg gca ctg      48
Met Lys Pro Thr Thr Val Ile Gly Ala Gly Phe Gly Gly Leu Ala Leu
1               5                   10                  15 gca att cgt tta cag gcc gca ggt att cct gtt ttg ctg ctt gag cag      96
Ala Ile Arg Leu Gln Ala Ala Gly Ile Pro Val Leu Leu Leu Glu Gln
            20                  25                  30 cgc gac aag ccg ggt ggc cgg gct tat gtt tat cag gag cag ggc ttt     144
Arg Asp Lys Pro Gly Gly Arg Ala Tyr Val Tyr Gln Glu Gln Gly Phe
        35                  40                  45 act ttt gat gca ggc cct acc gtt atc acc gat ccc agc gcg att gaa     192
Thr Phe Asp Ala Gly Pro Thr Val Ile Thr Asp Pro Ser Ala Ile Glu
    50                  55                  60 gaa ctg ttt gct ctg gcc ggt aaa cag ctt aag gat tac gtc gag ctg     240
Glu Leu Phe Ala Leu Ala Gly Lys Gln Leu Lys Asp Tyr Val Glu Leu
65                  70                  75                  80 atg ccg gtc acg ccg ttt tat cgc ctg tgc tgg gag tcc ggc aag gtc     288
Met Pro Val Thr Pro Phe Tyr Arg Leu Cys Trp Glu Ser Gly Lys Val
                85                  90                  95 ttc aat tac gat aac gac cag gcc cag tta gaa gcg cag ata cag cag     336
```

```
                         -continued

Phe Asn Tyr Asp Asn Asp Gln Ala Gln Leu Glu Ala Gln Ile Gln Gln
            100                 105                 110 ttt aat ccg cgc gac gtt gcg ggt tat cga gcg ttc ctt gac tat tcg     384
Phe Asn Pro Arg Asp Val Ala Gly Tyr Arg Ala Phe Leu Asp Tyr Ser
        115                 120                 125 cgt gcc gta ttc aat gag ggc tat ctg aag ctc ggc act gtg cct ttt     432
Arg Ala Val Phe Asn Glu Gly Tyr Leu Lys Leu Gly Thr Val Pro Phe
130                 135                 140 tta tcg ttc aaa gac atg ctt cgg gcc gcg ccc cag ttg gcg aag ctg     480
Leu Ser Phe Lys Asp Met Leu Arg Ala Ala Pro Gln Leu Ala Lys Leu
145                 150                 155                 160 cag gca tgg cgc agc gtt tac agt aaa gtt gcc ggc tac att gag gat     528
Gln Ala Trp Arg Ser Val Tyr Ser Lys Val Ala Gly Tyr Ile Glu Asp
                165                 170                 175 gag cat ctt cgg cag gcg ttt tct ttt cac tcg ctc tta gtg ggg ggg     576
Glu His Leu Arg Gln Ala Phe Ser Phe His Ser Leu Leu Val Gly Gly
            180                 185                 190 aat ccg ttt gca acc tcg tcc att tat acg ctg att cac gcg tta gaa     624
Asn Pro Phe Ala Thr Ser Ser Ile Tyr Thr Leu Ile His Ala Leu Glu
        195                 200                 205 cgg gaa tgg ggc gtc tgg ttt cca cgc ggt gga acc ggt gcg ctg gtc     672
Arg Glu Trp Gly Val Trp Phe Pro Arg Gly Gly Thr Gly Ala Leu Val
210                 215                 220 aat ggc atg atc aag ctg ttt caa gat ctg ggc ggc gaa gtc gtg ctt     720
Asn Gly Met Ile Lys Leu Phe Gln Asp Leu Gly Gly Glu Val Val Leu
225                 230                 235                 240 aac gcc cgg gtc agt cat atg gaa acc gtt ggg gac aag att cag gcc     768
Asn Ala Arg Val Ser His Met Glu Thr Val Gly Asp Lys Ile Gln Ala
                245                 250                 255 gtg cag ttg gaa gac ggc aga cgg ttt gaa acc tgc gcg gtg gcg tcg     816
Val Gln Leu Glu Asp Gly Arg Arg Phe Glu Thr Cys Ala Val Ala Ser
            260                 265                 270 aac gct gat gtt gta cat acc tat cgc gat ctg ctg tct cag cac ccc     864
Asn Ala Asp Val Val His Thr Tyr Arg Asp Leu Leu Ser Gln His Pro
        275                 280                 285 gca gcc gct aag cag gcg aaa aaa ctg caa tcc aag cgt atg agt aac     912
Ala Ala Ala Lys Gln Ala Lys Lys Leu Gln Ser Lys Arg Met Ser Asn
290                 295                 300 tca ctg ttt gta ctc tat ttt ggt ctc aac cat cac cac gat caa ctc     960
Ser Leu Phe Val Leu Tyr Phe Gly Leu Asn His His His Asp Gln Leu
305                 310                 315                 320 gcc cat cat acc gtc tgt ttt ggg cca cgc tac cgt gaa ctg att cac    1008
Ala His His Thr Val Cys Phe Gly Pro Arg Tyr Arg Glu Leu Ile His
                325                 330                 335 gaa att ttt aac cat gat ggt ctg gct gag gat ttt tcg ctt tat tta    1056
Glu Ile Phe Asn His Asp Gly Leu Ala Glu Asp Phe Ser Leu Tyr Leu
            340                 345                 350 cac gca cct tgt gtc acg gat ccg tca ctg gca ccg gaa ggg tgc ggc    1104
His Ala Pro Cys Val Thr Asp Pro Ser Leu Ala Pro Glu Gly Cys Gly
        355                 360                 365 agc tat tat gtg ctg gcg cct gtt cca cac tta ggc acg gcg aac ctc    1152
Ser Tyr Tyr Val Leu Ala Pro Val Pro His Leu Gly Thr Ala Asn Leu
370                 375                 380 gac tgg gcg gta gaa gga ccc cga ctg cgc gat cgt att ttt gac tac    1200
Asp Trp Ala Val Glu Gly Pro Arg Leu Arg Asp Arg Ile Phe Asp Tyr
385                 390                 395                 400 ctt gag caa cat tac atg cct ggc ttg cga agc cag ttg gtg acg cac    1248
Leu Glu Gln His Tyr Met Pro Gly Leu Arg Ser Gln Leu Val Thr His
                405                 410                 415
```

```
cgt atg ttt acg ccg ttc gat ttc cgc gac gag ctc aat gcc tgg caa    1296
Arg Met Phe Thr Pro Phe Asp Phe Arg Asp Glu Leu Asn Ala Trp Gln
        420                 425                 430 ggt tcg gcc ttc tcg gtt gaa cct att ctg acc cag agc gcc tgg ttc    1344
Gly Ser Ala Phe Ser Val Glu Pro Ile Leu Thr Gln Ser Ala Trp Phe
        435                 440                 445 cga cca cat aac cgc gat aag cac att gat aat ctt tat ctg gtt ggc    1392
Arg Pro His Asn Arg Asp Lys His Ile Asp Asn Leu Tyr Leu Val Gly
450                 455                 460 gca ggc acc cat cct ggc gcg ggc att ccc ggc gta atc ggc tcg gcg    1440
Ala Gly Thr His Pro Gly Ala Gly Ile Pro Gly Val Ile Gly Ser Ala
465                 470                 475                 480 aag gcg acg gca ggc tta atg ctg gag gat ctg att tga                1479
Lys Ala Thr Ala Gly Leu Met Leu Glu Asp Leu Ile
                485                 490
```

<210> SEQ ID NO 20
<211> LENGTH: 492
<212> TYPE: PRT
<213> ORGANISM: Artificial sequence
<220> FEATURE:
<223> OTHER INFORMATION: Synthetic Construct

<400> SEQUENCE: 20

```
Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
            20                  25                  30

Arg Asp Lys Pro Gly Gly Arg Ala Tyr Val Tyr Gln Glu Gln Gly Phe
        35                  40                  45

Thr Phe Asp Ala Gly Pro Thr Val Ile Thr Asp Pro Ser Ala Ile Glu
    50                  55                  60

Glu Leu Phe Ala Leu Ala Gly Lys Gln Leu Lys Asp Tyr Val Glu Leu
65                  70                  75                  80

Met Pro Val Thr Pro Phe Tyr Arg Leu Cys Trp Glu Ser Gly Lys Val
                85                  90                  95

Phe Asn Tyr Asp Asn Asp Gln Ala Gln Leu Glu Ala Gln Ile Gln Gln
            100                 105                 110

Phe Asn Pro Arg Asp Val Ala Gly Tyr Arg Ala Phe Leu Asp Tyr Ser
        115                 120                 125

Arg Ala Val Phe Asn Glu Gly Tyr Leu Lys Leu Gly Thr Val Pro Phe
    130                 135                 140

Leu Ser Phe Lys Asp Met Leu Arg Ala Ala Pro Gln Leu Ala Lys Leu
145                 150                 155                 160

Gln Ala Trp Arg Ser Val Tyr Ser Lys Val Ala Gly Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220

Asn Gly Met Ile Lys Leu Phe Gln Asp Leu Gly Gly Glu Val Val Leu
225                 230                 235                 240

Asn Ala Arg Val Ser His Met Glu Thr Val Gly Asp Lys Ile Gln Ala
                245                 250                 255

Val Gln Leu Glu Asp Gly Arg Arg Phe Glu Thr Cys Ala Val Ala Ser
```

-continued

```
                    260                 265                 270
Asn Ala Asp Val Val His Thr Tyr Arg Asp Leu Leu Ser Gln His Pro
                275                 280                 285
Ala Ala Ala Lys Gln Ala Lys Lys Leu Gln Ser Lys Arg Met Ser Asn
            290                 295                 300
Ser Leu Phe Val Leu Tyr Phe Gly Leu Asn His His Asp Gln Leu
305                 310                 315                 320
Ala His His Thr Val Cys Phe Gly Pro Arg Tyr Arg Glu Leu Ile His
                325                 330                 335
Glu Ile Phe Asn His Asp Gly Leu Ala Glu Asp Phe Ser Leu Tyr Leu
                340                 345                 350
His Ala Pro Cys Val Thr Asp Pro Ser Leu Ala Pro Glu Gly Cys Gly
                355                 360                 365
Ser Tyr Tyr Val Leu Ala Pro Val Pro His Leu Gly Thr Ala Asn Leu
            370                 375                 380
Asp Trp Ala Val Glu Gly Pro Arg Leu Arg Asp Arg Ile Phe Asp Tyr
385                 390                 395                 400
Leu Glu Gln His Tyr Met Pro Gly Leu Arg Ser Gln Leu Val Thr His
                405                 410                 415
Arg Met Phe Thr Pro Phe Asp Phe Arg Asp Glu Leu Asn Ala Trp Gln
                420                 425                 430
Gly Ser Ala Phe Ser Val Glu Pro Ile Leu Thr Gln Ser Ala Trp Phe
            435                 440                 445
Arg Pro His Asn Arg Asp Lys His Ile Asp Asn Leu Tyr Leu Val Gly
            450                 455                 460
Ala Gly Thr His Pro Gly Ala Gly Ile Pro Gly Val Ile Gly Ser Ala
465                 470                 475                 480
Lys Ala Thr Ala Gly Leu Met Leu Glu Asp Leu Ile
                485                 490

<210> SEQ ID NO 21
<211> LENGTH: 61
<212> TYPE: DNA
<213> ORGANISM: artificial sequence
<220> FEATURE:
<223> OTHER INFORMATION: Primer

<400> SEQUENCE: 21
tggaagcgct agcggactac atcatccagc gtaataaata acgtcttgag cgattgtgta      60
g                                                                      61

<210> SEQ ID NO 22
<211> LENGTH: 65
<212> TYPE: DNA
<213> ORGANISM: artificial sequence
<220> FEATURE:
<223> OTHER INFORMATION: Primer

<400> SEQUENCE: 22
tctgatgcgc aagctgaaga aaaatgagca tggagaataa tatgacgtct tgagcgattg      60
tgtag                                                                  65

<210> SEQ ID NO 23
<211> LENGTH: 65
<212> TYPE: DNA
<213> ORGANISM: artificial sequence
<220> FEATURE:
<223> OTHER INFORMATION: Primer
```

<400> SEQUENCE: 23
gacgcgtcga agcgcgcaca gtctgcgggg caaaacaatc gataacgtct tgagcgattg    60
tgtag                                                                65

<210> SEQ ID NO 24
<211> LENGTH: 60
<212> TYPE: DNA
<213> ORGANISM: artificial sequence
<220> FEATURE:
<223> OTHER INFORMATION: Primer

<400> SEQUENCE: 24
accatgacgg ggcgaaaaat attgagagtc agacattcat gtgtaggctg gagctgcttc    60

<210> SEQ ID NO 25
<211> LENGTH: 64
<212> TYPE: DNA
<213> ORGANISM: artificial sequence
<220> FEATURE:
<223> OTHER INFORMATION: Primer

<400> SEQUENCE: 25
gaagacgaaa gggcctcgtg atacgcctat ttttataggt tatatgaata tcctccttag    60
ttcc                                                                 64

<210> SEQ ID NO 26
<211> LENGTH: 50
<212> TYPE: DNA
<213> ORGANISM: artificial sequence
<220> FEATURE:
<223> OTHER INFORMATION: Primer

<400> SEQUENCE: 26
ctaaggagga tattcatata acctataaaa ataggcgtat cacgaggccc                50

<210> SEQ ID NO 27
<211> LENGTH: 70
<212> TYPE: DNA
<213> ORGANISM: artificial sequence
<220> FEATURE:
<223> OTHER INFORMATION: Primer

<400> SEQUENCE: 27
ggagtcgacc agtgccaggg tcgggtattt ggcaatatca aaactcatag ttaatttctc    60
ctctttaatg                                                           70

<210> SEQ ID NO 28
<211> LENGTH: 68
<212> TYPE: DNA
<213> ORGANISM: artificial sequence
<220> FEATURE:
<223> OTHER INFORMATION: Primer

<400> SEQUENCE: 28
tgggaactcc ctgtgcattc aataaaatga cgtgttccgt ttgcatagtt aatttctcct    60
ctttaatg                                                             68

<210> SEQ ID NO 29
<211> LENGTH: 68
<212> TYPE: DNA
<213> ORGANISM: artificial sequence
<220> FEATURE:

```
<223> OTHER INFORMATION: Primer

<400> SEQUENCE: 29
cggccgccgg aaccacggcg caaacatcca aatgagtggt tgccatagtt aatttctcct        60
ctttaatg                                                                  68

<210> SEQ ID NO 30
<211> LENGTH: 62
<212> TYPE: DNA
<213> ORGANISM: artificial sequence
<220> FEATURE:
<223> OTHER INFORMATION: Primer

<400> SEQUENCE: 30
cctgcttaac gcaggcttcg agttgctgcg gaaagtccat agttaatttc tcctctttaa        60
tg                                                                        62

<210> SEQ ID NO 31
<211> LENGTH: 25
<212> TYPE: DNA
<213> ORGANISM: artificial sequence
<220> FEATURE:
<223> OTHER INFORMATION: Primer

<400> SEQUENCE: 31
accggatatc accacttatc tgctc                                               25

<210> SEQ ID NO 32
<211> LENGTH: 26
<212> TYPE: DNA
<213> ORGANISM: artificial sequence
<220> FEATURE:
<223> OTHER INFORMATION: Primer

<400> SEQUENCE: 32
tggcaacagt cgtagctcct gggtgg                                              26

<210> SEQ ID NO 33
<211> LENGTH: 32
<212> TYPE: DNA
<213> ORGANISM: artificial sequence
<220> FEATURE:
<223> OTHER INFORMATION: Primer

<400> SEQUENCE: 33
taacctataa aaataggcgt atcacgaggc cc                                       32

<210> SEQ ID NO 34
<211> LENGTH: 25
<212> TYPE: DNA
<213> ORGANISM: artificial sequence
<220> FEATURE:
<223> OTHER INFORMATION: Primer

<400> SEQUENCE: 34
cagccaactg gagaacgcga gatgt                                               25

<210> SEQ ID NO 35
<211> LENGTH: 25
<212> TYPE: DNA
<213> ORGANISM: artificial sequence
<220> FEATURE:
<223> OTHER INFORMATION: Primer

<400> SEQUENCE: 35
```

```
ccagcagcgc atgcaccgag tgttc                                    25
```

<210> SEQ ID NO 36
<211> LENGTH: 65
<212> TYPE: DNA
<213> ORGANISM: artificial sequence
<220> FEATURE:
<223> OTHER INFORMATION: Primer
<400> SEQUENCE: 36

```
agccgtcgca ggaggaacaa ctcatatcat cattgcgatc tcgaccgtct tgagcgattg    60
tgtag                                                              65
```

<210> SEQ ID NO 37
<211> LENGTH: 51
<212> TYPE: DNA
<213> ORGANISM: artificial sequence
<220> FEATURE:
<223> OTHER INFORMATION: Primer
<400> SEQUENCE: 37

```
tgaacgtgtt ttttgcgca gaccgtcata gttaatttct cctctttaat g             51
```

<210> SEQ ID NO 38
<211> LENGTH: 55
<212> TYPE: DNA
<213> ORGANISM: artificial sequence
<220> FEATURE:
<223> OTHER INFORMATION: Primer
<400> SEQUENCE: 38

```
acagaattca ttaaagagga gaaattaact atgacggtct gcgcaaaaaa acacg        55
```

<210> SEQ ID NO 39
<211> LENGTH: 65
<212> TYPE: DNA
<213> ORGANISM: artificial sequence
<220> FEATURE:
<223> OTHER INFORMATION: Primer
<400> SEQUENCE: 39

```
agaatgacca gctggatgca ttatctttat ttggatcatt gagggttaac tgacggcagc   60
gagtt                                                              65
```

<210> SEQ ID NO 40
<211> LENGTH: 26
<212> TYPE: DNA
<213> ORGANISM: artificial sequence
<220> FEATURE:
<223> OTHER INFORMATION: Primer
<400> SEQUENCE: 40

```
ccatgaccct acattgtgat ctatag                                       26
```

<210> SEQ ID NO 41
<211> LENGTH: 25
<212> TYPE: DNA
<213> ORGANISM: artificial sequence
<220> FEATURE:
<223> OTHER INFORMATION: Primer
<400> SEQUENCE: 41

```
ggaaccattg aactggaccc taacg                                        25
```

<210> SEQ ID NO 42
<211> LENGTH: 56
<212> TYPE: DNA
<213> ORGANISM: artificial sequence
<220> FEATURE:
<223> OTHER INFORMATION: Primer

<400> SEQUENCE: 42
tcctccagca ttaagcctgc cgtcgccttt taactgacgg cagcgagttt tttgtc       56

<210> SEQ ID NO 43
<211> LENGTH: 54
<212> TYPE: DNA
<213> ORGANISM: artificial sequence
<220> FEATURE:
<223> OTHER INFORMATION: Primer

<400> SEQUENCE: 43
tttgacaaaa aactcgctgc cgtcagttaa aaggcgacgg caggcttaat gctg         54

<210> SEQ ID NO 44
<211> LENGTH: 65
<212> TYPE: DNA
<213> ORGANISM: artificial sequence
<220> FEATURE:
<223> OTHER INFORMATION: Primer

<400> SEQUENCE: 44
agaatgacca gctggatgca ttatctttat ttggatcatt gagggctaga tcgggcgctg   60
ccaga                                                               65

<210> SEQ ID NO 45
<211> LENGTH: 20
<212> TYPE: DNA
<213> ORGANISM: artificial sequence
<220> FEATURE:
<223> OTHER INFORMATION: Primer

<400> SEQUENCE: 45
cagtcatagc cgaatagcct                                               20

<210> SEQ ID NO 46
<211> LENGTH: 20
<212> TYPE: DNA
<213> ORGANISM: artificial sequence
<220> FEATURE:
<223> OTHER INFORMATION: Primer

<400> SEQUENCE: 46
cggtgccctg aatgaactgc                                               20

<210> SEQ ID NO 47
<211> LENGTH: 25
<212> TYPE: DNA
<213> ORGANISM: artificial sequence
<220> FEATURE:
<223> OTHER INFORMATION: Primer

<400> SEQUENCE: 47
ctagatcggg cgctgccaga gatga                                         25

<210> SEQ ID NO 48
<211> LENGTH: 25
<212> TYPE: DNA
<213> ORGANISM: artificial sequence -continued
<220> FEATURE:
<223> OTHER INFORMATION: Primer

<400> SEQUENCE: 48
acacgttcac cttactggca tttcg                                25

<210> SEQ ID NO 49
<211> LENGTH: 8609
<212> TYPE: DNA
<213> ORGANISM: artificial sequence
<220> FEATURE:
<223> OTHER INFORMATION: Plasmid pPCB15

<400> SEQUENCE: 49

```
cgtatggcaa tgaaagacgg tgagctggtg atatgggata gtgttcaccc ttgttacacc      60
gttttccatg agcaaactga aacgttttca tcgctctgga gtgaatacca cgacgatttc     120
cggcagtttc tacacatata ttcgcaagat gtggcgtgtt acggtgaaaa cctggcctat     180
ttccctaaag ggtttattga atatgtttt tcgtctcag ccaatccctg ggtgagtttc      240
accagttttg atttaaacgt ggccaatatg acaacttct tcgccccgt tttcaccatg       300
ggcaaatatt atacgcaagg cgacaaggtg ctgatgccgc tggcgattca ggttcatcat    360
gccgtctgtg atggcttcca tgtcggcaga atgcttaatg aattacaaca gtactgcgat    420
gagtggcagg gcgggcgta atttttttaa ggcagttatt ggtgcctaga aatatttat     480
ctgattaata agatgatctt cttgagatcg ttttggtctg cgcgtaatct cttgctctga    540
aaacgaaaaa accgccttgc agggcggttt ttcgaaggtt ctctgagcta ccaactcttt    600
gaaccgaggt aactggcttg gaggagcgca gtcaccaaaa cttgtccttt cagtttagcc    660
ttaaccggcg catgacttca agactaactc ctctaaatca attaccagtg gctgctgcca    720
gtggtgcttt tgcatgtctt tccgggttgg actcaagacg atagttaccg gataaggcgc    780
agcggtcgga ctgaacgggg ggttcgtgca tacagtccag cttggagcga actgcctacc    840
cggaactgag tgtcaggcgt ggaatgagac aaacgcggcc ataacagcgg aatgacaccg    900
gtaaaccgaa aggcaggaac aggagagcgc acgagggagc cgccagggga aacgcctggt    960
atctttatag tcctgtcggg tttcgccacc actgatttga gcgtcagatt tcgtgatgct   1020
tgtcaggggg gcggagccta tggaaaaacg gctttgccgc ggccctctca cttccctgtt   1080
aagtatcttc ctggcatctt ccaggaaatc tccgccccgt tcgtaagcca tttccgctcg   1140
ccgcagtcga acgaccgagc gtagcgagtc agtgagcgag gaagcggaat atatcctgta   1200
tcacatattc tgctgacgca ccggtgcagc cttttttctc ctgccacatg aagcacttca   1260
ctgacaccct catcagtgcc aacatagtaa gccagtatat acactccgct agcgcccaat   1320
acgcaaaccg cctctccccg cgcgttggcc gattcattaa tgcagctggc acgacaggtt   1380
tcccgactgg aaagcgggca gtgagcgcaa cgcaattaat gtgagttagc tcactcatta   1440
ggcaccccag gctttacact ttatgcttcc ggctcgtatg ttgtgtggaa ttgtgagcgg   1500
ataacaattt cacacaggaa acagctatga ccatgattac gaattcgagc tcggtaccca   1560
aacgaattcg ccttttgac ggtctgcgca aaaaaacacg ttcaccttac tggcatttcg   1620
gctgagcagt tgctggctga tatcgatagc cgccttgatc agttactgcc ggttcagggt   1680
gagcgggatt gtgtgggtgc cgcgatgcgt gaaggcacgc tggcaccggg caaacgtatt   1740
cgtccgatgc tgctgttatt aacagcgcgc gatcttggct gtgcgatcag tcacggggga   1800
ttactggatt tagcctgcgc ggttgaaatg gtgcatgctg cctcgctgat tctggatgat   1860
```

-continued

```
atgccctgca tggacgatgc gcagatgcgt cgggggcgtc ccaccattca cacgcagtac    1920
ggtgaacatg tggcgattct ggcggcggtc gctttactca gcaaagcgtt tggggtgatt    1980
gccgaggctg aaggtctgac gccgatagcc aaaactcgcg cggtgtcgga gctgtccact    2040
gcgattggca tgcagggtct ggttcagggc cagtttaagg acctctcgga aggcgataaa    2100
ccccgcagcg ccgatgccat actgctaacc aatcagttta aaccagcac gctgttttgc     2160 gcgtcaacgc aaatggcgtc cattgcggcc aacgcgtcct gcgaagcgcg tgagaacctg    2220
catcgtttct cgctcgatct cggccaggcc tttcagttgc ttgacgatct taccgatggc    2280
atgaccgata ccggcaaaga catcaatcag gatgcaggta aatcaacgct ggtcaattta    2340
ttaggctcag gcgcggtcga agaacgcctg cgacagcatt tgcgcctggc cagtgaacac    2400
ctttccgcgg catgccaaaa cggccattcc accacccaac tttttattca ggcctggttt    2460
gacaaaaaac tcgctgccgt cagttaagga tgctgcatga ccattttgc ggtgatcgca     2520 ccgcccttt tcagccatgt tcgcgctctg caaaaccttg ctcaggaatt agtggcccgc     2580
ggtcatcgtg ttacgttttt tcagcaacat gactgcaaag cgctggtaac gggcagcgat    2640
atcggattcc agaccgtcgg actgcaaacg catcctcccg gttccttatc gcacctgctg    2700
cacctggccg cgcacccact cggaccctcg atgttacgac tgatcaatga atggcacgt     2760 accagcgata tgctttgccg ggaactgccc gccgcttttc atgcgttgca gatagagggc    2820
gtgatcgttg atcaaatgga gccggcaggt gcagtagtcg cagaagcgtc aggtctgccg    2880
tttgtttcgg tggcctgcgc gctgccgctc aaccgcgaac cgggtttgcc tctggcggtg    2940
atgcctttcg agtacggcac cagcgatgcg gctcgggaac gctataccac cagcgaaaaa    3000
atttatgact ggctgatgcg acgtcacgat cgtgtgatcg cgcatcatgc atgcagaatg    3060
ggtttagccc cgcgtgaaaa actgcatcat tgttttctc cactggcaca aatcagccag     3120
ttgatccccg aactggattt tccccgcaaa gcgctgccag actgctttca tgcggttgga    3180
ccgttacggc aaccccaggg gacgccgggg tcatcaactt cttatttcc gtccccggac     3240 aaacccgta tttttgcctc gctgggcacc ctgcagggac atcgttatgg cctgttcagg     3300
accatcgcca aagcctgcga agaggtggat gcgcagttac tgttggcaca ctgtggcggc    3360
ctctcagcca cgcaggcagg tgaactggcc cggggcgggg acattcaggt tgtggatttt    3420
gccgatcaat ccgcagcact tcacaggca cagttgacaa tcacacatgg tgggatgaat     3480
acggtactgg acgctattgc ttcccgcaca ccgctactgg cgctgccgct ggcatttgat    3540
caacctggcg tggcatcacg aattgtttat catggcatcg gcaagcgtgc gtctcggttt    3600
actaccagcc atgcgctggc gcggcagatt cgatcgctgc tgactaacac cgattacccg    3660
cagcgtatga caaaaattca ggccgcattg cgtctgcag gcggcacacc agccgccgcc     3720
gatattgttg aacaggcgat gcggacctgt cagccagtac tcagtgggca ggattatgca    3780
accgcactat gatctcattc tggtcggtgc cggtctggct aatggcctta tcgcgctccg    3840
gcttcagcaa cagcatccgg atatgcggat cttgcttatt gaggcgggtc ctgaggcggg    3900
agggaaccat acctggtcct tcacgaaga ggatttaacg ctgaatcagc atcgctggat     3960
agcgccgctt gtggtccatc actggcccga ctaccaggtt cgtttccccc aacgccgtcg    4020
ccatgtgaac agtggctact actgcgtgac ctcccggcat ttcgccggga tactccggca    4080
acagtttgga caacatttat ggctgcatac cgcggtttca gccgttcatg ctgaatcggt    4140
ccagttagcg gatggccgga ttattcatgc cagtacagtg atcgacggac ggggttacac    4200
gcctgattct gcactacgcg taggattcca ggcatttatc ggtcaggagt ggcaactgag    4260
```

-continued

```
cgcgccgcat ggtttatcgt caccgattat catggatgcg acggtcgatc agcaaaatgg   4320
ctaccgcttt gtttataccc tgccgctttc cgcaaccgca ctgctgatcg aagacacaca   4380
ctacattgac aaggctaatc ttcaggccga acgggcgcgt cagaacattc gcgattatgc   4440
tgcgcgacag ggttggccgt tacagacgtt gctgcgggaa gaacagggtg cattgcccat   4500
tacgttaacg ggcgataatc gtcagttttg gcaacagcaa ccgcaagcct gtagcggatt   4560
acgcgccggg ctgtttcatc cgacaaccgg ctactcccta ccgctcgcgg tggcgctggc   4620
cgatcgtctc agcgcgctgg atgtgtttac ctcttcctct gttcaccaga cgattgctca   4680
cttttcccag caacgttggc agcaacaggg gttttttccgc atgctgaatc gcatgttgtt   4740
tttagccgga ccgccgagt cacgctggcg tgtgatgcag cgtttctatg cttacccga    4800 ggatttgatt gcccgctttt atgcgggaaa actcaccgtg accgatcggc tacgcattct   4860
gagcggcaag ccgcccgttc ccgttttcgc ggcattgcag gcaattatga cgactcatcg   4920
ttgaagagcg actacatgaa accaactacg gtaattggtg cgggctttgg tggcctggca   4980
ctggcaattc gtttacaggc cgcaggtatt cctgttttgc tgcttgagca gcgcgacaag   5040
ccgggtggcc gggcttatgt ttatcaggag cagggcttta cttttgatgc aggccctacc   5100
gttatcaccg atcccagcgc gattgaagaa ctgtttgctc tggccggtaa acagcttaag   5160
gattacgtcg agctgttgcc ggtcacgccg ttttatcgcc tgtgctggga gtccggcaag   5220
gtcttcaatt acgataacga ccaggcccag ttagaagcgc agatacagca gtttaatccg   5280
cgcgatgttg cgggttatcg agcgttcctt gactattcgc gtgccgtatt caatgagggc   5340
tatctgaagc tcggcactgt gcctttttta tcgttcaaag acatgcttcg ggccgcgccc   5400
cagttggcaa agctgcaggc atggcgcagc gtttacagta agttgccgg ctacattgag   5460 gatgagcatc ttcggcaggc gttttctttt cactcgctct tagtgggggg gaatccgttt   5520
gcaacctcgt ccattatac gctgattcac gcgttagaac gggaatgggg cgtctggttt   5580
ccacgcggtg gaaccggtgc gctggtcaat ggcatgatca agctgtttca ggatctgggc   5640
ggcgaagtcg tgcttaacgc ccgggtcagt catatgaaa ccgttgggga caagattcag   5700
gccgtgcagt tggaagacgg cagacggttt gaaacctgcg cggtggcgtc gaacgctgat   5760
gttgtacata cctatcgcga tctgctgtct cagcatcccg cagccgctaa gcaggcgaaa   5820
aaactgcaat ccaagcgtat gagtaactca ctgtttgtac tctatttgg tctcaaccat   5880 catcacgatc aactcgccca tcataccgtc tgttttgggc cacgctaccg tgaactgatt   5940
cacgaaattt ttaaccatga tggtctggct gaggattttt cgctttattt acacgcacct   6000
tgtgtcacgg atccgtcact ggcaccggaa gggtgcggca gctattatgt gctggcgcct   6060
gttccacact taggcacggc gaacctcgac tgggcggtag aaggacccg actgcgcgat   6120 cgtatttttg actaccttga gcaacattac atgcctggct gcgaagcca gttggtgacg   6180 caccgtatgt ttacgccgtt cgatttccgc gacgagctca atgcctggca aggttcggcc   6240
ttctcggttg aacctattct gacccagagc gcctggttcc gaccacataa ccgcgataag   6300
cacattgata atctttatct ggttggcgca ggcacccatc ctggcgcggg cattcccggc   6360
gtaatcggct cggcgaaggc gacggcaggc ttaatgctgg aggacctgat ttgacgaata   6420
cgtcattact gaatcatgcc gtcgaaacca tggcggttgg ctcgaaaagc tttgcgactg   6480
catcgacgct tttcgacgcc aaacccgtc gcagcgtgct gatgctttac gcatggtgcc   6540
gccactgcga cgacgtcatt gacgatcaaa cactgggctt tcatgccgac cagccctctt   6600
```

-continued

```
cgcagatgcc tgagcagcgc ctgcagcagc ttgaaatgaa aacgcgtcag gcctacgccg      6660
gttcgcaaat gcacgagccc gcttttgccg cgtttcagga ggtcgcgatg gcgcatgata      6720
tcgctcccgc ctacgcgttc gaccatctgg aaggttttgc catggatgtg cgcgaaacgc      6780
gctacctgac actggacgat acgctgcgtt attgctatca cgtcgccggt gttgtgggcc      6840
tgatgatggc gcaaattatg ggcgttcgcg ataacgccac gctcgatcgc gcctgcgatc      6900
tcgggctggc tttccagttg accaacattg cgcgtgatat tgtcgacgat gctcaggtgg      6960
gccgctgtta tctgcctgaa agctggctgg aagaggaagg actgacgaaa gcgaattatg      7020
ctgcgccaga aaaccggcag gccttaagcc gtatcgccgg cgactggta cgggaagcgg      7080 aaccctatta cgtatcatca atggccggtc tggcacaatt acccttacgc tcggcctggg      7140
ccatcgcgac agcgaagcag gtgtaccgta aaattggcgt gaaagttgaa caggccggta      7200
agcaggcctg ggatcatcgc cagtccacgt ccaccgccga aaaattaacg cttttgctga      7260
cggcatccgg tcaggcagtt acttcccgga tgaagacgta tccacccgcgt cctgctcatc      7320 tctggcagcg cccgatctag ccgcatgcct ttctctcagc gtcgcctgaa gtttagataa      7380
cggtggcgcg tacagaaaac caaaggacac gcagccctct tttcccctta cagcatgatg      7440
catacggtgg gccatgtata accgtttcag gtagcctttg cgcggtatgt agcggaacgg      7500
ccagcgctgt tgtaccagtc cgtcgtggac cataaaatac agtaaaccat aagcggtcat      7560
gcctgcacca atccactgga gcggccagat tcctgtactg ccgaagtaaa tcagggcaat      7620
cgacacaatg gcgaatacca cggcatagag atcgttaact tcaaatgcgc ctttacgcgg      7680
ttcatgatgt gaaagatgcc agccccaacc ccagccgtgc atgatgtatt tatgtgccag      7740
tgcagcaacc acttccatgc cgaccacggt gacaaacacg atcagggcat tccaaatcca      7800
caacataatt tctcaagggc gaattcgcgg ggatcctcta gagtcgacct gcaggcatgc      7860
aagcttggca ctggccgtcg ttttacaacg tcgtgactgg gaaaaccctg gcgttaccca      7920
acttaatcgc cttgcagcac atccccctttt cgccagctgg cgtaatagcg aagaggcccg      7980
caccgatcgc ccttcccaac agttgcgcag cctgaatggc gaatggcgct gatgtccggc      8040
ggtgcttttg ccgttacgca ccaccccgtc agtagctgaa caggagggac agctgataga      8100
aacagaagcc actggagcac ctcaaaaaca ccatcataca ctaaatcagt aagttggcag      8160
catcacccga cgcactttgc gccgaataaa tacctgtgac ggaagatcac ttcgcagaat      8220
aaataaatcc tggtgtccct gttgataccg ggaagccctg ggccaacttt tggcgaaaat      8280
gagacgttga tcggcacgta agaggttcca actttcacca taatgaaata agatcactac      8340
cgggcgtatt ttttgagtta tcgagatttt caggagctaa ggaagctaaa atggagaaaa      8400
aaatcactgg atataccacc gttgatatat cccaatggca tcgtaaagaa cattttgagg      8460
catttcagtc agttgctcaa tgtacctata accagaccgt tcagctggat attacggcct      8520
ttttaaagac cgtaaagaaa aataagcaca gttttatcc ggcctttatt cacattcttg      8580
cccgcctgat gaatgctcat ccggaattt                                        8609
```

<210> SEQ ID NO 50
<211> LENGTH: 6329
<212> TYPE: DNA
<213> ORGANISM: artificial sequence
<220> FEATURE:
<223> OTHER INFORMATION: Plasmid pKD46

<400> SEQUENCE: 50

```
catcgattta ttatgacaac ttgacggcta catcattcac ttttcttca caaccggcac        60
```

```
ggaactcgct cgggctggcc ccggtgcatt ttttaaatac ccgcgagaaa tagagttgat    120
cgtcaaaacc aacattgcga ccgacggtgg cgataggcat ccgggtggtg ctcaaaagca    180
gcttcgcctg gctgatacgt tggtcctcgc gccagcttaa gacgctaatc cctaactgct    240
ggcggaaaag atgtgacaga cgcgacggcg acaagcaaac atgctgtgcg acgctggcga    300
tatcaaaatt gctgtctgcc aggtgatcgc tgatgtactg acaagcctcg cgtacccgat    360
tatccatcgg tggatggagc gactcgttaa tcgcttccat gcgccgcagt aacaattgct    420
caagcagatt tatcgccagc agctccgaat agcgcccttc cccttgcccg gcgttaatga    480
tttgcccaaa caggtcgctg aaatgcggct ggtgcgcttc atccgggcga agaaccccg     540 tattggcaaa tattgacggc cagttaagcc attcatgcca gtaggcgcgc ggacgaaagt    600
aaacccactg gtgataccat cgcgagcct ccggatgacg accgtagtga tgaatctctc     660
ctggcgggaa cagcaaaata tcacccggtc ggcaaacaaa ttctcgtccc tgatttttca    720
ccaccccctg accgcgaatg gtgagattga gaatataacc tttcattccc agcggtcggt    780
cgataaaaaa atcgagataa ccgttggcct caatcggcgt taaacccgcc accagatggg    840
cattaaacga gtatcccggc agcaggggat catttttgcgc ttcagccata cttttcatac    900
tcccgccatt cagagaagaa accaattgtc catattgcat cagacattgc cgtcactgcg    960
tcttttactg gctcttctcg ctaaccaaac cggtaacccc gcttattaaa agcattctgt   1020
aacaaagcgg gaccaaagcc atgacaaaaa cgcgtaacaa agtgtctat aatcacggca    1080 gaaaagtcca cattgattat ttgcacggcg tcacactttg ctatgccata gcattttttat   1140 ccataagatt agcggatcct acctgacgct ttttatcgca actctctact gtttctccat   1200
acccgttttt ttgggaattc gagctctaag gaggttataa aaaatggata ttaatactga   1260
aactgagatc aagcaaaagc attcactaac ccccttttcct gttttcctaa tcagcccggc   1320
atttcgcggg cgatatttc acagctattt caggagttca gccatgaacg cttattacat    1380
tcaggatcgt cttgaggctc agagctgggc gcgtcactac cagcagctcg cccgtgaaga   1440
gaaagaggca gaactggcag acgacatgga aaaaggcctg ccccagcacc tgtttgaatc   1500
gctatgcatc gatcatttgc aacgccacgg ggccagcaaa aaatccatta cccgtgcgtt   1560
tgatgacgat gttgagtttc aggagcgcat ggcagaacac atccggtaca tggttgaaac   1620
cattgctcac caccaggttg atattgattc agaggtataa aacgaatgag tactgcactc   1680
gcaacgctgg ctgggaagct ggctgaacgt gtcggcatgg attctgtcga cccacaggaa   1740
ctgatcacca ctcttcgcca gacggcattt aaaggtgatg ccagcgatgc gcagttcatc   1800
gcattactga tcgttgccaa ccagtacggc cttaatccgt ggacgaaaga aatttacgcc   1860
tttcctgata agcagaatgg catcgttccg gtggtgggcg ttgatggctg gtcccgcatc   1920
atcaatgaaa accagcagtt tgatggcatg gactttgagc aggacaatga atcctgtaca   1980
tgccggattt accgcaagga ccgtaatcat ccgatctgcg ttaccgaatg gatggatgaa   2040
tgccgccgcg aaccattcaa aactcgcgaa ggcagagaaa tcacgggcc gtggcagtcg   2100 catcccaaac ggatgttacg tcataaagcc atgattcagt gtgcccgtct ggccttcgga   2160
tttgctggta tctatgacaa ggatgaagcc gagcgcattg tcgaaaatac tgcatacact   2220
gcagaacgtc agccggaacg cgacatcact ccggttaacg atgaaaccat gcaggagatt   2280
aacactctgc tgatcgccct ggataaaaca tgggatgacg acttattgcc gctctgttcc   2340
cagatatttc gccgcgacat tcgtgcatcg tcagaactga cacaggccga agcagtaaaa   2400
```

```
gctcttggat tcctgaaaca gaaagccgca gagcagaagg tggcagcatg acaccggaca    2460
ttatcctgca gcgtaccggg atcgatgtga gagctgtcga acaggggat gatgcgtggc     2520
acaaattacg gctcggcgtc ataccgctt cagaagttca caacgtgata gcaaaacccc    2580
gctccggaaa gaagtggcct gacatgaaaa tgtcctactt ccacaccctg cttgctgagg   2640
tttgcaccgg tgtggctccg gaagttaacg ctaaagcact ggcctgggga aaacagtacg   2700
agaacgacgc cagaaccctg tttgaattca cttccggcgt gaatgttact gaatccccga   2760
tcatctatcg cgacgaaagt atgcgtaccg cctgctctcc cgatggttta tgcagtgacg   2820
gcaacggcct tgaactgaaa tgcccgttta cctcccggga tttcatgaag ttccggctcg    2880
gtggtttcga ggccataaag tcagcttaca tggcccaggt gcagtacagc atgtgggtga   2940
cgcgaaaaaa tgcctggtac tttgccaact atgacccgcg tatgaagcgt gaaggcctgc   3000
attatgtcgt gattgagcgg gatgaaaagt acatggcgag ttttgacgag atcgtgccgg   3060
agttcatcga aaaatggac gaggcactgg ctgaaattgg ttttgtattt ggggagcaat    3120
ggcgatgacg catcctcacg ataatatccg ggtaggcgca atcactttcg tctactccgt   3180
tacaaagcga ggctgggtat ttcccggcct ttctgttatc cgaaatccac tgaaagcaca   3240
gcggctggct gaggagataa ataataaacg aggggctgta tgcacaaagc atcttctgtt   3300
gagttaagaa cgagtatcga gatggcacat agccttgctc aaattggaat caggtttgtg   3360
ccaataccag tagaaacaga cgaagaatcc atgggtatgg acagttttcc ctttgatatg   3420
taacggtgaa cagttgttct acttttgttt gttagtcttg atgcttcact gatagataca   3480
agagccataa gaacctcaga tccttccgta tttagccagt atgttctcta gtgtggttcg   3540
ttgttttgc gtgagccatg agaacgaacc attgagatca tacttacttt gcatgtcact    3600
caaaattttt gcctcaaaac tggtgagctg aattttgca gttaaagcat cgtgtagtgt   3660
ttttcttagt ccgttacgta ggtaggaatc tgatgtaatg gttgttggta ttttgtcacc   3720
attcattttt atctggttgt tctcaagttc ggttacgaga tccatttgtc tatctagttc   3780
aacttggaaa atcaacgtat cagtcgggcg gcctcgctta tcaaccacca atttcatatt   3840
gctgtaagtg tttaaatctt tacttattgg tttcaaaacc cattggttaa gccttttaaa   3900
ctcatggtag ttattttcaa gcattaacat gaacttaaat tcatcaaggc taatctctat   3960
atttgccttg tgagttttct tttgtgttag ttcttttaat aaccactcat aaatcctcat   4020
agagtatttg ttttcaaaag acttaacatg ttccagatta tattttatga attttttaa   4080
ctggaaaaga taaggcaata tctcttcact aaaaactaat tctaattttt cgcttgagaa   4140
cttggcatag tttgtccact ggaaaatctc aaagccttta accaaggat tcctgatttc    4200
cacagttctc gtcatcagct ctctggttgc tttagctaat acaccataag cattttccct    4260
actgatgttc atcatctgag cgtattggtt ataagtgaac gataccgtcc gttctttcct   4320
tgtagggttt tcaatcgtgg ggttgagtag tgccacacag cataaaatta gcttggtttc   4380
atgctccgtt aagtcatagc gactaatcgc tagttcattt gctttgaaaa caactaattc   4440
agacatacat ctcaattggt ctaggtgatt ttaatcacta taccaattga gatgggctag   4500
tcaatgataa ttactagtcc ttttcctttg agttgtgggt atctgtaaat tctgctagac   4560
cttttgctgga aaacttgtaa attctgctag accctctgta aattccgcta gaccctttgtg   4620
tgtttttttt gtttatattc aagtggttat aatttataga ataaagaaag aataaaaaaa   4680
gataaaaaga atagatccca gccctgtgta taactcacta ctttagtcag ttccgcagta   4740
ttacaaaagg atgtcgcaaa cgctgtttgc tcctctacaa aacagacctt aaaaccctaa    4800
```

-continued

```
aggcttaagt agcaccctcg caagctcggt tgcggccgca atcgggcaaa tcgctgaata    4860
ttccttttgt ctccgaccat caggcacctg agtcgctgtc tttttcgtga cattcagttc    4920
gctgcgctca cggctctggc agtgaatggg ggtaaatggc actacaggcg cctttatgg     4980 attcatgcaa ggaaactacc cataatacaa gaaaagcccg tcacgggctt ctcagggcgt    5040
tttatggcgg gtctgctatg tggtgctatc tgacttttg ctgttcagca gttcctgccc     5100
tctgattttc cagtctgacc acttcggatt atcccgtgac aggtcattca gactggctaa    5160
tgcacccagt aaggcagcgg tatcatcaac ggggtctgac gctcagtgga acgaaaactc    5220
acgttaaggg attttggtca tgagattatc aaaaaggatc ttcacctaga tccttttaaa    5280
ttaaaaatga agttttaaat caatctaaag tatatatgag taaacttggt ctgacagtta    5340
ccaatgctta atcagtgagg cacctatctc agcgatctgt ctatttcgtt catccatagt    5400
tgcctgactc cccgtcgtgt agataactac gatacgggag ggcttaccat ctggccccag    5460
tgctgcaatg ataccgcgag acccacgctc accggctcca gatttatcag caataaacca    5520
gccagccgga agggccgagc gcagaagtgg tcctgcaact ttatccgcct ccatccagtc    5580
tattaattgt tgccgggaag ctagagtaag tagttcgcca gttaatagtt tgcgcaacgt    5640
tgttgccatt gctacaggca tcgtggtgtc acgctcgtcg tttggtatgg cttcattcag    5700
ctccggttcc caacgatcaa ggcgagttac atgatccccc atgttgtgca aaaaagcggt    5760 tagctcctte ggtcctccga tcgttgtcag aagtaagttg gccgcagtgt tatcactcat    5820
ggttatggca gcactgcata attctcttac tgtcatgcca tccgtaagat gcttttctgt    5880
gactggtgag tactcaacca agtcattctg agaatagtgt atgcggcgac cgagttgctc    5940
ttgcccggcg tcaatacggg ataataccgc gccacatagc agaactttaa aagtgctcat    6000
cattggaaaa cgttcttcgg ggcgaaaact ctcaaggatc ttaccgctgt tgagatccag    6060
ttcgatgtaa cccactcgtg cacccaactg atcttcagca tcttttactt tcaccagcgt    6120
ttctgggtga gcaaaaacag gaaggcaaaa tgccgcaaaa aagggaataa gggcgacacg    6180
gaaatgttga atactcatac tcttcctttt tcaatattat tgaagcattt atcagggtta    6240
ttgtctcatg agcggataca tatttgaatg tatttagaaa aataaacaaa tagggggttcc    6300 gcgcacattt ccccgaaaag tgccacctg                                      6329
```

<210> SEQ ID NO 51
<211> LENGTH: 3423
<212> TYPE: DNA
<213> ORGANISM: artificial sequence
<220> FEATURE:
<223> OTHER INFORMATION: Plasmid pSUH5

<400> SEQUENCE: 51

```
agattgcagc attacacgtc ttgagcgatt gtgtaggctg gagctgcttc gaagttccta      60
tactttctag agaataggaa cttcggaata ggaacttcaa gatcccctca cgctgccgca     120
agcactcagg gcgcaaggc tgctaaagga agcggaacac gtagaaagcc agtccgcaga     180
aacggtgctg accccggatg aatgtcagct actgggctat ctggacaagg gaaaacgcaa    240
gcgcaaagag aaagcaggta gcttgcagtg ggcttacatg gcgatagcta gactgggcgg    300
ttttatggac agcaagcgaa ccggaattgc cagctggggc gccctctggt aaggttggga    360
agccctgcaa agtaaactgg atggctttct tgccgccaag gatctgatgg cgcaggggat    420
caagatctga tcaagagaca ggatgaggat cgtttcgcat gattgaacaa gatggattgc    480
```

```
acgcaggttc tccggccgct tgggtggaga ggctattcgg ctatgactgg gcacaacaga    540
caatcggctg ctctgatgcc gccgtgttcc ggctgtcagc gcaggggcgc ccggttcttt    600
ttgtcaagac cgacctgtcc ggtgccctga atgaactgca ggacgaggca gcgcggctat    660
cgtggctggc cacgacgggc gttccttgcg cagctgtgct cgacgttgtc actgaagcgg    720
gaagggactg gctgctattg ggcgaagtgc cggggcagga tctcctgtca tctcaccttg    780
ctcctgccga gaaagtatcc atcatggctg atgcaatgcg gcggctgcat acgcttgatc    840
cggctacctg cccattcgac caccaagcga acatcgcat cgagcgagca cgtactcgga     900
tggaagccgg tcttgtcgat caggatgatc tggacgaaga gcatcagggg ctcgcgccag    960
ccgaactgtt cgccaggctc aaggcgcgca tgcccgacgg cgaggatctc gtcgtgaccc   1020
atggcgatgc ctgcttgccg aatatcatgg tggaaaatgg ccgcttttct ggattcatcg   1080
actgtggccg ctgggtgtg gcggaccgct atcaggacat agcgttggct acccgtgata    1140
ttgctgaaga gcttggcggc gaatgggctg accgcttcct cgtgctttac ggtatcgccg   1200
ctcccgattc gcagcgcatc gccttctatc gccttcttga cgagttcttc tgagcgggac   1260
tctggggttc gaaatgaccg accaagcgac gcccaacctg ccatcacgag atttcgattc   1320
caccgccgcc ttctatgaaa ggttgggctt cggaatcgtt ttccgggacg ccggctggat   1380
gatcctccag cgcggggatc tcatgctgga gttcttcgcc cacccagct tcaaaagcgc    1440
tctgaagttc ctatactttc tagagaatag gaacttcgga ataggaacta aggaggatat   1500
tcactataaa ataggcgta tcacgaggcc ctttcgtctt cacctcgaga atcataaaa     1560
aatttatttg ctttgtgagc ggataacaat tataatagat tcaattgtga gcggataaca   1620
atttcacaca gaattcatta agaggagaa attaactcat atggaccatg ctaattccc     1680
atgtcagccg ttaagtgttc ctgtgtcact gaaaattgct ttgagaggct ctaagggctt   1740
ctcagtgcgt tacatccctg gcttgttgtc cacaaccgtt aaaccttaaa gctttaaaa    1800
gccttatata ttctttttt tcttataaaa cttaaaacct tagaggctat ttaagttgct    1860
gatttatatt aattttattg ttcaaacatg agagcttagt acgtgaaaca tgagagctta   1920
gtacgttagc catgagagct tagtacgtta gccatgaggg tttagttcgt taaacatgag   1980
agcttagtac gttaaacatg agagcttagt acgtgaaaca tgagagctta gtacgtacta   2040
tcaacaggtt gaactgcgga tcttgcggcc gcaaaaatta aaatgaagt tttaaatcaa    2100
tctaaagtat atatgagtaa acttggtctg acagttacca atgcttaatc agtgaggcac   2160
ctatctcagc gatctgtcta tttcgttcat ccatagttgc ctgactcccc gtcgtgtaga   2220
taactacgat acgggagggc ttaccatctg gccccagtgc tgcaatgata ccgcgagacc   2280
cacgctcacc ggctccagat ttatcagcaa taaaccagcc agccgaagg gccgagcgca    2340
gaagtggtcc tgcaacttta tccgcctcca tccagtctat taattgttgc cgggaagcta   2400
gagtaagtag ttcgccagtt aatagtttgc gcaacgttgt tgccattgct acaggcatcg   2460
tggtgtcacg ctcgtcgttt ggtatggctt cattcagctc cggttcccaa cgatcaaggc   2520
gagttacatg atccccatg ttgtgcaaaa aagcggttag ctccttcggt cctccgatcg    2580
ttgtcagaag taagttggcc gcagtgttat cactcatggt tatggcagca ctgcataatt   2640
ctcttactgt catgccatcc gtaagatgct tttctgtgac tggtgagtac tcaaccaagt   2700
cattctgaga atagtgtatg cggcgaccga gttgctcttg cccggcgtca atacgggata   2760
ataccgcgcc acatagcaga actttaaaag tgctcatcat tggaaaacgt tcttcggggc   2820
gaaaactctc aaggatctta ccgctgttga gatccagttc gatgtaaccc actcgtgcac   2880
```

```
ccaactgatc ttcagcatct tttactttca ccagcgtttc tgggtgagca aaaacaggaa    2940
ggcaaaatgc cgcaaaaaag ggaataaggg cgacacggaa atgttgaata ctcatactct    3000 tccttttca atattattga agcatttatc agggttattg tctcatgagc ggatacatat    3060
ttgaatgtat ttagaaaaat aaacaaatag gggttccgcg cacatttccc cgaaaagtgc    3120
cacctgcatc gatggccccc cgatggtagt gtggggtctc cccatgcgag agtagggaac    3180
tgccaggcat caaataaaac gaaaggctca gtcgaaagac tgggcctttc gttttatctg    3240
ttgtttgtcg gtgaacgctc tcctgagtag gacaaatccg ccgggagcgg atttgaacgt    3300
tgcgaagcaa cggcccggag ggtggcgggc aggacgcccg ccataaactg ccaggcatca    3360
aattaagcag aaggccatcc tgacggatgg cctttttgcg tggccagtgc caagcttgca    3420
tgc                                                                  3423

<210> SEQ ID NO 52
<211> LENGTH: 156
<212> TYPE: DNA
<213> ORGANISM: artificial sequence
<220> FEATURE:
<223> OTHER INFORMATION: T5 promoter sequence

<400> SEQUENCE: 52
ctataaaaat aggcgtatca cgaggccctt tcgtcttcac ctcgagaaat cataaaaaat      60
ttatttgctt tgtgagcgga taacaattat aatagattca attgtgagcg gataacaatt    120
tcacacagaa ttcattaaag aggagaaatt aactca                              156
```

US 7,087,403 B2

BIOLOGICAL PRODUCTION OF TETRADEHYDROLYCOPENE

This application claims the benefit of U.S. Provisional Application No. 60/519,413 filed Nov. 12, 2003.

FIELD OF THE INVENTION

The invention relates to the field of molecular biology and microbiology. More specifically, a gene involved in carotenoid biosynthesis has been isolated from *Pantoea stewartii*, altered by error-prone PCR, and expressed in a recombinant host to produce 3,4,3',4'-tetradehydrolycopene (TDHL). The present invention also relates to a process for a producing TDHL.

BACKGROUND OF THE INVENTION

Carotenoids represent one of the most widely distributed and structurally diverse classes of natural pigments, producing light yellow to orange to deep red color. Eye-catching examples of carotenogenic tissues include carrots, tomatoes, red peppers, and the petals of daffodils and marigolds. Carotenoids are synthesized by all photosynthetic organisms, as well as some bacteria and fungi. These pigments have important functions in photosynthesis, nutrition, and protection against photooxidative damage. For example, animals do not have the ability to synthesize carotenoids and must obtain these nutritionally important compounds through their dietary sources. Structurally, carotenoids are 40-carbon ($C_{40}$) terpenoids derived from the isoprene biosynthetic pathway and its five-carbon universal isoprene building block, isopentenyl pyrophosphate (IPP).

Although more than 600 different carotenoids have been identified in nature, only a few are used industrially for food colors, animal feed additives, vitamin A precursors, pharmaceuticals, and cosmetics. Presently, most of the carotenoids used for industrial purposes are produced by chemical synthesis; however, these compounds are very difficult to make chemically (Nelis and Leenheer, *Appl. Bacteriol.,* 70:181–191 (1991)). Natural carotenoids can either be obtained by extraction of plant material or by microbial synthesis. At the present time, only a few plants are widely used for commercial carotenoid production.

Carotenoid production by microbial fermentation is a potential way to produce a variety of carotenoids in significant quantities. However, carotenoid production in non-carotenogenic microorganisms requires the ability to genetically engineer genes involved in carotenoid biosynthesis into industrially-useful microorganisms. Recently, carotenoid biosynthesis genes have been isolated from *Pantoea stewartii* and engineered into recombinant production hosts (WO 02/079395 A2 and commonly owned WO 03/016503 A2 corresponding to U.S. Ser. No. 10/218,118; hereby incorporated by reference). Methods are described for the production of carotenoids such as lycopene, zeaxanthin, canthaxanthin, β-carotene, lutein, and astaxanthin to name a few.

Commercial production of carotenoids not found in nature, or at least ones not naturally produced in commercially-suitable amounts, may also be accomplished by genetic engineering. Production hosts, such as *Escherichia coli*, can be engineered to produce various novel carotenoids through biochemical pathway engineering. These novel carotenoids may be have superior attributes in comparison to carotenoids currently used in a variety of applications. One such carotenoid is 3,4,3',4'-tetradehydrolycopene (TDHL).

Most carotenoids exhibit distinct color and can be viewed as natural pigments or colorants. Carotenoids are required elements of aquaculture and are also used in the poultry industry. Salmon and shrimp aquacultures are particularly useful applications as carotenoid pigmentation is critically important for the value of these organisms (Shahidi and Brown, *Crit Rev Food Sci,* 38(1):1–67 (1998)). Well-known examples of carotenoids used in the aquaculture industry are β-carotene and astaxanthin.

It is also known that carotenoids have utility as intermediates in the synthesis of cosmetics, flavors, and fragrances and compounds with potential electro-optic applications. Tetradehydrolycopene is particularly desirable for electro-optic applications. For example, electrical, optical, and redox characteristics of a polyene are a function of the length of the polyene run. Optical absorption red-shifts as the polyene run becomes longer, and the oxidation and reduction potentials become smaller as the polyene run becomes longer. These properties are believed to approach a limiting value when the polyene has 20 double bonds (W. Vetter et al., in *Carotenoids* (ed. O. Isler) Birkhäuser, Basel 1971). Tetradehydrolycopene has a run of 15 double bonds extending the entire length of the molecule, while lycopene only has 11 double bonds.

Carotenoids, such as lycopene, are used as antioxidants due to their large number of conjugated double bonds, making inclusion of these compounds in the diet desirable in view of their reported health benefits. Antioxidant potency is attributed to several factors, one being the length of the conjugated polyene chain in acyclic carotenoids (Miller et al., *FEBS Letters,* 384:240–242 (1996); Albrecht et al., *Nature Biotechnology,* (18):843–846 (2000)). A carotenoid having a long conjugated double-bond system, such as TDHL, has better antioxidant properties in comparison to carotenoids having a shorter conjugated polyene chain, such as lycopene.

Additionally, the bulk electrical properties of polyenes, such as carotenoids, are determined by the spacing between molecules in the solid state. Lycopene has a sterically bulky pentenyl end group on each side of the molecule, while TDHL does not. This is expected to allow closer interaction of all trans TDHL in the solid state compared to lycopene (Broszeit et al., *Liebigs Ann./Recueil,* 2205–13 (1997); Heinze et al., *J. Solid State Electrochem,* 2:102–9 (1998)).

Chemical synthesis of TDHL is not practical and the most direct biological route to this carotenoid species involves the desaturation of phytoene-like substrates by phytoene desaturases. Phytoene desaturase genes have been cloned, expressed, and sequenced from fungal species (*Neurospora crassa*), cyanobacteria (*Synechococcus*), bacterial species (*Rhodobacter capsulatus, Erwinia uredovora, Erwinia herbicola,* and *Pantoea stewartii*) as well as plant species (*Arabidopsis thaliana* (Linden et al., supra; Bartley et al., *J. Biol. Chem.,* 265:16020–16024 (1990); Scolnick et al., *Plant Physiol.,* 108: 1343, Bartely et al., *Eur. J. Biochem.,* 265: 396–403 (1999); and Hausmann and Sandmann, *Fungal Genet. Biol.,* 30:147–153 (2000)). In addition, oscillaxanthin, a 1,1'-dihydroxy-2,2'-di-β-L-rhamnosyl-1,2,1',2'-tetrahydro-3,4,3',4'-tetradehydrolycopene has been characterized from a blue green algae (*Arthrospira*). Although no genetic data is available, this species presumably contains a gene encoding a phytoene desaturase-type enzyme (Hertzber and Liaaen-Jensen, *Phytochemistry,* (8):1281–1292 (1969)).

Biological production of TDHL (in trace amounts) in a recombinant host has been reported (Schmidt-Dannert et al., *Nature Biotechnology,* (18):750–753 (2000); U.S. 2002/

0051998 A1)). A mutant phytoene desaturase, synthesized by gene shuffling fragments of the phytoene desaturase genes (crtI) from *Erwinia uredovora* and *Erwinia herbicola*, was expressed in *E. coli*, producing trace amounts of TDHL.

Linden et al. (*Z. Naturforsch*, (46c):1045–1091 (1991)) expressed the phytoene desaturase (crtI) gene from *E. uredovora* in *E. coli*, reporting the production of trace amounts of TDHL. Fraser et al. (*J Biol Chem*, 267(28):19891–19895 (1992)) reported sporadic production of trace amounts of TDHL when expressing the crtI gene from *E. uredovora* in *E. coli*. None of these references teach how to produce TDHL in industrially-suitable amounts in a recombinant host using genes from sources other than *E. uredovora* or *E. herbicola*.

Although small amounts of tetradehydrolycopene have been prepared chemically and trace amounts have been formed in biological systems, no means for economical production of significant amounts of TDHL exists (Hengartner et al., *Helvetica Chimica Acta.*, (75):1848–1865 (1992); Albrecht et al., supra; and Schmidt-Dannert et al., supra). The problem to be solved, therefore, is to provide materials and methods useful for producing industrially-suitable amounts of TDHL in a recombinant production host.

Applicants have solved the stated problem by mutating crtI from *Pantoea stewartii* and expressing the mutated crtI genes along with other carotenoid biosynthetic enzymes in a recombinant host to produce industrially-suitable amounts of TDHL.

SUMMARY OF THE INVENTION

The invention relates to mutant polypeptides and nucleic acid molecules encoding the same for the conversion of phytoene desaturase substrates to TDHL. Preferred phytoene desaturase substrates include, but are not limited to phytoene, phytofluene, ξ-carotene, neurosporene, and lycopene.

Accordingly, the invention provides an isolated nucleic acid molecule encoding a mutant phytoene desaturase comprising:
  a) a nucleic acid molecule encoding the amino acid sequence selected from the group consisting of SEQ ID NOs:18 and 20; or
  b) is completely complementary to (a).

Additionally the invention provides polypeptides encoded by the genes of the invention as well as genetic chimera and transformed host cells comprising the same.

In another embodiment the invention provides a method for the production of tetradehydrolycopene comprising:
  a) providing a recombinant host cell comprising:
    i) an isolated nucleic acid molecule encoding a mutant phytoene desaturase having the amino acid sequence selected from the group consisting of SEQ ID NO:18 and SEQ ID NO:20;
    ii) a phytoene desaturase substrate;
  b) growing the recombinant host cell of (a) under conditions whereby the isolated nucleic acid molecule of (a)(i) is expressed and the phytoene desaturase substrate is converted to tetradehydrolycopene; and
  c) optionally recovering the tetradehydrolycopene.

In a preferred embodiment the invention provides a method for the production of tetradehydrolycopene comprising:
  a) providing a recombinant host cell comprising:
    i) a functional isoprenoid biosynthesis pathway, said isoprenoid biosynthesis pathway comprising at least one copy of the genes dxs, ispC, ispD, ispE, ispF, ispG, ispH, idi, and ispA; wherein one or more of the isoprenoid pathway genes is upregulated;
    ii) a functional carotenoid biosynthesis pathway, said carotenoid biosynthesis pathway comprising at least one copy of the genes crtE, crtB, and crtI; wherein one or more of the carotenoid biosynthesis genes are upregulated;
    iii) an isolated nucleic acid molecule encoding a mutant phytoene desaturase having the amino acid sequence selected from the group consisting of SEQ ID NO:18 and SEQ ID NO:20; said isolated nucleic acid molecule operably linked to suitable regulatory sequence; and
  b) growing the recombinant host cell of (a) under conditions whereby the isolated nucleic acid molecule of (a) is expressed and tetradehydrolycopene is produced; and
c) optionally recovering the tetradehydrolycopene.

Alternatively the invention provides a method of producing tetradehydrolycopene in vitro comprising
  a) contacting a phytoene desaturase substrate with a mutant phytoene desaturase polypeptide selected from the group consisting of SEQ ID NO:18 and SEQ ID NO:20 under suitable reaction conditions whereby tetradehydrolycopene is produced; and
  b) optionally recovering the tetradehydrolycopene produced in step (a).

BRIEF DESCRIPTION OF THE DRAWINGS SEQUENCE DESCRIPTIONS AND

Figure 5:
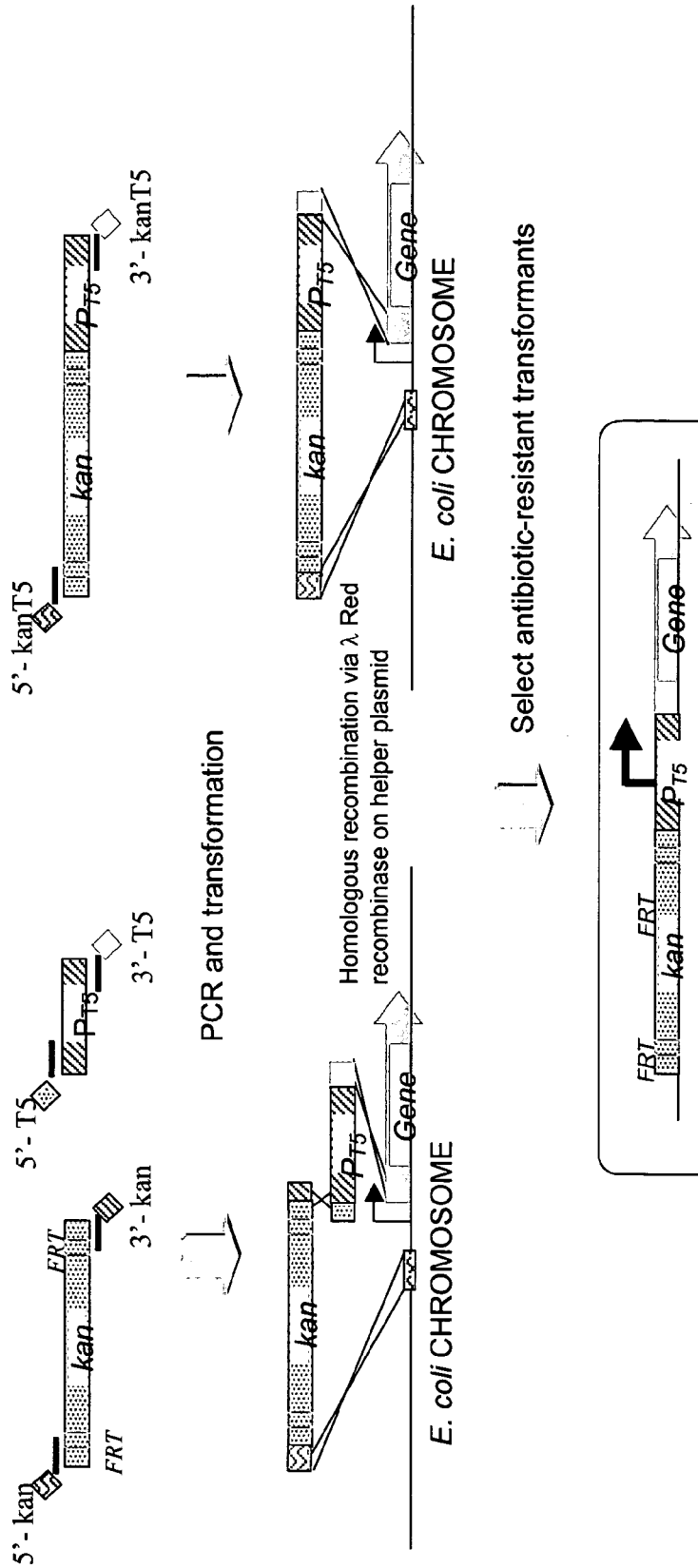

FIG. 5 shows the two PCR fragment method for integration of a strong promoter upstream of isoprenoid genes in the *E. coli* chromosome (U.S. Ser. No. 10/734,936 and U.S. Ser. No. 10/735,442).

Figure 6:
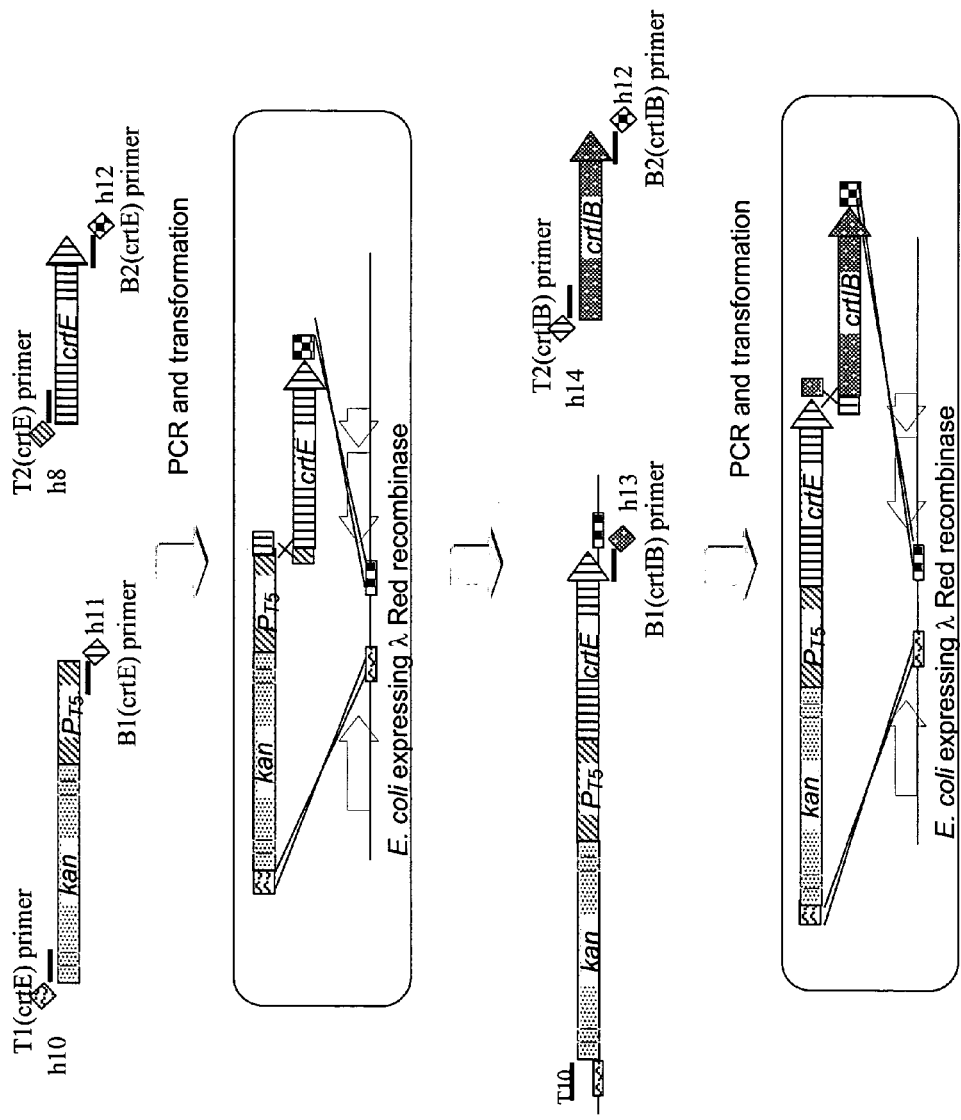

FIG. 6 shows the strategy for integration of crtEIB into the *E. coli* chromosome.

Figure 7:
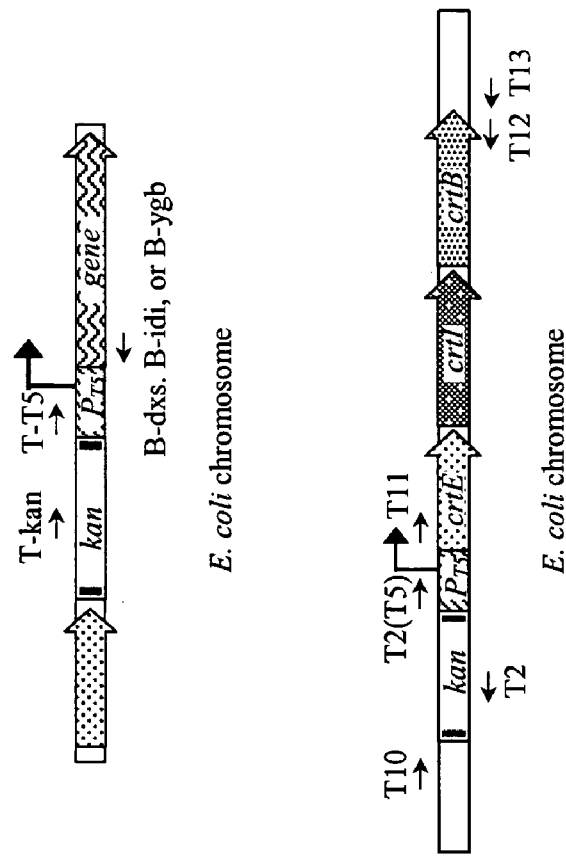

FIG. 7 shows the position of nucleotide primers used to confirm promoter replacements and chromosomal integrations.

Figure 8:
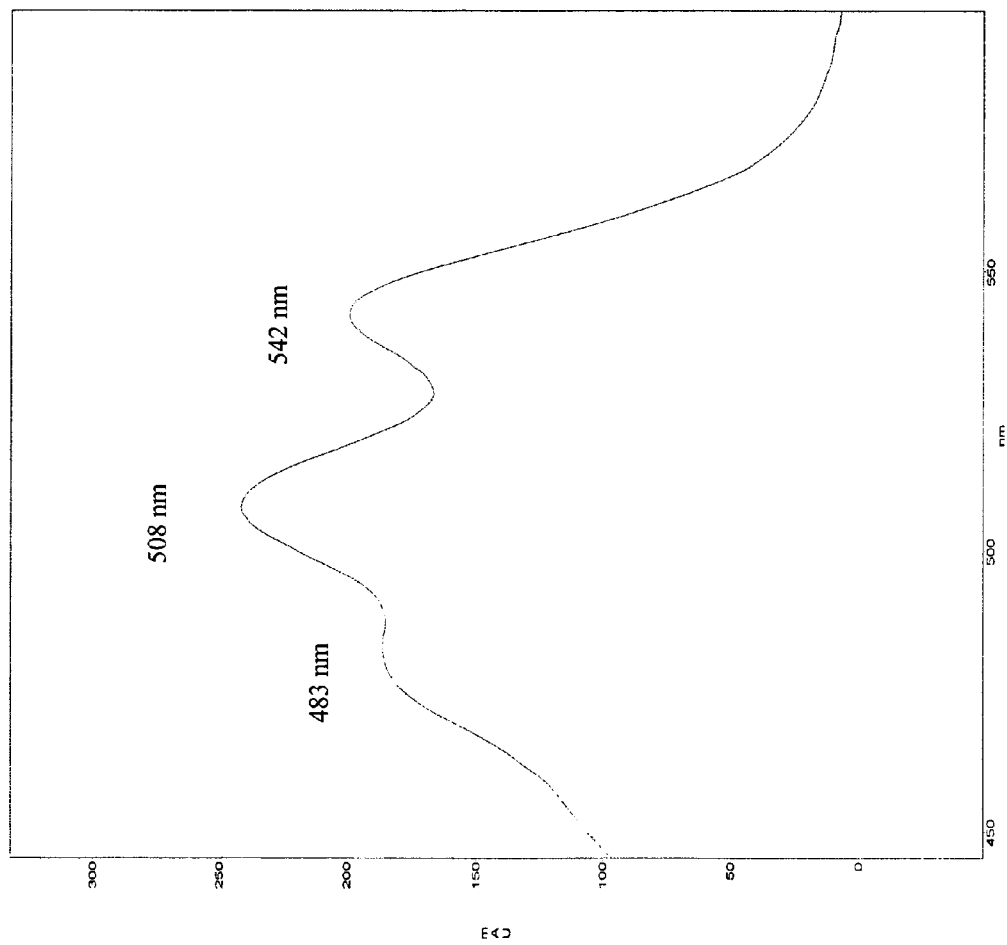

FIG. 8 shows the spectrum of tetradehydrolycopene produced by fermentation.

The invention can be more fully understood from the following detailed description and the accompanying sequence descriptions which form a part of this application.

The following sequences are in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

| Gene/Protein Product | Source | Nucleotide SEQ ID NO | Amino Acid SEQ ID NO |
|---|---|---|---|
| CrtE | *Pantoea stewartii* | 1 | 2 |
| CrtX | *Pantoea stewartii* | 3 | 4 |
| CrtY | *Pantoea stewartii* | 5 | 6 |
| CrtI | *Pantoea stewartii* | 7 | 8 |
| CrtB | *Pantoea stewartii* | 9 | 10 |
| CrtZ | *Pantoea stewartii* | 11 | 12 |
| CrtI-514 variant | Artificial sequence | 17 | 18 |
| CrtI-515 variant | Artificial sequence | 19 | 20 |

SEQ ID NOs:13–14 are oligonucleotide primers used to amplify the carotenoid biosynthetic genes from *P. stewartii*.

SEQ ID NOs:15–16 are oligonucleotide primers used to amplify *P. stewartii* crtI in error-prone PCR.

SEQ ID NO:17 is the nucleic acid sequence of the mutant phytoene desaturase variant crtI-514.

SEQ ID NO:18 is the deduced amino acid sequence of the mutant phytoene desaturase variant crtI-514.

SEQ ID NO:19 is the nucleic acid sequence of the mutant phytoene desaturase variant crtI-515.

SEQ ID NO:20 is the deduced amino acid sequence of the mutant phytoene desaturase variant crtI-515.

SEQ ID NO:21 is the nucleic acid sequence of primer 5'-kan(dxs).

SEQ ID NO:22 is the nucleic acid sequence of primer 5'-kan(idi).

SEQ ID NO:23 is the nucleic acid sequence of primer 5'-kan(ispDF).

SEQ ID NO:24 is the nucleic acid sequence of primer 5'-kan(ispAdxs).

SEQ ID NO:25 is the nucleic acid sequence of primer 3'-kan.

SEQ ID NO:26 is the nucleic acid sequence of primer 5'-T5.

SEQ ID NO:27 is the nucleic acid sequence of primer 3'-T5(dxs).

SEQ ID NO:28 is the nucleic acid sequence of primer 3'-T5(idi).

SEQ ID NO:29 is the nucleic acid sequence of primer 3'-T5(ispDF).

SEQ ID NO:30 is the nucleic acid sequence of primer 3'-T5(ispAdxs).

SEQ ID NO:31 is the nucleic acid sequence of primer T-kan.

SEQ ID NO:32 is the nucleic acid sequence of primer B-dxs.

SEQ ID NO:33 is the nucleic acid sequence of primer T-T5.

SEQ ID NO:34 is the nucleic acid sequence of primer B-idi.

SEQ ID NO:35 is the nucleic acid sequence of primer B-ispDF.

SEQ ID NO:36 is the nucleic acid sequence of primer T1(crtE).

SEQ ID NO:37 is the nucleic acid sequence of primer B1(crtE).

SEQ ID NO:38 is the nucleic acid sequence of primer T2(crtE).

SEQ ID NO:39 is the nucleic acid sequence of primer B2(crtE).

SEQ ID NO:40 is the nucleic acid sequence of primer T10.

SEQ ID NO:41 is the nucleic acid sequence of primer T13.

SEQ ID NO:42 is the nucleic acid sequence of primer B1(crtIB).

SEQ ID NO:43 is the nucleic acid sequence of primer T2(crtIB).

SEQ ID NO:44 is the nucleic acid sequence of primer B2(crtIB).

SEQ ID NO:45 is the nucleic acid sequence of primer T2.

SEQ ID NO:46 is the nucleic acid sequence of primer T2(T5).

SEQ ID NO:47 is the nucleic acid sequence of primer T12.

SEQ ID NO:48 is the nucleic acid sequence of primer T11.

SEQ ID NO:49 is the nucleotide sequence for plasmid pPCB15.

SEQ ID NO:50 is the nucleotide sequence for plasmid pKD46.

SEQ ID NO:51 is the nucleotide sequence for plasmid psUH5.

SEQ ID NO:52 is the nucleotide sequence for the PT5 promoter.

BRIEF DESCRIPTION OF BIOLOGICAL DEPOSITS

Applicants made the following biological deposit under the terms of the Budapest Treaty on the International Recognition of the Deposit of Microorganisms for the purposes of Patent Procedure:

| Depositor Identification Reference | Int'l. Depository Designation | Date of Deposit |
|---|---|---|
| Plasmid pCP20 | ATCC# PTA-4455 | Jun. 13, 2002 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The claimed genes and their expression products are useful for the production of recombinant organisms having the ability to produce TDHL at industrially-suitable quantities. TDHL has industrial applications in the optics and electrical industries and may be used as an antioxidant in dietary supplements.

The disclosure below provides a detailed description of the isolation of carotenoid synthesis genes from *Pantoea stewartii* subsp. *stewartii*, modification of these genes by genetic engineering, and their insertion into compatible plasmids suitable for cloning and recombinant expression in bacteria, yeasts, fungi, and higher plants. Also disclosed are methods for preparation of the appropriate enzymes and the methods for TDHL production in these various hosts.

In this disclosure, a number of terms and abbreviations are used. The following definitions are provided.

The term "tetradehydrolycopene" is abbreviated TDHL and refers to the compound 3,4,3',4'-tetradehydrolycopene, also known as bisdehydrolycopene.

The term "*Pantoea agglomerans*" is used interchangeably with the name *Erwinia herbicola* (Beji et al., *Int. J. Syst. Bacteriol.*, 38:77–88 (1988) and Gavini et al., *Int. J. Syst. Bacteriol.*, 39:337–345 (1989)).

The term "*Pantoea ananatis*" is used interchangeably with the name *Erwinia uredovora* (Mergaert et al., *Int. J. Syst. Bacteriol.*, 43:162–173 (1993)).

The term "*Pantoea stewartii* subsp. *stewartii*" is abbreviated as "*Pantoea stewartii*" or "*P. stewartii*" and is used interchangeably with *Erwinia stewartii* (Mergaert et al., supra).

The term "carotenoid" means any lipophilic isoprenoid compound, produced either synthetically or naturally. All carotenoids are synthesized from molecules of isopentenyl pyrophosphate (IPP) as the universal isoprene building block.

Figure 2:
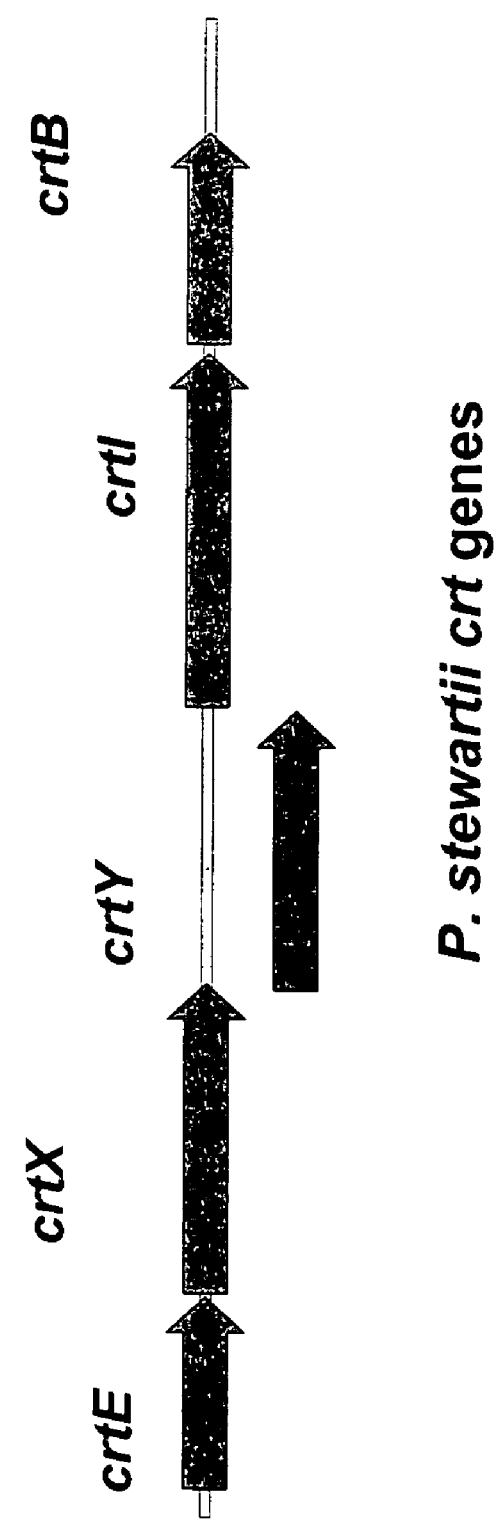
FIG. 2 shows the gene cluster containing the carotenoid biosynthetic genes crtEXYIB from *Pantoea stewartii*.

The term "CrtE" refers to a geranylgeranyl pyrophosphate synthase enzyme encoded by crtE gene represented in SEQ ID NO:1, which converts trans-trans-farnesyl diphosphate+isopentenyl diphosphate to pyrophosphate+geranylgeranyl diphosphate. Preferred in the present invention is a crtE gene isolated from *Pantoea stewartii* having a gene cluster arranged as shown in FIG. 2.

The term "CrtY" refers to a lycopene cyclase enzyme encoded by crtY gene represented in SEQ ID NO:5, which converts lycopene to β-carotene. Preferred in the present invention is a crtY gene isolated from *Pantoea stewartii* having a gene cluster arranged as shown in FIG. 2.

The term "Crtl" refers to a phytoene desaturase enzyme encoded by crtl gene represented in SEQ ID NO:7, which converts phytoene into lycopene via the intermediates phytofluene, zeta-carotene, and neurosporene by the introduction of 4 double-bonds. Preferred in the present invention is a crtl gene isolated from *Pantoea stewartii* having a gene cluster arranged as shown in FIG. 2.

The term "mutant Crtl" refers to a phytoene desaturase created by error-prone PCR which is shown to catalyze the production of 3,4,3',4'-tetradehydrolycopene in significantly higher amounts in comparison to the unmodified phytoene desaturase as represented in SEQ ID NO:7. The "mutant crtl" phytoene desaturases of the present invention are represented by the amino acid sequences of SEQ ID NOs:18 and 20.

As used herein, the term "desaturase substrate" or "phytoene desaturase substrate" refers to any substrate capable of being desaturated by a mutant crtl of the present invention including, but not limited to phytoene, phytofluene, ξ-carotene, neurosporene, and lycopene.

The term "CrtB" refers to a phytoene synthase enzyme encoded by crtB gene represented in SEQ ID NO:9, which catalyses reaction from prephytoene diphosphate to phytoene. Preferred in the present invention is a crtB gene isolated from *Pantoea stewartii* having a gene cluster arranged as shown in FIG. 2.

The term "CrtZ" refers to a β-carotene hydroxylase enzyme encoded by crtZ gene represented in SEQ ID NO:11, which catalyses hydroxylation reaction from β-carotene to zeaxanthin.

Figure 4:
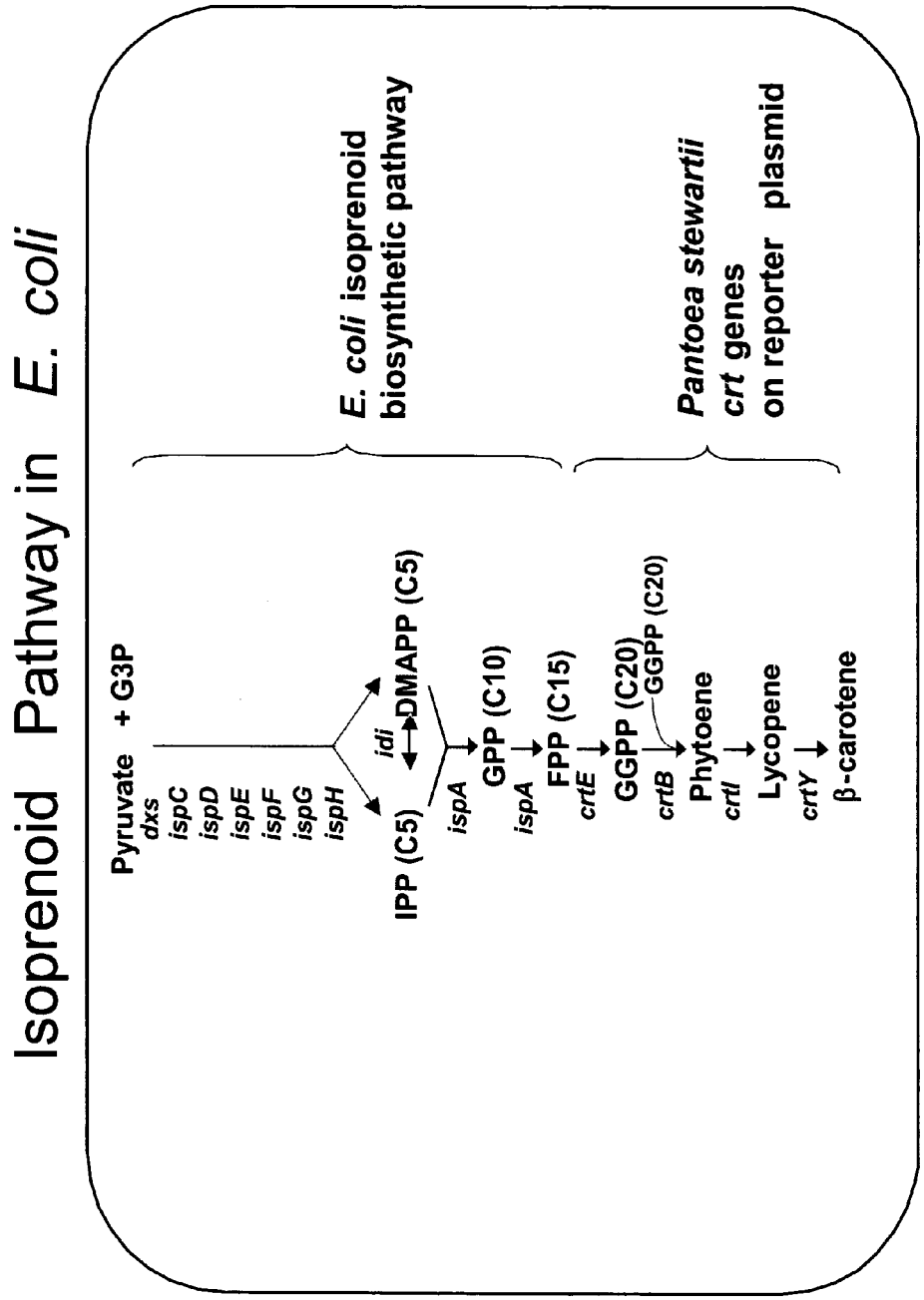
FIG. 4 shows the isoprenoid pathway for the production of carotenoids in *E. coli*.

The terms "upper isoprenoid pathway", "upper pathway", "isoprenoid pathway", and "*E. coli* isoprenoid biosynthetic pathway" will be use interchangeably and will refer to enzymes involved in converting pyruvate and glyceraldehyde-3-phosphate (G3P) to farnesyl pyrophosphate (FPP) (FIG. 4). These enzymes are encoded by genes that include, but are not limited to: the "dxs" gene (encoding 1-deoxyxylulose-5-phosphate synthase); the "ispC" gene (encoding 1-deoxyxylulose-5-phosphate reductoisomerase; also known at dxr); the "ispD" gene (encoding a 2C-methyl-D-erythritol cytidyltransferase enzyme; also known as ygbP); the "ispE" gene (encoding 4-diphosphocytidyl-2-C-methyl-erythritol kinase; also known as ychB); the "ispF" gene (encoding a 2C-methyl-D-erythritol 2,4-cyclodiphosphate synthase; also known as ygbB); the "pyrG" gene (encoding a CTP synthase); the "ispH" gene (also known as lytB) involved in the formation of dimethylallyl diphosphate; the "ispG" gene (also known as gcpE) involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase).

The terms "lower carotenoid biosynthetic pathway", "carotenoid biosynthesis pathway", and "lower pathway" will be used interchangeably and refer to those enzymes which convert FPP to a suite of carotenoids (FIG. 4). These enzymes are encoded by genes that include, but are not limited to: crtE, crtX, crtY, crtl, crtB, crtZ, crtW, crtO, and crtU. Finally, the term "lower carotenoid biosynthetic enzyme" is an inclusive term referring to any and all of the enzymes in the present lower pathway including, but not limited to: CrtE, CrtX, CrtY, Crtl, CrtB, CrtW, CrtO, CrtU, and CrtZ.

The term "pKD46" refers to the plasmid (SEQ ID NO:50) that was constructed by Datsenko and Wanner (PNAS., 97:6640–6645 (2000)).

The term "psUH5" refers to the plasmid (SEQ ID NO:51) that was constructed by cloning a phage T5 promoter ($P_{T5}$) region into the NdeI restriction endonuclease site of pKD4 (Datsenko and Wanner, supra). It was used as a template plasmid for PCR amplification of a fused kanamycin selectable marker/phage T5 promoter linear nucleic acid molecule.

The terms "$P_{T5}$ promoter" and "T5 promoter" refer to the nucleic acid molecule (SEQ ID NO:52) that comprises the −10 and −35 consensus sequences, lactose operator (lacO), and ribosomal binding site (rbs) from phage T5.

The term "helper plasmid" refers to either pKD46 (encoding λ-Red recombinase) or pCP20 (ATCC PTA4455; encoding FLP site-specific recombinase (Datsenko and Wanner, supra)).

The terms "λ-Red recombinase system", "λ-Red system", and "λ-Red recombinase" are used interchangeably and refer to three essential genes, exo, bet, and gam, that are contained on a helper plasmid, pKD46 (Datsenko and Wanner, supra.; SEQ ID NO:50).

The term "homology arm" refers to a portion of a nucleic acid molecule having a nucleotide sequence that enables homologous recombination between two nucleic acids having substantially the same nucleotide sequence in a particular region of two different nucleic acids. The preferred size range of the homology arm is from about 10 to about 50 nucleotides in length.

The term "triple homologous recombination" in the present invention refers to a genetic recombination between two linear DNA nucleotides and the target chromosome via their homologous sequences resulting in chromosomal integration of two linear nucleic acid molecules into the target of chromosome.

The term "site-specific recombinase" is used in the present invention to describe a system comprised of one or more enzymes which recognize specific nucleotide sequences (recombination target sites) and which catalyze recombination between the recombination target sites. Site-specific recombination provides a method to rearrange, delete, or introduce exogenous DNA. Examples of site-specific recombinases and their associated recombination target sites are flippase (FLP/FRT), Cre-lox, R/RS, Gin/gix, Xer/dif, and Int/att. In the present invention, a site-specific recombinase was used to remove selectable markers. Antibiotic resistance markers, flanked on both sides by FRT recombination target sites, are removed by expression of the FLP site-specific recombinase. This method is used so that the numbers of chromosomal modifications necessary for microbial pathway engineering is not limited to the number of available selection markers (Huang et al., *J. Bacteriol.*, 179(19): 6076–6083 (1997)).

The terms "transduction" and "generalized transduction" are used interchangeably and refer to a phenomenon in which bacterial DNA is transferred from one bacterial cell (the donor) to another (the recipient) by a phage particle containing bacterial DNA.

As used herein, the terms "P1 donor cell" and "donor cell" are used interchangeably and refer to a bacterial strain susceptible to infection by a bacteriophage or virus, and which serves as a source for the nucleic acid molecules packaged into the transducing particles. Typically, the genetic make up of the donor cell is similar or identical to the "recipient cell" which serves to receive P1 lysate containing transducing phage or virus produced by the donor cell.

As used herein, the terms "P1 recipient cell" and "recipient cell" are used interchangeably and refer to a bacterial strain susceptible to infection by a bacteriophage or virus and which serves to receive lysate containing transducing phage or virus produced by the donor cell.

As used herein, the terms "stacking", "combinatorial stacking", "chromosomal stacking", and "trait stacking" are used interchangeably and refer to the repeated process of stacking multiple genetic traits into one *E. Coli* host using the bacteriophage P1 in combination with the site-specific recombinase system for removal of selection markers (U.S. Ser. No. 10/734,778; hereby incorporated by reference).

The terms "parallel combinatorial fashion" and "combinatorial fashion" are used interchangeably and refer to the P1 transduction with the P1 lysate mixture made from various donor cells, so that multiple genetic traits can be moved to the recipient cell in parallel (U.S. Ser. No. 10/734,778).

The terms "integration cassette" and "recombination element" refer to a linear nucleic acid construct useful for the transformation of a recombination proficient bacterial host. Recombination elements of the invention may include a variety of genetic elements such as selectable markers, functional DNA fragments, and recombination regions having homology to regions on a bacterial chromosome or on other recombination elements. Functional DNA fragments can include coding sequences, genes, gene clusters, sequences encoding functional RNA, promoters, and other regulatory elements specifically engineered into the recombination element to impart a desired phenotypic change upon recombination.

The terms "inter-operon chromosomal integration site" or "inter-operon region" refer to a chromosomal site where integration of exogenous DNA using the current invention is targeted and where integration of the exogenous DNA will not disrupt the functionality of an endogenous operon within the host.

As used herein, the terms "industrially-suitable amount" and "commercially significant amount" are defined as a titer of tetradehydrolycopene of at least 150 ppm (based on dry cell weight).

"Open reading frame" is abbreviated ORF.

"Polymerase chain reaction" is abbreviated PCR.

"High Performance Liquid Chromatography" is abbreviated HPLC.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment, the length for a hybridizable nucleic acid is at least about 10 nucleotides. Preferably, a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods including, but not limited to, those described in: *Computational Molecular Biology* (Lesk, A. M., ed.) Oxford University Press, NY (1988); *Biocomputinq: Informatics and Genome Projects* (Smith, D. W., ed.) Academic Press, NY (1993); *Computer Analysis of Sequence Data, Part I* (Griffin, A. M., and Griffin, H. G., eds.) Humana Press, N.J. (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp, *CABIOS.,* 5:151–153 (1989)) with the default parameters (GAP PENALTY=10, GAP LENGTH PENALTY=10). Default parameters for pairwise alignments using the Clustal method were KTUPLE=1, GAP PENALTY=3, WINDOW=5 and DIAGONALS SAVED=5.

"Codon degeneracy" refers to the nature in the genetic code permitting variation of the nucleotide sequence without effecting the amino acid sequence of an encoded polypeptide. Accordingly, the instant invention relates to any nucleic acid molecule that encodes the amino acid sequence encoding the instant microbial polypeptides as set forth in SEQ ID NOs:18 and 20. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts to the 3' end of the mRNA precursor (normally limited to eukaryotes).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid molecule so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid molecule of the invention. Expression may also refer to translation of mRNA into a polypeptide.

"Transformation" refers to the transfer of a nucleic acid molecule into the genome of a host organism, resulting in genetically stable inheritance. As used herein, the host cell genome includes both chromosomal or extrachromosomal (i.e. a vector) genes with the host cell. Host organisms containing the transformed nucleic acid molecules are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res., [Proc. Int. Symp.]* (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters (set by the software manufacturer) which originally load with the software when first initialized.

Standard recombinant DNA and molecular cloning techniques used here are well known in the art and are described by Sambrook et al. (supra); Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention provides CrtI phytoene desaturases having the ability to convert phytoene desaturase substrates to tetradehydrolycopene (TDHL). Genes encoding these polypeptides may be expressed in recombinant hosts comprising various elements of the carotenoid biosynthetic pathway for the production of TDHL. It is contemplated that the carotenoid biosynthetic pathway may be manipulated in many hosts to optimize production of this carotenoid product.

Construction of CrtI Mutants

The present CrtI mutants were derived from crtI genes isolated from *Pantoea stewartii* and were subjected to mutagenesis by error-prone PCR. Mutants were selected on the basis of their ability to convert phytoene to 3,4,3',4'-tetradehydrolycopene. The relevant crtI genes were isolated by polymerase chain reaction using primers appropriately designed on the basis of the known *Pantoea stewartii* sequence, disclosed herein as SEQ ID NO:7. The method of error-prone PCR was chosen as the vehicle for mutagenesis for its facility, however the skilled artisan will appreciate that other common mutagenesis methods are equally applicable.

Error-Prone PCR

Error-prone PCR is a method for introducing mutations into DNA using low stringency PCR amplification conditions. This can be achieved by modifying the PCR conditions such as altering the ratios of dNTPs or adding various amounts of manganese chloride in the reaction (Fromant et al., *Anal Biochem*, 224(1):347–53 (1995); Lin-Goerke et al., *Biotechniques*, 23(3):409–12 (1997); Melnikov et al., *Nucleic Acids Research*, 27(4):1056–1062 (1999); Leung et al., *Techniques*, 1:11–15 (1989); and Zhou et al., *Nucleic Acids Res.* 19:6052—6052 (1991)). The pool of mutated DNA fragments are then cloned to yield a library of mutated plasmids that can then be screened following expression in a host such as *E. coli*. In the filed of carotenoids this approach has been described in U.S. Pat. No. 6,040,165; U.S. Pat. No. 5,807,725; Ohnuma et al., *J Biol Chem*, 269(20):14792–7 (1994); Ohnuma et al., *J Biol Chem*, 271(17):10087–95 (1996); Ohnuma et al., *J Biol Chem*, 271:18831–18837 (1996); Ohnuma et al., *J Biol Chem*, 272:5192–5198 (1997); and Okada et al., *Eur J Biochem*, 255:52–59 (1998).

Microbial Recombinant Gene Expression

The present mutant crtI genes may be produced in heterologous host cells, particularly in the cells of microbial hosts. Preferred heterologous host cells for expression of the present nucleic acid molecules are microbial hosts that can be found broadly within the yeast, algal, fungal or bacterial families and which grow over a wide range of temperature, pH values, and solvent tolerances. For example, it is contemplated that any of bacteria, algae, yeast, or filamentous fungi will be suitable hosts for expression of the present nucleic acid molecules. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micro-nutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of host strains include, but are not limited to, bacterial species including but not limited to *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium, Klebsiella, Burkholderia, Sphingomonas, Paracoccus, Pandoraea, Delftia*, and *Comamonas*; species of yeast, including but not limited to *Aspergillus, Trichoderma, Saccharomyces, Pichia, Candida*, and *Hansenula*; and algal species including but not limited to *Spirulina, Haematococcus*, and *Dunalliela*.

Microbial expression systems and expression vectors containing regulatory sequences that direct high-level expression of foreign proteins are well known to those skilled in the art. Any of these could be used to construct chimeric genes for production of the mutant crtI genes of the invention. These chimeric genes could then be introduced into appropriate microorganisms via transformation to provide high-level expression of the enzymes.

Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

In a preferred embodiment, the recombinant hosts are chromosomally engineered for the expression of the mutant crtI genes and the production of 3,4,3',4'-tetradehydrolycopene. Chromosomal engineering is preferred since the use of multi-copy vectors to express a gene of interest under the control of a strong or conditional promoter has several drawbacks. It is sometimes difficult to maintain the vectors due to segregational instability. Deleterious effects on cell viability and growth are often observed due to the vector burden. It is also difficult to control the optimal expression level of desired genes on a vector. To avoid the undesirable effects of using a multi-copy vector, a chromosomal integration approach using homologous recombination via a single insertion of bacteriophage λ, transposons, or other suitable vectors containing the gene of interest is preferred. Where the desired host cell is a bacterium, a particularly suitable method is disclosed in commonly owned U.S. Ser. No. 10/734,936.

Initiation control regions or promoters, which are useful to drive expression of the instant ORF's in the desired host cell, are numerous and familiar to those skilled in the art. Virtually any promoter capable of driving these genes is suitable for the present invention including, but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T5, T7, tac, and trc (useful for expression in *Escherichia coli*) as well as the amy, apr, npr promoters and various phage promoters useful for expression in *Bacillus*.

Termination control and mRNA stabilizing regions may also be derived from various genes native to the preferred hosts. Optionally, a termination site may be unnecessary, however, it is most preferred if included.

Accordingly, it is expected that introduction of chimeric genes encoding the instant bacterial enzymes under the control of the appropriate promoters will demonstrate increased production of 3,4,3',4'-tetradehydrolycopene. It is additionally expected that introduction of chimeric genes encoding one or more of the instant sequences will lead to production of carotenoid compounds in the host microbe of choice. Basis for this expectation is found in the ubiquity of the isoprene biosynthetic pathway in microbes. With an appropriate genetic transformation system, it should be possible to genetically engineer a variety of non-carotenogenic hosts. This has been shown, for example, using *E. herbicola* crt genes, to produce various carotenoids in the hosts *E. coli, Agrobacterium tumefaciens, S. cerevisiae, Pichia pastoris* (yeast), *Aspergillus nidulans* (fungi), *Rhodobacter sphaeroides*, and higher plants (U.S. Pat. No. 5,656,472).

Recombinant Production—Plants

Plants are also known to produce carotenoid compounds. The nucleic acid molecules of the instant invention may be used to create transgenic plants having the ability to express the microbial protein (Fraser, P. and Bramley, P., *Progress in Lipid Research*, 43:228–265 (2004)). Preferred plant hosts will be any variety that will support a high production level of the instant proteins. Suitable green plants will include but are not limited to soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*, L), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Overexpression of the carotenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences or the present invention, should be capable of promoting expression of the present gene product. Examples of high-level plant promoters that may be used in this invention include the promoter of the small subunit (ss) of the ribulose-1,5-bisphosphate carboxylase from soybean (Berry-Lowe et al., *J. Molecular and App. Gen.*, 1:483–498 (1982)) and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pages 29–38; Coruzzi, G. et al., *J. Biol. Chem.*, 258:1399 (1983), and Dunsmuir, P. et al., *J. Mol. Appl. Genet.*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select, and propagate host cells containing the chimeric gene. The skilled artisan will also recognize that different independent transformation events will result in different levels and patterns of expression (Jones et al., *EMBO J.*, 4:2411–2418 (1985); De Almeida et al., *Mol. Gen. Genetics*, 218:78–86 (1989)), and thus multiple events must be screened in order to obtain lines displaying the desired expression level and pattern. Such screening may be accomplished by Southern analysis of DNA blots (Southern, *J. Mol. Biol.*, 98:503 (1975)). Northern analysis of mRNA expression (Kroczek, J., *Chromatogr. Biomed. Appl.*, 618 (1–2):133–145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell*, 56:247–253 (1989)), signal sequences or sequences encoding endoplasmic reticulum localization (Chrispeels, J. J., *Ann. Rev. Plant Phys. Plant Mol. Biol.*, 42:21–53 (1991)), or nuclear localization signals (Raikhel, N., *Plant Phys.*, 100: 1627–1632 (1992)). While the references cited give examples of each of these, the list is not exhaustive and more targeting signals of utility may be discovered in the future that are useful in the invention.

Desaturation of Phytoene and Phytoene Desaturase Genes

Figure 1:
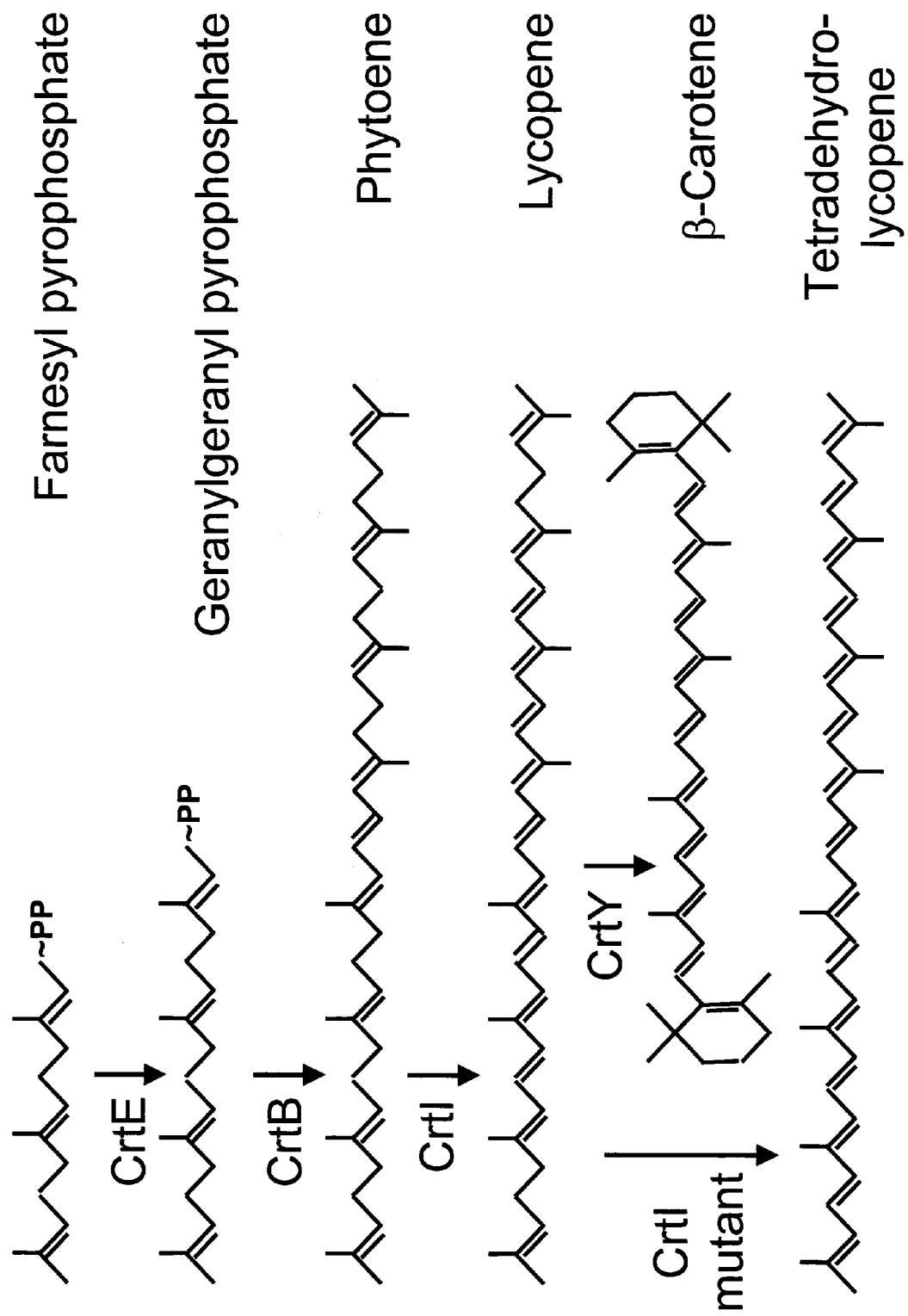
FIG. 1 shows the chemical structures involved in the present carotenoid pathway.

The activity of the present mutant CrtI polypeptides result in the production of 3,4,3',4'-tetradehydrolycopene from phytoene, and other phytoene desaturase substrates. The formation of phytoene (7,8,11,12,7',8',11',12'-ω-octahydro-ω, ω-carotene), a colorless carotenoid, represents the first step unique to biosynthesis of carotenoids (FIG. 1). Phytoene is converted to more oxidized carotenoids by the action of phytoene desaturases. These enzymes catalyze the sequential dehydrogenation of the carbon backbone, which leads to an increase in the number of conjugated double bonds along the molecule.

Phytoene desaturases are iterative enzymes. Iterative enzymes carry out the same biochemical reaction multiple times on the same molecule, using the product of one reaction as the substrate for the following round of catalysis. The extent of the desaturation on the carotenoid backbone reflects the specificity, affinity, and catalytic efficiency of the enzyme for each intermediate.

Phytoene desaturases either introduce two double bonds in phytoene to produce γ-carotene, as in most plants and cyanobacteria, three double bonds to produce neurosporene, as in *Rhodobacter*, or four double bonds to produce lycopene, as in *Erwinia* and other photosynthetic bacteria. The product of the *Erwinia* phytoene desaturase (CrtI) is lycopene, a red carotenoid with 11 conjugated double bonds (FIG. 1). The Al-1 desaturase from *Neurospora crassa* introduces five double bonds into phytoene to synthesize 3,4-didehydrolycopene (DDHL). A desaturase capable of introducing six double bonds into phytoene would lead to the production of the fully-conjugated carotenoid 3,4,3',4'-tetradehydrolycopene, also known and bisdehydrolycopene.

Because the final product of the iterative activity of phytoene desaturase depends on the activity of each enzyme with a specific intermediate, it is hypothesized that mutations leading to changes in the peptide sequence of these enzymes may lead to altered specificity, either increasing or decreasing the number of successive desaturations.

Structural, genetic, and enzymatic studies have shown that phytoene is desaturated in a stepwise manner to lycopene (Goodwin, T. W., *Methods Enzym*, 214: 331–345 (1993)). The compounds phytofluene, ξ-carotene, neurosporene, and lycopene are successively formed by the removal of hydrogen atoms. The phytoene desaturase enzyme mediates this dehydrogenase-electron transferase activity. Thus, in the context of the present invention it will be appreciated that the present mutant CrtI polypeptides will have the ability to act on a variety of substrates including, but not limited to phytoene, phytofluene, ξ-carotene, neurosporene, and lycopene.

Carotenoid Biosynthesis

The present CrtI desaturase will be useful when incorporated into the carotenoid enzymatic pathways existing in various hosts. Several reviews discuss the genetics of carotenoid pigment biosynthesis (Armstrong, G., in *Comprehensive Natural Products Chemistry*, Elsevier Press, volume 2, pp 321–352 (1999); Lee, P., and Schimdt-Dannert, C., *Appl. Micrbiol Biotechnol.* 60(1–2):1–11 (2002)) with a focussed discussion on biosynthesis in plants and nutritional uses by Fraser, P. and Bramley, P. (supra). This pathway is extremely well studied in the Gram-negative, pigmented bacteria of the genera *Pantoea*, formerly known as *Erwinia*. In both *E. herbicola* EHO-10 (ATCC 39368) and *E. uredovora* 20D3 (ATCC 19321), the crt genes are clustered in two operons, crt Z and crt EXYIB (U.S. Pat. No. 5,656,472; U.S. Pat. No. 5,545,816; U.S. Pat. No. 5,530,189; U.S. Pat. No. 5,530,188; and U.S. Pat. No. 5,429,939). Despite the similarity in operon structure, the DNA sequences of *E. uredovora* and *E. herbicola* show no homology by DNA—DNA hybridization (U.S. Pat. No. 5,429,939). It should be noted that the former genus *Erwinia* has undergone substantial reclassification within the last few decades, following extensive analysis. The current classification of *Pantoea ananatis* (formerly *Erwinia uredovora*), *Pantoea stewartii* subsp. *stewartii* (formerly *Erwinia stewartii*), and *Pantoea agglomerans* (formerly *Erwinia herbicola*) are described in Mergaert et al. (*Int. J. Syst. Bacteriol.*, 43:162–173 (1993)).

It will be appreciated that for the present mutant crtI genes to be effective in the production of carotenoids, it will be necessary for the host cell to have suitable levels of isopentenyl pyrophosphate (IPP) within the cell. IPP levels may be increased by genetic manipulation of native or introduced genes. IPP may be synthesized through well-known acetate/mevalonate pathway. However, recent studies have demonstrated that the mevalonate-dependent pathway does not operate in all living organisms. An alternate mevalonate-independent for IPP biosynthesis has been characterized in bacteria and in green algae and higher plants (Horbach et al., *FEMS Microbiol. Lett.*, 111:135–140 (1993); Rohmer et al., *Biochem.*, 295: 517–524 (1993); Schwender et al., *Biochem.*, 316: 73–80 (1996); and Eisenreich et al., *PNAS USA*, 93: 6431–6436 (1996)).

Many steps in isoprenoid biosynthesis are known. For example, the initial steps of the alternate pathway involve the condensation of 3-carbons (private and C1 aldehyde group, D-glyceraldehyde 3-Phosphate), to yield 5-carbon compound (D-1-deoxyxylulose-5-phosphate). The dxs gene, encoding D-1-deoxyxylulose-5-phosphate synthase (Dxs), catalyzes the synthesis of D-1-deoxyxylulose-5-phosphate (FIG. 4).

Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (Dxr). The gene product of dxr that catalyzes the formation of 2-C-methyl-D-erythritol4-phosphate. Recently, dxr gene was renamed as ispC as a part of isp gene cluster (GenBank® Accession No. AAC73284).

Steps converting 2-C-methyl-D-erythritol-4-phosphate to isopentenyl monophosphate are not well characterized although some steps are known. 2-C-methyl-D-erythritol-4-phosphate is then converted into 4-diphosphocytidyl-2C-methyl-D-erythritol in a CTP dependent reaction by the enzyme encoded by non-annotated gene ygbP. Recently, ygbP gene was renamed as ispD as a part of isp gene cluster (SwissProt #Q46893) (FIG. 4).

Next, the 2nd position hydroxy group of 4-diphosphocytidyl-2C-methyl-D-erythritol can be phosphorylated in an ATP dependent reaction by the enzyme encoded by ychB gene. The ychB gene product phosphorylates 4-diphosphocytidyl-2C-methyl-D-erythritol resulting in 4-diphosphocytidyl-2C-methyl-D-erythritol 2-phosphate. Recently, ychB gene was renamed as ispE as a part of isp gene cluster (SwissProt #P24209).

The product of ygbB gene converts 4-diphosphocytidyl-2C-methyl-D-erythritol 2-phosphate to 2C-methyl-D-erythritol 2,4-cyclodiphosphate. 2C-methyl-D-erythritol 2,4-cyclodiphosphate can be further converted into carotenoids in carotenoid biosynthesis pathway. Recently, ygbB gene was renamed as ispF as a part of isp gene cluster (SwissProt #P36663). The reaction catalyzed by YgbP enzyme is carried out in CTP dependent manner.

The enzymes encoded by the lytB and gcpE genes (and perhaps others) are thought to participate in the reactions leading to formation of isopentenyl pyrophosphate (IPP) and dimethylallyl pyrophosphate (DMAPP). IPP may be isomerized to DMAPP via isopentenyl diphosphate isomerase (or "IPP isomerase"), encoded by the idi gene; however, this enzyme is not essential for survival and may be absent in some bacteria using the 2-C-methyl-D-erythritol 4-phosphate (MEP) pathway. Recent evidence suggests that the MEP pathway branches before IPP and separately produces IPP and DMAPP via the lytB gene product. Recently, lytB gene was renamed as ispH as a part of isp gene cluster (SwissProt #P62623). A lytB knockout mutation is lethal in *E. coli* except in media supplemented with both IPP and DMAPP.

The synthesis of FPP occurs via the isomerization of IPP to dimethylallyl pyrophosphate (DMAPP). This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule), respectively. Typically, the formation of phytoene represents the first step unique to biosynthesis of $C_{40}$ carotenoids (FIGS. 1 and 4). Phytoene itself is a colorless carotenoid and occurs via isomerization of IPP to dimethylallyl pyrophosphate (DMAPP) by isopentenyl pyrophosphate isomerase (encoded by the gene idi). The reaction is followed by a sequence of 3 prenyltransferase reactions in which geranyl pyrophosphate (GPP), farnesyl pyrophosphate (FPP), and geranylgeranyl pyrophosphate (GGPP) are formed. The gene crtE, encoding GGPP synthetase, is responsible for this latter reaction. Finally, two molecules of GGPP condense to form phytoene (PPPP), catalyzed by CrtB, encoding phytoene synthase.

Lycopene is a "colored" carotenoid produced from phytoene. Lycopene imparts the characteristic red color of ripe tomatoes and has great utility as a food colorant and antioxidant. It is also an intermediate in the biosynthesis of other carotenoids in some bacteria, fungi and green plants. Lycopene is prepared biosynthetically from phytoene through four sequential dehydrogenation reactions by the removal of eight atoms of hydrogen, catalyzed by the gene crtI (encoding phytoene desaturase). Intermediaries in this reaction are phytofluene, ζ-carotene, and neurosporene.

Lycopene cyclase (CrtY) converts lycopene to β-carotene. β-carotene is a typical carotene with a color spectrum ranging from yellow to orange. It is used as a colorant for margarine and butter, as a source for vitamin A production, and recently as a compound with potential preventative effects against certain kinds of cancers.

β-carotene is converted to zeaxanthin via a hydroxylation reaction resulting from the activity of β-carotene hydroxylase (encoded by the crtZ gene). For example, it is the yellow pigment which is present in the seeds of maize. Zeaxanthin is contained in feeds for hen or colored carp and is an important pigment source for their coloration.

In addition to the carotenoid biosynthetic genes and enzymes responsible for creation of phytoene, lycopene, β-carotene, and zeaxanthin, various other crt genes are known which enable the intramolecular conversion of $C_{40}$ compounds to produce numerous other functionalized carotenoid compounds by: (i) hydrogenation, (ii) dehydrogenation, (iii) cyclization, (iv) oxidation, (v) esterification/glycosylation, or any combination of these processes.

It is contemplated therefore that where a specific host cell does not have the genetic machinery to produce FPP or sufficient amounts of FPP, it is well within the grasp of the skilled person to obtain any members of the above described pathway and engineer these genes into the host to produce suitable amounts of the FPP.

Pathway Modulation

Knowledge of the sequence of the carotenoid biosynthesis genes will be useful in manipulating the carotenoid biosynthetic pathways in any organism having such a pathway. Methods of manipulating genetic pathways are common and well known in the art. Selected genes in a particularly pathway may be up-regulated or down-regulated by variety of methods. Additionally, competing pathways organism may be disrupted, eliminated or attenuated by similar techniques.

Once a key genetic pathway has been identified and sequenced, specific genes may be up-regulated to increase the output of the pathway. For example, additional copies of the targeted genes may be introduced into the host cell on multicopy plasmids such as pBR322. Alternatively, the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (U.S. Pat. No. 5,565,350; PCT/US93/03868).

Alternatively, it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.*, 171:46174622 (1989); Balbas et al., *Gene*, 136:211–213 (1993); Gueldener et al., *Nucleic Acids Res.*, 24:2519–2524 (1996); and Smith et al., *Methods Mol. Cell. Biol.*, 5:270–277(1996)).

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See, for example, Thomas D. Brock in Biotechnology: *A Textbook of Industrial Microbiology*, Second Edition (1989) Sinauer Associates, Inc., Sunderland, Mass. (Hereinafter "Brock"), or Deshpande, Mukund V., *Appl. Biochem. Biotechnol.*, 36:227 (1992) (Hereinafter "Deshpande").

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid molecule in the presence of the transposase, the transposable element will randomly insert into the nucleic acid molecule. The technique is useful for random mutageneis and for gene isolation, since the disrupted gene may be identified on the basis of the sequence of the transposable element. Kits for in vitro transposition are commercially available (see, for example, The Primer Island Transposition Kit, available from Perkin Elmer Applied Biosystems, Branchburg, N.J., based upon the yeast Ty1 element; The Genome Priming System, available from New England Biolabs, Beverly, Mass., based upon the bacterial transposon Tn7; and the EZ::TN Transposon Insertion Systems, available from Epicentre Technologies, Madison, Wis., based upon the Tn5 bacterial transposable element).

Within the context of the present invention, it may be useful to modulate the expression of the identified carotenoid pathway by any one of the above described methods. In the present invention a number of genes are provided which encode key enzymes in the carotenoid pathway leading to the production of pigments and smaller isoprenoid compounds.

Industrial Production

Where commercial production of TDHL is desired, a variety of culture methodologies may be applied. For example, large-scale production of a specific gene product, overexpressed from a recombinant microbial host, may be produced by both Batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Brock (supra) or Deshpande (supra), herein incorporated by reference.

Commercial production of the instant proteins and/or TDHL may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include, but are not limited to, monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, methane or methanol for which metabolic conversion into key biochemical intermediates (including in the production of carotenoids) has been demonstrated (U.S. Ser. No. 09/941, 947; hereby incorporated by reference). In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth* C1-Compd., [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.*, 153:485489 (1990)). Hence, it is contemplated that the source of carbon utilized in the present invention may encompass a wide variety of carbon containing substrates and will only be limited by the choice of organism.

DESCRIPTION OF THE PREFERRED EMBODIMENTS

Production of industrially-suitable amounts of tetradehydrolycopene is shown in the present invention. The carotenoid biosynthesis gene cluster was isolated from *Pantoea stewartii* (ATCC 8199) (Example 1). The isolated phytoene desaturase gene (crtI) was modified using error-prone PCR (Example 2). CrtI variants were assayed for their ability to produce increased amounts of TDHL. Caparisons between the wild type and variant phytoene desaturases of the present invention were conducted, illustrating the increased ability of the variants to produce TDHL. Preferred phytoene desaturase variants are those having the represented by the amino acid sequence of SEQ ID NO:18 (crtI-514 variant) and SEQ ID NO:20 (crtI-515 variant).

Tetradehydrolycopene production using the crtI variants was increased by chromosomally engineering a strong promoter upstream of various isoprenoid biosynthesis genes (Example 5). Preferred isoprenoid biosynthesis genes targeted for chromosomal promoter replacement include dxs, ispC, ispD, ispE, ispF, ispG, ispH, pyrG, idi, and ispA. More preferred as isoprenoid biosynthesis genes dxs, idi, and ispDF. Preferred microbial promoters suitable for driving the genes of the present invention include CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, $P_{T5}$, T7, tac, and trc (useful for expression in *Escherichia coli*) as well as the amy, apr, npr promoters and various phage promoters useful for expression in *Bacillus*. More preferred is the phage T5 promoter ($P_{T5}$) Increasing expression of isoprenoid biosynthesis genes resulted in isopentenyl pyrophosphate (IPP) synthesis.

The chromosomally-modified isoprenoid biosynthesis genes were integrated into a single strain using P1 transduction and trait stacking (Examples 6 and 7). Preferred transformed hosts are those comprising multiple promoter replacements on isoprenoid biosynthesis genes. More preferred are transformed hosts comprising promoter replacements to the idi, dxs, and ispDF genes (Example 7). Most preferred transformed hosts are *E. coli* strains comprising $P_{T5}$ promoter replacements to the idi, dxs, and ispDF genes.

Carotenoid biosynthesis genes useful for converting farnesyl pyrophosphate to various suitable carotenoid substrates were chromosomally-integrated into the transformed host cells (Examples 8 and 9). Preferred carotenoid biosynthesis genes include crtE, crtI and crtB. More preferred hosts are those comprising multiple chromosomally-integrated carotenoid biosynthesis genes. Even more preferred are hosts comprising both chromosomally-modified isoprenoid and carotenoid biosynthesis genes. Most preferred are *E. coli* strains comprising promoter modified isoprenoid genes dxs, idi, and ispDF and the carotenoid biosynthesis gene cluster $P_{T5}$-CrtEIB (Example 10). Optionally, no functional lycopene cyclase gene (crtY) should be present in the TDHL production host. For those production hosts which naturally harbor a functional lycopene cyclase, expression of the crtY gene should be disrupted or removed by methods known-in-the-art.

The tetradehydrolycopene produced in the present invention is preferably produced in the production host at levels exceeding 10% of the total carotenoids produced. More preferred is TDHL levels exceeding 20% of the total carotenoid produced by the cell. Most preferred host are those exhibiting TDHL levels exceeding 25% of the total carotenoids produced. In a further preferred embodiment, host cells producing at least 150 ppm TDHL are preferred (Example 11).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. In any case where GCG program parameters were not prompted for, in these or any other GCG program, default values were used.

The meaning of abbreviations is as follows: "h" means hour(s), "min" means minute(s), "sec" means second(s), "d" means day(s), "mL" means milliliters, "L" means liters, "μL" means microliters, "kB" means kilobase(s), "g" means grams, "μg" means micrograms, and "nm" means nanometers.

Example 1

Cloning of Genes from *Pantoea stewartii*

Because of the relatedness between *P. stewartii* and *E. uredovora*, *P. stewartii* carotenoid synthesis genes can be amplified by PCR using primers based on the published sequence of the *E. uredovora* crt genes (GenBank® Accession No. D90087, Misawa et al., J. Bacteriol., V172: 6704 (1990)). This was demonstrated previously for the crtE, crtB and crtI genes (Scolink and Bartley, *Plant Physiol.*, 108: 1343 (1995)). Using the same approach, primers were designed using the sequence from *Erwinia uredovora* to amplify a fragment by PCR containing the crt genes. These sequences included 5'-3':

```
ATGACGGTCTGCGCAAAAAAACACG      SEQ ID NO:13

GAGAAATTATGTTGTGGATTTGGAATGC   SEQ ID NO:14
```

Chromosomal DNA was purified from *Pantoea stewartii* (ATCC No. 8199) and Pfu Turbo polymerase (Stratagene, La Jolla, Calif.) was used in a PCR amplification reaction under the following conditions: 94° C., 5 min; 94° C. (1 min)60° C. (1 min)–72° C. (10 min) for 25 cycles, and 72° C. for 10 min. A single product of approximately 6.5 kb was observed following gel electrophoresis. Taq polymerase (Perkin Elmer) was used (10 min, 72° C. reaction) to add 3' adenosine nucleotides to the end of the PCR fragment which was then ligated into pCR4-TOPO vector (Invitrogen, Carlsbad, Calif.) to produce pPCB13. *E. coli* DH5α (Life Technologies, Rockville, Md.) was transformed by electroporation with the ligation mixture and bright yellow colonies were isolated. Their color indicated the production of a carotenoid compound. Following plasmid isolation as instructed by the manufacturer using the Qiagen (Valencia, Calif.) miniprep kit, the plasmid containing the 6.5 kb amplified fragment was transposed with pGPS1.1 using the GPS-1 Genome Priming System kit (New England Biolabs, Inc., Beverly, Mass.) A number of these transposed plasmids were sequenced from each end of the transposon. Sequence was generated on an ABI Automatic sequencer using dye terminator technology (U.S. Pat. No. 5,366,860; EP 272007) using transposon specific primers. Sequence assembly was performed with the Sequencher program (Gene Codes Corp., Ann Arbor, Mich.).

Example 2

Generation of Variant crtI Genes by Error-Prone PCR

In order to generate a phytoene desaturase with the ability to fully desaturate phytoene to TDHL, error-prone PCR was performed on the *P. stewartii* crtI gene (SEQ ID NO:7).

The oligonucleotides, crtI-F (ATGAAACCAACTACGG-TAA; SEQ ID NO: 15) and crtI-R (TCAAATCAGATCCTC-CAGC; SEQ ID NO: 16) corresponding to the ends of the crtI gene, were used to amplify the entire crtI gene using error-prone PCR. Eleven PCR reactions were set up, each containing a different concentration of MnCl$_2$ to increase the level of nucleotides mis-incorporated (indicated in Table 1) (Fromant et al., *Anal Biochem*, 224(1):347–53 (1995); Lin-Goerke et al., *Biotechniques*, 23(3):409–12 (1997)).

TABLE 1

Error-Prone PCR Reaction Components

| | \multicolumn{11}{c}{Component (μL)} | | | | | | | | | | |
|---|---|---|---|---|---|---|---|---|---|---|---|
| | 1 | 2 | 3 | 4 | 5 | 6 | 7 | 8 | 9 | 10 | 11 |
| 10x buffer | 10 | 10 | 10 | 10 | 10 | 10 | 10 | 10 | 10 | 10 | 10 |
| 25 mM MgCl2 | 1 | 1 | 1 | 1 | 1 | 1 | 1 | 1 | 1 | 1 | 1 |
| 1 mM MnCl2 | 0 | 1 | 2 | 3 | 4 | 5 | 7.5 | 10 | 15 | 20 | 25 |
| Primers each (10 μM) | 1 | 1 | 1 | 1 | 1 | 1 | 1 | 1 | 1 | 1 | 1 |
| template DNA (1 pM) | 1 | 1 | 1 | 1 | 1 | 1 | 1 | 1 | 1 | 1 | 1 |
| Water | 77 | 76 | 75 | 74 | 73 | 72 | 69.5 | 67 | 62 | 57 | 52 |
| dNTPs (2.5 mM each) | 8 | 8 | 8 | 8 | 8 | 8 | 8 | 8 | 8 | 8 | 8 |
| Taq polymerase | 1 | 1 | 1 | 1 | 1 | 1 | 1 | 1 | 1 | 1 | 1 |
| Total volume (μl) | 100 | 100 | 100 | 100 | 100 | 100 | 100 | 100 | 100 | 100 | 100 |
| MnCl2 concentration (μM) | 0 | 10 | 20 | 30 | 40 | 50 | 75 | 100 | 150 | 200 | 250 |

Products of the eleven error-prone PCR amplifications were cloned in the pTrcHis2-TOPO vector (Invitrogen) and the resulting constructs transferred to *E. coli* TOP10 cells (Invitrogen). Transformants were spread on LB-Amp plates. After an overnight incubation, the plasmids carrying the mutagenized crtI genes were isolated from the pooled colonies. This plasmid pool was used to transform an *E. coli* MG1655 strain containing the pDCQ51 plasmid. This plasmid carried a Tn5 transposon cassette in the crtY lycopene cyclase gene of pCRT1 and directs the production of lycopene. Colonies of pDCQ51 cells are pink. The pCRT1 construct was formed by cloning of the entire crt gene cluster of *P. stewartii*, obtained as described in Example 1, to the EcoRI site of broad host range cloning vector pBHR1 (MoBiTec, Goettingen, Germany) such that expression of the genes of the crt operon was controlled by the promoter of the chloramphenicol resistance gene. An unexpected large proportion of the transformants (more than 2%) exhibited a deeper pink color from that of the control pDCQ51 colonies. Ten of these colonies were cultured in liquid media in order to isolate the carotenoids formed. The UV-Visible absorbance spectra of acetone extracts from the cells pellets of these cultures were recorded between 300 to 600 nm. Several of these transformants exhibited a shoulder around 540 nm, a longer wavelength absorbance than that of the lycopene absorption peaks (444, 470 and 502 nm) that indicated some tetradehydrolycopene had been formed.

The pTrcHis2-TOPO plasmids carrying the variant crtI genes from two transformants, DPR 514 and DPR515, which produced tetradehydrolycopene were isolated and the inserts sequenced. Sequencing of pTrcHis2 CrtI-514 from DPR 514 crtI variant (SEQ ID NO:17) indicated that five nucleotide bases were different in this sequence as compared to the *P. stewartii* crtI wild-type sequence. These five base changes resulted in three amino acid changes in the deduced amino acid sequence of crtI-514 (SEQ ID NO:18) which were leucine residue 28 to serine, threonine residue 84 to serine, and lysine residue 138 to glutamate. The pTrcHis2 CrtI-515 from DPR515 crtI sequence (SEQ ID NO:19) contained seven nucleotide base changes from the wild-type *P. stewartii* crtI sequence. These resulted in only one change in the deduced amino acid sequence of crtI-515 (SEQ ID NO:20) where a leucine at residue 81 was changed to methionine.

Example 3

Shake-Flasks Production of Tetradehydrolycopene in a Crt+ cells

*E. coli* strains DPR514 and DPR515 were grown in 100 mL of Luria-Bertani (LB) medium containing 50 μg/mL kanamycin and 100 μg/mL ampicillin at 27° C. for 24 hr. The cells were harvested by centrifugation, extracted with acetone, the acetone was evaporated and the carotenoid containing residue resuspended in methanol in preparation HPLC analysis. The formation of 18–22% of the carotenoid in the form of tetradehydrolycopene was observed as shown in Table 2. The remainder of the carotenoid formed in these strains was lycopene.

A Beckman System Gold® HPLC with Beckman Gold Nouveau Software (Columbia, Md.) was used for the study. A sample of 0.1 mL of the crude acetone extraction was loaded onto a 25 cm×4.6 mm Discovery® C18 (5 μm particles) column with corresponding guard column from Supelco (Bellefonte, Pa.). The flow rate was 2 mL/min. Two Buffers were used. Buffer A was 100% Acetonitrile, buffer B was 100% Acetone. Solvent program was: 0–20 min linear gradient of 100% buffer A to 40% buffer A. 20–25 min 100% buffer A. The spectrum data was collected by Beckman photodiode array detector (model 168) and is presented in FIG. 8.

TABLE 2

Tetradehydrolycopene formed in E. coli

| Strain | peak 1 time | peak 1 component | peak 1 area % | peak 2 time | peak 2 component | peak 2 area % |
|---|---|---|---|---|---|---|
| DPR514 | 7.88 | tetradehydrolycopene | 18.3 | 9.75 | lycopene | 69.7 |
| DPR515 | 7.80 | tetradehydrolycopene | 22.3 | 9.62 | lycopene | 67.43 |

Example 4

Production of Tetradehydrolycopene in Crtl[31] Cells

Production of tetradehydrolycopene from was also investigated in a cell background lacking endogenous Crtl activity.

Plasmid pDCQ52 was constructed by insertion of a Tn5 transposon in the crtl coding sequence of the plasmid pBHR-crt+using the EZ::TN Transposon Insertion System (Epicentre Technologies, Madison, Wis.). Colonies of cells containing plasmid pDCQ52 are colorless and accumulate phytoene. The pBHR-crt+ was constructed by cloning the carotenoid gene cluster amplified in Example 1 into the EcoRI site of pBHR1 (MoBiTec, Goettingen, Germany) such that the crt genes were expressed from the chloramphenicol resistance gene promoter.

Plasmids pTrcHis2 Crtl-514 and pTrcHis2 Crtl-515 carrying mutagenized crtl genes were each transferred along with pDCQ52 into E. coli DH10B (Invitrogen) by electroporation, yielding E. coli strains DPR 589 and DPR 588, respectively.

To investigate the effect of overexpression of the wild-type crtl gene from the multicopy pTrcHis2-TOPO vector, the P. stewartii wild-type crtl gene was cloned into pTrcHis2-TOPO from a DNA product amplified by PCR using the crtl-F (SEQ ID NO:15) and crtl-R (SEQ ID NO:16) primers with P. stewartii chromosomal DNA as template. The resulting plasmid pTrcHis2-Crtl was transferred along with pDCQ52 into E. coli DH10B by electroporation, yielding E. coli strains DPR 571.

Strains DPR 571, DPR 588 and DPR 589 were grown in shake-flasks and their carotenoids analyzed as described in Example 3. As shown in Table 3, overexpression of wild-type Crtl resulted in a low level of tetradehydrolycopene synthesis. However, the fraction of tetradehydrolycopene is greatly increased by overexpression of the variant crtl genes.

TABLE 3

Tetradehydrolycopene Formation by Wild-type and Variant ctrl

| strain | % lycopene | % tetradehydrolycopene |
|---|---|---|
| DPR 571 (E. coli DH10B pTrcHis2-Crtl) | 96 | 4 |
| DPR 589 (E. coli DH10B pTrcHis2 Crtl-514) | 86 | 14 |
| DPR 588 (E. coli DH10B pTrcHis2Crtl-515) | 89 | 11 |

Example 5

Construction of E. coli Strains with the Phage T5 Strong Promoter Chromosomally Integrated Upstream of Isoprenoid Genes The native promoters of the E. coli isoprenoid genes, dxs, idi, ispDispF, and ispAdxs, (FIG. 4) were replaced with the phage T5 ($P_{T5}$) strong promoter using the "two PCR-fragments" chromosomal integration method as shown in FIG. 5. The method for replacement is based on homologous recombination via the λ Red recombinase encoded on a helper plasmid. Recombination occurs between the E. coli chromosome and two PCR fragments that contain 20–50 bp homology patches at both ends of PCR fragments (FIG. 5). For integration of the T5 strong promoter upstream of these genes, a two-PCR-fragment method was employed. In this method, the two fragments were comprised of a linear DNA fragment (1489 bp) containing a kanamycin selectable marker flanked by site-specific recombinase target sequences (FRT) and a linear DNA fragment (154 bp) containing a phage T5 promoter ($P_{T5}$; SEQ ID NO:52) comprising the −10 and −35 consensus promoter sequences, lac operator (lacO), and a ribosomal binding site (RBS).

By using the two PCR fragment method, the kanamycin selectable marker and phage T5 promoter (kan-$P_{T5}$) were integrated upstream of the dxs, idi, ispDF and ispAdxs genes, yielding kan-$P_{T5}$-dxs, kan-$P_{T5}$-idi, kan-$P_{T5}$-ispDF, and kan-$P_{T5}$-ispAdxs. The linear DNA fragment (1489 bp) which contained a kanamycin selectable marker, flanked by site-specific recombination sequences, was synthesized by PCR from plasmid pKD4 (Datsenko and Wanner, PNAS., 97:6640–6645 (2000)) with primer pairs as follows in Table 4.

TABLE 4

Primers for Amplification of the Kanamycin Selectable Marker

| Primer Name | Primer Sequence | SEQ ID NO: |
|---|---|---|
| 5'-kan(dxs) | TGGAAGCGCTAGCGGACTACATCATCCAGCGTAA TAAATAACGTCTTGAGCGATTGTGTAG[1] | 21 |
| 5'-kan(idi) | TCTGATGCGCAAGCTGAAGAAAAATGAGCATGGA GAATAATATGACGTCTTGAGCGATTGTGTAG[1] | 22 |
| 5'-kan(ispDF) | GACGCGTCGAAGCGCGCACAGTCTGCGGGGCAA AACAATCGATAACGTCTTGAGCGATTGTGTAG[1] | 23 |
| 5'-kan(ispAdxs) | ACCATGACGGGGCGAAAAATATTGAGAGTCAGAC ATTCATGTGTAGGCTGGAGCTGCTTC[1] | 24 |
| 3'-kan | GAAGACGAAAGGGCCTCGTGATACGCCTATTTTTA TAGGTTATATGAATATCCTCCTTAGTTCC[2] | 25 |

[1]The underlined sequences illustrate each respective homology arm chosen to match sequences in the upstream region of the chromosomal integration site, while the remainder is the priming sequence)
[2]The underlined sequences illustrate homology arm chosen to match sequences in the 5'-end region of the T5 promoter DNA fragment The second linear DNA fragment (154 bp) containing a phage T5 promoter was synthesized by PCR from pQE30 (QIAGEN, Inc., Valencia, Calif.) with primer pairs as follows in Table 5.

TABLE 5

Primers for Amplification of the T5 Promoter

| Primer Name | Primer Sequence | SEQ ID NO: |
|---|---|---|
| 5'-T5 | CTAAGGAGGATATTCATATAACCTATAAAAATAGGC GTATCACGAGGCCC[1] | 26 |
| 3'-T5(dxs) | GGAGTCGACCAGTGCCAGGGTCGGGTATTTGGCAA TATCAAAACTCATAGTTAATTTCTCCTCTTTAATG[2] | 27 |
| 3'-T5(idi) | TGGGAACTCCCTGTGCATTCAATAAAATGACGTGTT CCGTTTGCATAGTTAATTTCTCCTCTTTAATG[2] | 28 |
| 3'-T5(ispDF) | CGGCCGCCGGAACCACGGCGCAAACATCCAAATGA GTGGTTGCCATAGTTAATTTCTCCTCTTTAATG[2] | 29 |
| 3'-T5(ispAdxs) | CCTGCTTAACGCAGGCTTCGAGTTGCTGCGGAAAG TCCATAGTTAATTTCTCCTCTTTAATG[2] | 30 |

[1]The underlined sequences illustrate homology arm chosen to match sequences in the 3'-end region of the kanamycin DNA fragment
[2]The underlined sequences illustrate each respective homology arm chosen to match sequences in the downstream region of the chromosomal integration site Standard PCR conditions were used to amplify the linear DNA fragments with AmpliTaq Gold® polymerase (Applied Biosystems, Foster City, Calif.) as follows:

| PCR reaction: | PCR reaction mixture: |
|---|---|
| Step1 94° C. 3 min | 0.5 μL plasmid DNA |
| Step2 93° C. 30 sec | 5 μL 10X PCR buffer |
| Step3 55° C. 1 min | 1 μL dNTP mixture (10 mM) |

-continued

| PCR reaction: | PCR reaction mixture: |
|---|---|
| Step4 72° C. 3 min | 1 μL 5'-primer (20 μM) |
| Step5 Go To Step2, 30 cycles | 1 μl 3'-primer (20 μM) |
| Step6 72° C. 5 min | 0.5 μL AmpliTaq Gold ® polymerase |
| | 41 μL sterilized dH$_2$O |

After completing the PCR reactions, 50 μL of each PCR reaction mixture was run on a 1% agarose gel and the PCR products were purified using the QIAquick Gel Extraction Kit™ as per the manufacturer's instructions (Cat. # 28704, QIAGEN). The PCR products were eluted with 10 μL of distilled water. The DNA Clean & Concentrator™ kit (Zymo Research, Orange, Calif.) was used to further purify the PCR product fragments as per the manufacturer's instructions. The PCR products were eluted with 6–8 μL of distilled water to a concentration of 0.5–1.0 μg/μL.

The $E.\ coli$ MC1061 strain, carrying a λ Red recombinase expression plasmid pKD46 (amp$^R$) (Datsenko and Wanner, supra; SEQ ID NO:50), was used as a host strain for the chromosomal integration of the PCR fragments. The strain was constructed by transformation of $E.\ coli$ strain MC1061 with the λ Red recombinase expression plasmid, pKD46 (amp$^R$). The λ-Red recombinase in pKD46 is comprised of three genes exo, bet, and gam expressed under the control of an arabinose-inducible promoter. Transformants were selected on 100 μg/mL of ampicillin LB plates at 30° C.

For transformation, electroporation was performed using 5–10 μg of the purified PCR products carrying the kanamycin marker and phage T5 promoter. Approximately one-half of the cells transformed were spread on LB plates containing 25 μg/mL of kanamycin in order to select antibiotic-resistant transformants. After incubating the plate at 37° C. overnight, antibiotic-resistance transformants were selected as follows: 10 colonies of kan-$P_{T5}$-dxs, 12 colonies of kan-$P_{T5}$-idi, 10 colonies of kan-$P_{T5}$-ispDF, and 19 colonies of kan-$P_{T5}$-ispAdxs.

PCR analysis was used to confirm the integration of both the kanamycin selectable marker and the phage T5 promoter ($P_{T5}$)(SEQ ID NO:52) in the correct location on the $E.\ coli$ chromosome. For PCR, a colony was resuspended in 50 μL of PCR reaction mixture containing 200 μM dNTPs, 2.5 U AmpliTaq™ (Applied Biosytems), and 0.4 μM of specific primer pairs. Test primers were chosen to match sequences of the regions located in the kanamycin (5'-primer) and the early coding-region of each isoprenoid gene (3'-primer). The PCR reaction was performed as described in above. The resultant $E.\ coli$ strains carrying each kan-$P_{T5}$-isoprenoid gene fusion on the chromosome were used for stacking multiple kan-$P_{T5}$-isoprenoid gene fusions on the chromosome to construct $E.\ coli$ strain for increasing carotenoid production.

Example 6

Construction of $E.\ coli$ $P_{T5}$-dXs $P_{T5}$-idi Strain

In order to characterize the effect of the chromosomal integration of T5 strong promoter in the front of the dxs and idi genes on β-carotene production, a strain, $E.\ coli$ $P_{T5}$-dxs $P_{T5}$-idi, capable of producing β-carotene, was constructed.

P1 lysate was made with the $E.\ coli$ kan-$P_{T5}$-dxs strain was transduced into the recipient strain, $E.\ coli$ MG1655 containing a β-carotene biosynthesis expression plasmid pPCB15 (cam$^R$) (SEQ ID NO:49). The pPCB15 plasmid was constructed from ligation of SmaI digested pSU18 (Bartolome et al., $Gene$, 102:75-78 (1991)) vector with a blunt-ended PmeI/NotI fragment carrying crtEXYIB from pPCB13 (Example 1). The lysate of the $E\ coli$ kan-$P_{T5}$-dxs strain was prepared by infecting a growing culture of bacteria with the P1 phage and allowing the cells to lyse. For P1 infection, $E.\ coli$ kan-$P_{T5}$-dxs strain was inoculated in 4 mL LB medium with 25 μg/mL of kanamycin, grown at 37° C. overnight, and then sub-cultured with 1:100 dilution of an overnight culture in 10 mL LB medium containing 5 mM CaCl$_2$. After 20–30 min of growth at 37° C., $10^7$ p1$_{vir}$ phage particles were added. The cell-phage mixture was aerated for 2–3 hr at 37° C. until lysed. Several drops of chloroform were added and the mixture vortexed for 30 sec and incubated for an additional 30 min at room temp. The mixture was then centrifuged for 10 min at 4500 rpm and the supernatant transferred into a new tube to which several drops of chloroform were added.

Sixteen kanamycin-resistance transductants were selected. The kanamycin selectable marker was eliminated from the chromosome of the transductant using a FLP recombinase expression system. To eliminate kanamycin selectable marker from the chromosome, a FLP recombinase expression plasmid pCP20 (amp$^R$) (ATCC PTA-4455; Cherepanov and Wackernagel, $Gene$, 158:9–14 (1995)), which has a temperature-sensitive replication of origin, was transiently transformed into one of the kanamycin-resistant transductants by electroporation. Cells were spread onto LB agar containing 100 μg/mL of ampicillin and 25 μg/mL of chloramphenicol plates and grown at 30° C. for 1 day. Colonies were picked and streaked on 25 μg/mL of chloramphenicol LB plates without ampicillin antibiotics and incubated at 43° C. overnight. Plasmid pCP20 has a temperature sensitive origin of replication and was cured from the host cells by culturing them at 43° C. The colonies were tested for ampicillin and kanamycin sensitivity to test loss of pCP20 and the kanamycin selectable marker by streaking colonies on 100 μg/mL of ampicillin LB plate or 25 μg/mL of kanamycin LB plate yielding $E.\ coli$ $P_{T5}$-dxs strain.

In order to stack kan-$P_{T5}$-idi on chromosome of $E.\ coli$ $P_{T5}$-dxs, P1 lysate made on $E.\ coli$ kan-$P_{T5}$-idi strain was transduced into the recipient strain, $E.\ coli$ $P_{T5}$-dxs, as described above. Approximately 450 kanamycin-resistance transductants were selected. After transduction, the kanamycin selectable marker was eliminated from the chromosome as described above, yielding $E.\ coli$ $P_{T5}$-dxs $P_{T5}$-idi strain.

For the $E.\ coli$ $P_{T5}$-dxs $P_{T5}$-idi strain, the correct integration of the phage T5 promoter upstream of dxs and idi genes on the $E.\ coli$ chromosome and elimination of the kanamycin selectable marker were confirmed by PCR analysis. A colony of the $E.\ coli$ $P_{T5}$-dxs $P_{T5}$-idi strain was tested by PCR with different combination of specific primer pairs, T-kan (SEQ ID NO:31) and B-dxs (SEQ ID NO:32), T-T5 (SEQ ID NO:33) and B-dxs, T-kan and B-idi(SEQ ID NO:34), T-T5 and B-idi. Test primers were chosen to amplify regions located either in the kanamycin or the phage T5 promoter and the downstream region of the chromosomal integration site as shown on FIG. 7. The PCR reaction was performed as described in Example 5. The PCR results indicated the elimination of the kanamycin selectable marker from the $E.\ coli$ chromosome. The chromosomal integration of the phage T5 promoter fragment upstream of the dxs and idi gene was confirmed based on the expected sizes of PCR products, 229 bp and 274 bp, respectively.

Example 7

Construction of $E.\ coli$ $P_{T5}$-dxs $P_{T5}$-idi $P_{T5}$-ispDF

In order to create a bacterial strain capable of increased carotenoid production, the $P_{T5}$-ispDF gene was further stacked into the $E.\ coli$ $P_{T5}$-dxs $P_{T5}$-idi strain by P1 transduction in combination with the FLP recombination system. P1 lysate was with $E.\ coli$ kan-$P_{T5}$-ispDF strain was transduced into the recipient strain, $E.\ coli$ $P_{T5}$-dxs $P_{T5}$-idi containing a p-carotene biosynthesis expression plasmid pPCB15 (cam$^R$), as described in Example 6. Twenty-one kanamycin-resistance transductants were selected. The kanamycin selectable marker was eliminated from the chromosome of the transductant using a FLP recombinase expression system as described above, yielding E. coli $P_{T5}$-dxs $P_{T5}$-idi $P_{T5}$-iSPDF strain.

For the E. coli $P_{T5}$-dxs $P_{T5}$-idi $P_{T5}$-ispDF strain, the correct integration of the phage T5 promoter upstream of dxs, idi, and ispDF genes on the E. coli chromosome and elimination of the kanamycin selectable marker were confirmed by PCR analysis. A colony of the E. coli $P_{T5}$-dxs $P_{T5}$-idi $P_{T5}$-ispDF strain was tested by PCR with different combination of specific primer pairs, T-kan (SEQ ID NO:31) and B-dxs(SEQ ID NO:32), T-T5 (SEQ ID NO:33) and B-dxs, T-kan and B-idi(SEQ ID NO:34), T-T5 and B-idi, T-kan and B-ispDF (5'-CCAGCAGCGCATGCACCGAGT-GTTC-3'; SEQ ID NO:35), T-T5 and B-ispDF. Test primers were chosen to amplify regions located either in the kanamycin or the phage T5 promoter and the downstream region of the chromosomal integration site. The PCR reaction was performed as described in Example 5. The PCR results indicated the elimination of the kanamycin selectable marker from the E. coli chromosome. The chromosomal integration of the phage T5 promoter fragment upstream of the dxs, idi, and ispDF genes was confirmed based on the expected sizes of PCR products, 229 bp, 274 bp, and 296 bp, respectively.

Example 8

Chromosomal Integration of the P. stewartii crtE Gene in E. coli

This example describes the chromosomal integration of P. stewartii crtE and crtlB genes into the inter-operon region located at 81.2 min of E. coli chromosome by integration of P. stewartii crtE and P. stewartii crtlB. The crtE, crtl, and crtB genes encode geranylgeranyl pyrophosphate synthase, phytoene dehydrogenase, and phytoene synthase, respectively.

The linear DNA fragment containing fused kanamycin selectable marker-phage T5 promoter was synthesized by PCR from psUH5 (SEQ ID NO:51) with primer pairs, T1(crtE) (5'-AGCCGTCGCAGGAGGAACAACTCATATCATCATT GCGATCTCGACCG TCTTGAGCGATTGTGTAG-3'; SEQ ID NO:36) which contains a h10 homology arm (underlined, 45 bp) chosen to match a sequence in the inter-operon region located at 81.2 min of *E. coli* chromosome and a priming sequence (20 bp) and B1(crtE) (5'-TGAACGTGTTTTTTTGCGCAGACCGTCATAGTTA ATTTCTCCTCTTTA ATG-3'; SEQ ID NO:37) which contains an h11 homology arm (underlined, 29 bp) chosen to match a sequence in the downstream region of the crtE start codon and a priming sequence (22 bp). The linear DNA fragment containing *P. stewartii* crtE gene was synthesized by PCR from pPCB15 (SEQ ID NO:49) with primer pairs, T2(crtE) (5'-ACAGAATTCATTAAAGAGGAGAAATTAACTATGA CGGTCTGCGCAAA AAAACACG-3'; SEQ ID NO:38) which contains an h8 homology arm (underlined, 30 bp) chosen to match a sequence in the 3'-end region of the fused kanamycin selectable marker-phage T5 promoter and a priming sequence (25 bp) and B2(crtE) (5'-AGAATGACCAGCTGGATGCATTATCTTTATTTGGAT CATTGAGGGTTA ACTGACGGCAGCGAGTT-3'; SEQ ID NO:39) which contains an h12 homology arm (underlined, 45 bp) chosen to match a sequence in the inter-operon region located at 81.2 min of the *E. coli* chromosome and a priming sequence (20 bp)(FIG. 6). The underlined sequences illustrate each respective homology arm, while the remainder is the priming sequences for hybridization to complementary nucleotide sequences on the template DNA for the PCR reaction. The two resultant PCR fragments were the fused kanamycin selectable marker-phage T5 promoter containing the homology arms (h10 and h11) and the *P. stewartii* crtE gene containing the homology arms (h8 and h12) as illustrated in FIG. 6.

The PCR amplification, purification, and electro-transformation were performed as in Example 5 except that the transformation of the reporter plasmid pPCB15 into *E coli*. strain was omitted. Both fused kanamycin marker-phage T5 promoter PCR products (5–10 μg) and the *P. stewartii* crtE PCR products (5–10 μg) were co-transformed into an *E. coli* host strain (MC1061) expressing the λ-Red recombinase system by electroporation. Transformants were selected on 25 g/mL of kanamycin LB plates at 37° C. After incubating the plate at 37° C. overnight, two kanamycin ($kan^R$) transformants were selected.

Two $kan^R$ transformants were analyzed by PCR with T10 (5'-CCATGACCCTACATTGTGATCTATAG-3'; SEQ ID NO:40) and T13 (5'-GGAACCATTGAACTGGACCCTMCG-3'; SEQ ID NO:41) primer pair. PCR analysis was performed under same PCR reaction condition as described in Example 5. PCR testing with T10/T13 on two transformants exhibited the expected size, 2883 bp, based on a 1% agarose gel. The result indicated the correct integration of the fused kanamycin selectable marker-phage T5 promoter DNA fragment along with *P. stewartii* crtE gene into the inter-operon region located at 81.2 min of *E. coli* chromosome, yielding *E. coli* kan-$P_{T5}$-crtE.

Example 9

Chromosomal Integration of the *P. stewartii* crtl and crtB Genes in *E. coli* $P_{T5}$-crtE for Construction of *E. coli* $P_{T5}$-crtEIB The linear DNA fragment containing the fused kanamycin selectable marker-phage T5 promoter-*P. stewartii* crtE gene was synthesized by PCR from the genomic DNA of *E. coli* kan-$P_{T5}$-crtE with primer pairs, T10 (SEQ ID NO:40) which contains a priming sequence (26 bp) corresponding to the 162 bases in the upstream region of the integration site of the fused kanamycin selectable marker-phage T5 promoter-crtE gene in *E. coli* and B1(crtlB) (5'-TCCTCCAGCATTAAGCCTGCCGTCGCCTTTTAACT GACGGCAGCG AGTTTTTTGTC-3'; SEQ ID NO:42) which contains an h13 homology arm (underlined, 29 bp) chosen to match sequences in the downstream region of the crt/start codon and a priming sequence (27 bp)(FIG. 6). The linear DNA fragment containing *P. stewartii* crtlB gene was synthesized by PCR from pPCB15 (SEQ ID NO:49) with primer pairs, T2(crtlB) (5'-TTTGACAAAAAACTCGCTGCCGTCAGTTAAAAGG CGACGGCAGGCTT AATGCTG-3'; SEQ ID NO:43) which contains an h14 homology arm (FIG. 6) (underlined, 30 bp) chosen to match a sequence in the 3'-end region of the fused kanamycin selectable marker-phage T5 promoter-crtE gene and a priming sequence (24 bp) and B2(crtlB) (5'-AGAATGACCAGCTGGATGCATTATCTTTATTTGGAT CATTGAGGGCTA GATCGGGCGCTGCCAGA-3'; SEQ ID NO:44) which contains an h12 homology arm (underlined, 45 bp) (FIG. 6) chosen to match a sequence in the inter-operon region located at 81.2 min of the *E. coli* chromosome and a priming sequence (20 bp). The underlined sequences illustrate each respective homology arm, while the remainder is the priming sequences for hybridization to complementary nucleotide sequences on the template DNA for the PCR reaction. The two resultant PCR fragments were the fused kanamycin selectable marker-phage T5 promoter-*P. stewartii* crtE gene containing the homology region (162 bp) at the 5'-end and homology arm (h13), and the *P. stewartii* crtIB genes containing the homology arms (h14 and h12) as illustrated in FIG. 6.

The PCR amplification, purification, and electro-transformation were performed as described above except for the omission of transforming the host cell with the reporter plasmid, pPCB15. Both the fused kanamycin selectable marker-phage T5 promoter-*P. stewartii* crtE gene PCR products (5–10 μg) and the *P. stewartii* crtIB PCR products (5–10 μg) were co-transformed into an *E. coli* host cell expressing the λ-Red recombinase system by electroporation as previously described. Transformants were selected on 25 μg/mL of kanamycin LB plates at 37° C. After incubating the plate at 37° C. overnight, one kanamycin resistant transformant was selected. The kanamycin selectable marker was eliminated as described in Example 6.

The selected transformant was PCR analyzed with different combinations of specific primer pairs, T10 and T2 (5'-CAGTCATAGCCGAATAGCCT-3'; SEQ ID NO:45), T2(T5) (5'-CGGTGCCCTGAATGAACTGC-3'; SEQ ID NO:46) and T12 (5'-CTAGATCGGGCGCTGCCA-GAGATGA-3'; SEQ ID NO:47), T11(5'-ACACGTTCAC-CTTACTGGCATTTCG-3'; SEQ ID NO:48) and T13, and T10 and T13. Test primers were chosen to amplify sequences located either in the vicinity of the integration region of the kanamycin selectable marker-phage T5 promoter-crtE fragment or the crtIB genes as shown on FIG. 7. PCR analysis was performed under same PCR reaction condition as described in Example 5. PCR test with T10 and T2, T2(T5) and T12, T11 and T13, and T10 and T13 exhibited the expected sizes, 676 bp, 3472 bp, 3478 bp and 5288 bp on 1% agarose gel, respectively. The elimination of the kanamycin selectable marker was confirmed by PCR fragment analysis. PCR fragment analysis with primer pair T10 and T2 exhibited no product formation as expected. PCR analysis with primer pairs T2(T5) and T12, T 11 and T13, and T10 and T13 exhibited the expected PCR product sizes of 3472 bp, 3478 bp, and 3895 bp on 1% agarose gel, respectively. The results indicated the correct integration of the fused phage $P_{T5}$ promoter-*P. stewartii* crtE gene DNA fragment and *P. stewartii* crtIB genes into the inter-operon region located at 81.2 min of *E. coli* chromosome, yielding *E. coli* $P_{T5}$-crtEIB.

The functional expression of the constructed *E. coli* $P_{T5}$-crtEIB was tested by the synthesis of lycopene based on the production of pink pigment. After extracting lycopene with acetone as described in Example 3, the lycopene production by *E. coli* $P_{T5}$-crtEIB strain also was confirmed by measuring the spectra of lycopene with its characteristic $\lambda_{max}$ peaks at 444, 470 and 502 nm.

Example 10

Production of Tetradehydrolycopene in

E. coli $P_{T5}$-dxs, $P_{T5}$-idi, $P_{T5}$-ispDF $P_{T5}$-crtEIB

*E. coli* $P_{T5}$-dxs, $P_{T5}$-idi, $P_{T5}$-ispDF, $P_{T5}$-crtEIB was constructed by P1 transduction in combination with the FLP recombination system. P1 lysate from the *E. coli* kan-$P_{T5}$-crtEIB strain was transduced into the recipient strain, *E. coli* $P_{T5}$-dxs $P_{T5}$-idi, $P_{T5}$ ispDF as described in Example 6. Sixteen kanamycin-resistance transductants were selected. The kanamycin selectable marker was eliminated from the chromosome of the transductant using a FLP recombinase expression system as described above, yielding *E. coli* $P_{T5}$-dxs $P_{T5}$-idi $P_{T5}$-ispDF $P_{T5}$-crtEIB strain (WS156). WS156 (MG1655 $P_{T5}$-dxs, $P_{T5}$-idi, $P_{T5}$-ispDF, $P_{T5}$-crtEIB) exhibited darker pink color and produced much more lycopene since it also contained additional copies of upstream isoprenoid pathway genes on the chromosome that increased the flux of carotenoid synthesis. WS156 (Kan$^s$) was thus chosen as the host for tetradehydrolycopene production. Plasmid pTrcHis2-crtI-515, expressing a mutated crtI gene on pTrcHis2, was transformed into WS156 (Kan$^s$) and transformants were selected on plates with 100 μg/mL ampicillin. Cells were grown in 100 mL TB (Terrific Broth) shaking at 37° C. for 20 hours and harvested by centrifugation. Cell pellets were extracted with acetone and analyzed by HPLC as described previously. WS156 (Kan$^s$) host alone produced only one pigment that eluted at 11.6 min with absorption spectra as 447 nm, 470 nm, and 502 nm. This is identical to that of the authentic lycopene standard. WS156 (Kan$^s$) containing pTrcHis2-crtI-515 produced two major pigments. The new peak, comprising 44% of the total pigments, eluted at 10.2 min with absorption spectra as 485 nm, 509 nm, 543 nm. This spectra is consistent with that of tetradehydrolycopene. The other peak that eluted at 11.6 min was lycopene.

Example 11

Production of Tetradehydrolycopene By Fermentation

The plasmids pTrcHis2-CrtI-515 and pDCQ51 were transferred by electroporation into *E. coli* $P_{T5}$-dxs, $P_{T5}$-idi, $P_{T5}$-ispDF (WS140), resulting in the *E. coli* strain DPR646.

DPR646 was pre-cultured for seeding a fermentor in 500 mL of 2×YT medium (10 g/L yeast extract, 16 g/L tryptone, 10 g/L NaCl and 20 g/L glucose) in a 2 L Erlenmeyer flask, containing 100 mg/mL ampicillin and 50 mg/mL kanamycin. The seed culture was started from a single colony on LB agar +100 mg/mL ampicillin and 50 mg/mL kanamycin. The seed culture was grown at 35° C. in a shaker at 300 rpm until an absorbance at 550 nm of 4–8 was reached. This initial culture was used to seed the fermentor.

The following components were sterilized together in the fermentor vessel: 10 mL/L Modified Balch's Trace element solution, 5 g/L yeast extract, 0.2 g/L CaCl$_2$.2H$_2$O, 0.3 g/L ferric ammonium citrate, 2 g/L MgSO$_4$.7H$_2$O, 2 g/L citric acid, 7.5 g/L KH$_2$PO$_4$, 1.2 g/L sulfuric acid and 0.8 mL/L Mazu DF204 as an antifoam. After sterilization, the pH was raised to 6.8 with 40% NH$_4$OH. The concentration of ampicillin was brought to 100 g/L and the concentration of kanamycin was brought to 50 mg/mL. Two hundred forty six grams of a 65% glucose solution was added post vessel sterilization to give a 20 g/L initial concentration in the fermentor. Modified Balch's Trace elements contained 4 g/L citric acid.H$_2$0, 3 g/L MnSO$_4$.H$_2$0, 1 g/L NaCl, 0.1 g/L FeSO$_4$.7H$_2$O, 0.1 g/L ZnSO$_4$.7H$_2$O, 0.001 g/L CuSO$_4$.5H$_2$O, 0.001 g/L H$_3$BO$_3$, and 0.001 g/L NaMoO$_4$.2H$_2$O. After inoculation, the volume was 8 L and the glucose concentration was 20 g/L.

A 10-L stirred tank fermentor was prepared with the medium described above. Eight hours into the fermentation run, when the glucose concentration fell below 1 g/L, a 10% fructose bolus was added at a rate of 20 mL/min until 1 L was added. The temperature was controlled at 37° C. and the pH was maintained at 6.8 with NH$_4$OH and H$_3$PO$_4$. Back pressure was manually controlled at 0.5 bar (7.5 psig). The dissolved oxygen set point was 10%. Nine liters of cell culture was harvested.

In order to calculate the amount of tetradehydrolycopene formed during fermentation, the molar absorbance ($\epsilon_M$) at 550 nm was estimated since no values have been published. Based on the hyperchromic effect of the increasing number of double bonds in the carotenoid backbone and on the molar absorbance of the highest peak II of carotenoids with an increasing number of conjugated double bonds (phytoene, 3 conjugated double bonds, $\epsilon_M$=68,000 M$^{-1}$; phytofluene, 5 conjugated double bonds, $\epsilon_M$=73,000 M$^{-1}$; zeta-carotene, 7 conjugated double bonds, $\epsilon_M$=138,000 M$^{-1}$; neurosporene, 9 conjugated double bonds, $\epsilon_M$=157,000 M$^{-1}$ and lycopene, 11 conjugated double bonds, $\epsilon_M$=185,000 M$^{-1}$) the molar absorbance for the middle peak (peak 11) of tetradehydrolycopene (15 conjugated double bonds can be estimated to be around 240,000 M$^{-1}$). Knowing that the absorbance of tetradehydrolycopene at the third peak (peak III, 509 nm) is 85% of the absorbance at 550 nm, a wavelength where the absorption of lycopene is negligible (FIG. 8), the molar absorbance of tetradehydrolycopene at 550 nm is estimated to be around 200,000 M$^{-1}$.

Figure 3:
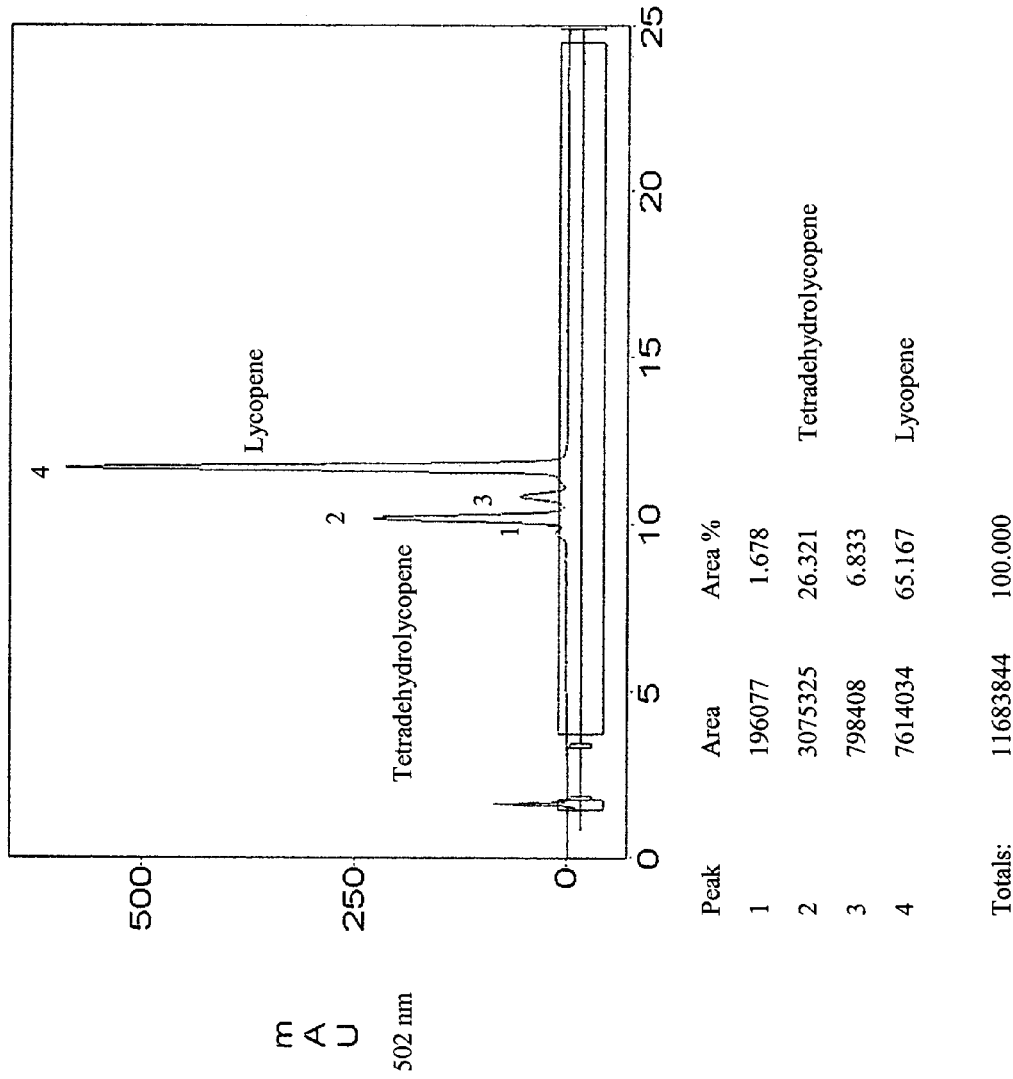
FIG. 3 shows the tracing of HPLC separation of carotenoids produced by the engineered CrtI strain.

For quantification of the tetradehydrolycopene formed, 0.5 g of cell slurry (20% dry weight, 0.1 g dry weight) was extracted with 8 mL of acetone. The absorbance of the acetone fraction at 550 nm measured to be 0.8 AU, corresponding to a tetradehydrolycopene concentration of 170 μg per gram of dry cells. In the 10-L fermentor, 114 g of cells (dry weight) were produced corresponding to a total amount of 19 mg of tetradehydrolycopene (167 ppm). The acetone was dried under nitrogen and the carotenoids were resuspended in 1 mL of methanol for HPLC analysis. The HPLC analysis was carried out as described above. There were two major peaks, and two minor peaks seen by HPLC (FIG. 3). The first major peak, peak 2, which accounted for 26.3% of the total carotenoid, was tetradehydrolycopene. The spectra for tetradehydrolycopene, from 450 nm –600 nm is seen in FIG. 8. The second major peak, peak 4, which accounted for 65.2% of the total carotenoid, was lycopene.

What is claimed is:

1. An isolated nucleic acid molecule encoding a mutant phytoene desaturase comprising:
    a) a nucleic acid molecule encoding the amino acid sequence selected from the group consisting of SEQ ID NOs:18 and 20; or
    b) is completely complementary to (a).

2. The isolated nucleic acid molecule of claim 1 selected from the group consisting of SEQ ID NOs:17 and 19.

3. A recombinant host cell comprising the isolated nucleic acid molecule of claim 1 or 2, wherein the host cell is selected from the group consisting of bacteria, algae, yeast, or filamentous fungi.

4. A method for the production of tetradehydrolycopene comprising:
    a) providing a recombinant host cell comprising:
        i) an isolated nucleic acid molecule encoding a mutant phytoene desaturase having the amino acid sequence selected from the group consisting of SEQ ID NO:18 and SEQ ID NO:20;
        ii) a phytoene desaturase substrate;
    b) growing the recombinant host cell of (a) under conditions whereby the isolated nucleic acid molecule of (a)(i) is expressed and the phytoene desaturase substrate is converted to tetradehydrolycopene; and
    c) optionally recovering the tetradehydrolycopene.

5. A method for the production of Tetradehydrolycopene comprising:
    a) providing a recombinant host cell comprising:
        i) a functional isoprenoid biosynthesis pathway, said isoprenoid biosynthesis pathway comprising at least one copy of the genes dxs, ispC, ispD, ispE, tspF, ispG, ispH, idi, and ispA; wherein one or more of the isoprenoid pathway genes is upregulated;
        ii) a functional earotenoid biosynthesis pathway, said carotenoid biosynthesis pathway comprising at least one copy of the genes crtF, crtB, and crtI; wherein one or more of the carotenoid biosynthesis genes are upregulated;
        iii) an isolated nucleic acid molecule encoding a mutant phytoene desaturase having the amino acid sequence selected from the group consisting of SEQ ID NO:18 and SEQ ID NO:20; said isolated nucleic acid molecule operably linked to suitable regulatory sequence; and
    b) growing the recombinant host cell of (a) under conditions whereby the isolated nucleic acid molecule of (a) is expressed and Tetradehydrolycopene is produced; and
    c) optionally recovering the tetradehydrolycopene.

6. A method according to either claim 4 or 5 wherein the recombinant host cell is selected from the group consisting of:
    a) a bacterium selected from the group consisting of *Salmonella, Bacillus, Acinetobacter, Rhodococcus, Streptomyces, Eseherichia, Pseudomon as, Methylomonas, Methylobacter, Alcaligenes, Synechocysils, Anabaena, Thiobacillus, Methanobactertum, Kiebsiella, Burkiiolderia, Sphingornonas, Paracoccus, Pandoraea, Deiftia*, and *Comamonas;*
    b) a yeast selected from the group consisting of *Aspergillus, Trichodenna, Soecharomyces, Pichia, Candida*, and *Hansenula;*
    c) an algal species selected from the group consisting of *Spirulina, Haemotacoccus*, and *Dunalliela.;* and d) a plant cell selected from the group consisting of soybean, rapeseed (*Brassica napus, K campestris*), sunflower (*Helian thus annus*), cotton (*Gossypium hirsutum*), corn, tobacco (*Nicotiana tabacum*), alfalfa (*Medicago sativa*), wheat (*Triticum sp*), barley (*Hordeum vulgare*), oats (*Avena saliva, L*), sorghum (*Sorghum bicolor*), rice (*Otyza saliva*), *Arabidopsis*, coniferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

7. The recombinant host cell of claim 6 wherein the bacterium is *Escherichia colt*.

8. A method according to claim 4 wherein the phytoene desaturase substrate is selected from the group consisting of phytoene, phytofluene, $\xi$-carotene, neurosporene, and lycopene.

9. A method according to either claim 4 or 5 wherein the tetradehydrolycopene is produced at a concentration of at least 150 ppm.

10. A method according to ether claim 4 or 5 wherein the tetradehydrolycopene is produced at levels of at least 10% of the total carotenoids produced by the host cell.

\* \* \* \* \*